United States Patent [19]

Wilkening et al.

[11] Patent Number: 5,756,725

[45] Date of Patent: May 26, 1998

[54] CARBAPENEM ANTIBACTERIAL COMPOUNDS, COMPOSITIONS CONTAINING SUCH COMPOUNDS AND METHODS OF TREATMENT

[75] Inventors: Robert R. Wilkening, Maplewood; Ronald W. Ratcliffe, Matawan; Timothy A. Blizzard, Rahway, all of N.J.

[73] Assignee: Merck & Co., Inc., Rahway, N.J.

[21] Appl. No.: 825,786

[22] Filed: Apr. 8, 1997

Related U.S. Application Data

[60] Provisional application No. 60/016,184, Apr. 24, 1996.

[51] Int. Cl.[6] ............ C07D 487/04; A61K 31/395
[52] U.S. Cl. ............................ 540/302; 514/210
[58] Field of Search ............... 540/302; 514/210

[56] References Cited

U.S. PATENT DOCUMENTS

| 5,034,384 | 7/1991 | Greenlee et al. | 514/210 |
|---|---|---|---|
| 5,336,674 | 8/1994 | Dininno et al. | 514/210 |

FOREIGN PATENT DOCUMENTS

| 0 429 341 A2 | 5/1991 | European Pat. Off. |
| 0 472 306 A1 | 2/1992 | European Pat. Off. |
| 0 695 753 A1 | 2/1996 | European Pat. Off. |
| WO 91/16323 | 10/1991 | WIPO |
| WO 95/21841 | 8/1995 | WIPO |

*Primary Examiner*—Mukund J. Shah
*Assistant Examiner*—King Lit Wong
*Attorney, Agent, or Firm*—Sylvia A. Ayler; Richard C. Billups; Mark R. Daniel

[57] ABSTRACT

The present invention relates to carbapenem antibacterial agents in which the carbapenem nucleus is substituted at the 2-position with a naphthosultam linked through a $CH_2$ group. The naphthosultam is further substituted with various substituent groups including at least one cationic group. The compounds are represented by formula I:

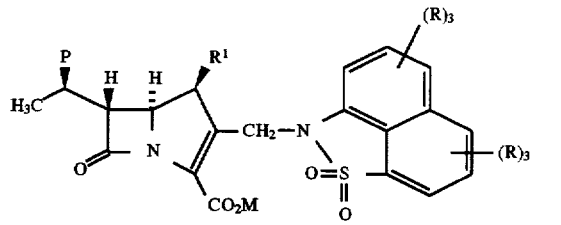

Pharmaceutical compositions and methods of use are also included.

26 Claims, No Drawings

CARBAPENEM ANTIBACTERIAL COMPOUNDS, COMPOSITIONS CONTAINING SUCH COMPOUNDS AND METHODS OF TREATMENT

This application claims the benefit of U.S. Provisional Application 60/016,184, filed Apr. 24, 1996.

BACKGROUND OF THE INVENTION

The present invention relates to carbapenem antibacterial agents in which the carbapenem nucleus is substituted at the 2-position with a naphthosultam linked through a $CH_2$ group. The naphthosultam is further substituted with various substituent groups including at least one cationic group.

The carbapenems of the present invention are useful against gram positive microorganisms, especially methicillin resistant *Staphylococcus aureus* (MRSA), methicillin resistant *Staphylococcus epidermidis* (MRSE), and methicillin resistant coagulase negative Staphylococci (MRCNS). The antibacterial compounds of the present invention thus comprise an important contribution to therapy for treating infections caused by these difficult to control pathogens. There is an increasing need for agents effective against such pathogens (MRSA/MRCNS) which are at the same time relatively free from undesirable side effects.

SUMMARY OF THE INVENTION

The compounds of the invention are represented by formula I:

or a pharmaceutically acceptable salt thereof, wherein:

$R^1$ represents H or methyl;

$CO_2M$ represents a carboxylic acid, a carboxylate anion, a pharmaceutically acceptable ester group or a carboxylic acid protected by a protecting group;

P represents hydrogen, hydroxyl, F or hydroxyl protected by a hydroxyl-protecting group;

each R is independently selected from: —R*; —Q; hydrogen; halo; —CN; —$NO_2$; —$NR^aR^b$; —$OR^c$; —$SR^c$; —C(O)$NR^aR^b$; —C(O)$OR^h$; —S(O)$R^c$; —$SO_2R^c$; —$SO_2NR^aR^b$; —$NR^aSO_2R^b$; —C(O)$R^a$; —OC(O)$R^a$; —OC(O)$NR^aR^b$; —$NR^aC(O)NR^bR^c$; —$NR^aCO_2R^h$; —$OCO_2R^h$; —$NR^aC(O)R^b$; —$C_{1-6}$ straight- or branched-chain alkyl, unsubstituted or substituted with one to four $R^d$ groups; and —$C_{3-7}$ cycloalkyl, unsubstituted or substituted with one to four $R^d$ groups;

with the proviso that at least one R is present which contains at least one positive charge;

each $R^a$, $R^b$ and $R^c$ independently represents hydrogen, —R*, —$C_{1-6}$ straight- or branched-chain alkyl, unsubstituted or substituted with one to four $R^d$ groups, or —$C_{3-7}$ cycloalkyl, unsubstituted or substituted with one to four $R^d$ groups;

or $R^a$ and $R^b$ taken together with any intervening atoms represent a 4–6 membered saturated ring optionally interrupted by one or more of O, S, $NR^c$, with $R^c$ as defined above, or —C(O)—, said ring being unsubstituted or substituted with one to four $R^i$ groups;

or $R^b$ and $R^c$ taken together with any intervening atoms represent a 4–6 membered saturated ring optionally interrupted by one to three of O, S, $NR^a$, with $R^a$ as defined above, or —C(O)—, said ring being unsubstituted or substituted with one to four $R^i$ groups;

each $R^d$ independently represents halo; —CN; —$NO_2$; —$NR^eR^f$; —$OR^g$; —$SR^g$; —$CONR^eR^f$; —$COOR^g$; —$SOR^g$; —$SO_2R^g$; —$SO_2NR^eR^f$; —$NR^eSO_2R^f$; —$COR^e$; —$NR^eCOR^f$; —$OCOR^e$; —$OCONR^eR^f$; —$NR^eCONR^fR^g$; —$NR^eCO_2R^h$; —$OCO_2R^h$; —C($NR^e$)$NR^fR^g$; —$NR^eC(NH)NR^fR^g$; —$NR^eC(NR^f)R^g$; —R*; or —Q;

$R^e$, $R^f$ and $R^g$ represent hydrogen; —R*; —$C_{1-6}$ straight- or branched-chain alkyl unsubstituted or substituted with one to four $R^i$ groups;

or $R^e$ and $R^f$ taken together with any intervening atoms represent a 4–6 membered saturated ring optionally interrupted by one to three of O, S, —C(O)— or $NR^g$ with $R^g$ as defined above, said ring being unsubstituted or substituted with one to four $R^i$ groups;

each $R^i$ independently represents halo; —CN; —$NO_2$; phenyl; —$NHSO_2R^h$; —$OR^h$; —$SR^h$; —N($R^h$)$_2$; —$N^+$($R^h$)$_3$; —C(O)N($R^h$)$_2$; —$SO_2N(R^h)_2$; heteroaryl; heteroarylium; —$CO_2R^h$; —C(O)$R^h$; —$OCOR^h$; —$NHCOR^h$; guanidinyl; carbamimidoyl or ureido;

each $R^h$ independently represents hydrogen, a —$C_{1-6}$ straight or branched-chain alkyl group, a —$C_3$–$C_6$ cycloalkyl group or phenyl, or when two $R^h$ groups are present, said $R^h$ groups may be taken in combination and represent a 4–6 membered saturated ring, optionally interrupted by one or two of O, S, $SO_2$, —C(O)—, NH and $NCH_3$;

Q is selected from the group consisting of:

wherein:

a and b are 1, 2 or 3;

$L^-$ is a pharmaceutically acceptable counterion;

α represents O, S or $NR^s$;

β, δ, λ, μ and σ represent $CR^t$, N or $N^+R^s$, provided that no more than one of β, δ, λ, μ and σ is $N^+R^s$;

R* is selected from the group consisting of:

wherein:

d represents O, S or $NR^k$;

e, g, x, y and z represent $CR^m$, N or $N^+R^k$, provided that no more than one of e, g, x, y and z in any given structure represents $N^+R^k$;

$R^k$ represents hydrogen; —$C_{1-6}$ straight- or branched-chain alkyl, unsubstituted or substituted with one to four $R^i$ groups; or —$(CH_2)_nQ$ where n=1, 2 or 3 and Q is as previously defined;

each $R^m$ independently represents a member selected from the group consisting of: hydrogen; halo; —CN; —$NO_2$; —$NR^nR^o$; —$OR^n$; —$SR^n$; —$CONR^nR^o$; —$COOR^h$; —$SOR^n$; —$SO_2R^n$; —$SO_2NR^nR^o$; —$NR^nSO_2R^o$; —$COR^n$; —$NR^nCOR^o$; —$OCOR^n$; —$OCONR^nR^o$; —$NR^nCO_2R^h$; —$NR^nCONR^oR^h$; —$OCO_2R^h$; —$CNR^nNR^oR^h$; —$NR^nCNHNR^oR^h$; —$NR^nC(NR^o)R^h$; —$C_{1-6}$ straight- or branched-chain alkyl, unsubstituted or substituted with one to four $R^i$ groups; —$C_{3-7}$ cycloalkyl, unsubstituted or substituted with one to four $R^i$ groups; and —$(CH_2)_nQ$ where n and Q are as defined above;

$R^n$ and $R^o$ represent hydrogen, phenyl; —$C_{1-6}$ straight- or branched-chain alkyl unsubstituted or substituted with one to four $R^i$ groups;

each $R^s$ independently represents hydrogen; phenyl or —$C_{1-6}$ straight- or branched-chain alkyl, unsubstituted or substituted with one to four $R^i$ groups;

each $R^t$ independently represents hydrogen; halo; phenyl; —CN; —$NO_2$; —$NR^uR^v$; —$OR^u$; —$SR^u$; —$CONR^uR^v$; —$COOR^h$; —$SOR^u$; —$SO_2R^u$; —$SO_2NR^uR^v$; —$NR^uSO_2R^v$; —$COR^u$; —$NR^uCOR^v$; —$OCOR^u$; —$OCONR^uR^v$; —$NR^uCO_2R^v$; —$NR^uCONR^vR^w$; —$OCO_2R^v$; —$C_{1-6}$ straight- or branched-chain alkyl, unsubstituted or substituted with one to four $R^i$ groups;

$R^u$ and $R^v$ represent hydrogen or —$C_{1-6}$ straight- or branched-chain alkyl, unsubstituted or substituted with one to four $R^i$ groups;

or $R^u$ and $R^v$ together with any intervening atoms represent a 4–6 membered saturated ring optionally interrupted by one or more of O, S, $NR^w$ or —C(O)—, said ring being unsubstituted or substituted with one to four $R^i$ groups;

each $R^w$ independently represents hydrogen; —$C_{1-6}$ straight- or branched-chain alkyl, unsubstituted or substituted with one to four $R^i$ groups; $C_{3-6}$ cycloalkyl optionally substituted with one to four $R^i$ groups; phenyl optionally substituted with one to four $R^i$ groups, or heteroaryl optionally substituted with 1–4 $R^i$ groups;

or $R^h$ and $R^w$ taken together with any intervening atoms represent a 5–6 membered saturated ring, optionally interrupted by one or two of O, S, $SO_2$, NH or $NCH_3$;

$R^x$ represents hydrogen or a $C_{1-8}$ straight- or branched-chain alkyl, optionally interrupted by one or two of O, S, SO, $SO_2$, $NR^w$, $N^+R^hR^w$, or —C(O)—, said chain being unsubstituted or substituted with one to four of halo, CN, $NO_2$, $OR^w$, $SR^w$, $SOR^w$, $SO_2R^w$, $NR^hR^w$, $N^+(R^h)_2R^w$, —C(O)—$R^w$, $C(O)NR^hR^w$, $SO_2NR^hR^w$, $CO_2R^w$, $OC(O)R^w$, $OC(O)NR^hR^w$, $NR^hC(O)R^w$, $NR^hC(O)NR^hR^w$, or a phenyl or heteroaryl group which is in turn optionally substituted with from one to four $R^i$ groups or with one to two $C_{1-3}$ straight- or branched-chain alkyl groups, said alkyl groups being unsubstituted or substituted with one to four $R^i$ groups;

$R^y$ and $R^z$ represent hydrogen; phenyl; —$C_{1-6}$ straight or branched chain alkyl, unsubstituted or substituted with one to four $R^i$ groups, and optionally interrupted by O, S, $NR^w$, $N^+R^hR^w$ or —C(O)—;

or $R^x$ and $R^y$ together with any intervening atoms represent a 4–6 membered saturated ring optionally interrupted by O, S, $SO_2$, $NR^w$, $N^+R^hR^w$ or —C(O)—, unsubstituted or substituted with 1–4 $R^i$ groups, and when $R^x$ and $R^y$ together represent a 4–6 membered ring as defined above, $R^z$ is as defined above or $R^z$ represents an additional saturated 4–6 membered ring fused to the ring represented by $R^x$ and $R^y$ taken together, optionally interrupted by O, S, $NR^w$ or —C(O)—, said rings being unsubstituted or substituted with one to four $R^i$ groups.

Pharmaceutical compositions and methods of treatment are also included herein.

DETAILED DESCRIPTION OF THE INVENTION

The invention is described herein in detail using the terms defined below unless otherwise specified.

Carboxylate anion refers to a negatively charged group —COO—.

The term "alkyl" refers to a monovalent alkane (hydrocarbon) derived radical containing from 1 to 10 carbon atoms unless otherwise defined. It may be straight, branched or cyclic. Preferred alkyl groups include methyl, ethyl, propyl, isopropyl, butyl, t-butyl, cyclopentyl and cyclohexyl. When substituted, alkyl groups may be substituted with up to four substituent groups, selected from $R^d$ and $R^i$, as defined, at any available point of attachment. When the alkyl group is said to be substituted with an alkyl group, this is used interchangeably with "branched alkyl group".

Cycloalkyl is a specie of alkyl containing from 3 to 15 carbon atoms, without alternating or resonating double bonds between carbon atoms. It may contain from 1 to 4 rings which are fused.

The term "alkenyl" refers to a hydrocarbon radical straight, branched or cyclic containing from 2 to 10 carbon atoms and at least one carbon to carbon double bond. Preferred alkenyl groups include ethenyl, propenyl, butenyl and cyclohexenyl.

The term "alkynyl" refers to a hydrocarbon radical straight or branched, containing from 2 to 10 carbon atoms and at least one carbon to carbon triple bond. Preferred alkynyl groups include ethynyl, propynyl and butynyl.

Aryl refers to aromatic rings e.g., phenyl, substituted phenyl and the like, as well as rings which are fused, e.g., naphthyl, phenanthrenyl and the like. An aryl group thus contains at least one ring having at least 6 atoms, with up to five such rings being present, containing up to 22 atoms therein, with alternating (resonating) double bonds between adjacent carbon atoms or suitable heteroatoms. The preferred aryl groups are phenyl, naphthyl and phenanthrenyl. Aryl groups may likewise be substituted as defined. Preferred substituted aryls include phenyl and naphthyl.

The term "heteroaryl" refers to a monocyclic aromatic hydrocarbon group having 5 or 6 ring atoms, or a bicyclic aromatic group having 8 to 10 atoms, containing at least one heteroatom, O, S or N, in which a carbon or nitrogen atom is the point of attachment, and in which one or two additional carbon atoms is optionally replaced by a heteroatom selected from O or S, and in which from 1 to 3 additional carbon atoms are optionally replaced by nitrogen heteroatoms, said heteroaryl group being optionally substituted as described herein. Examples of this type are pyrrole, pyridine, oxazole, thiazole and oxazine. Additional nitrogen atoms may be present together with the first nitrogen and oxygen or sulfur, giving, e.g., thiadiazole. Examples include the following:

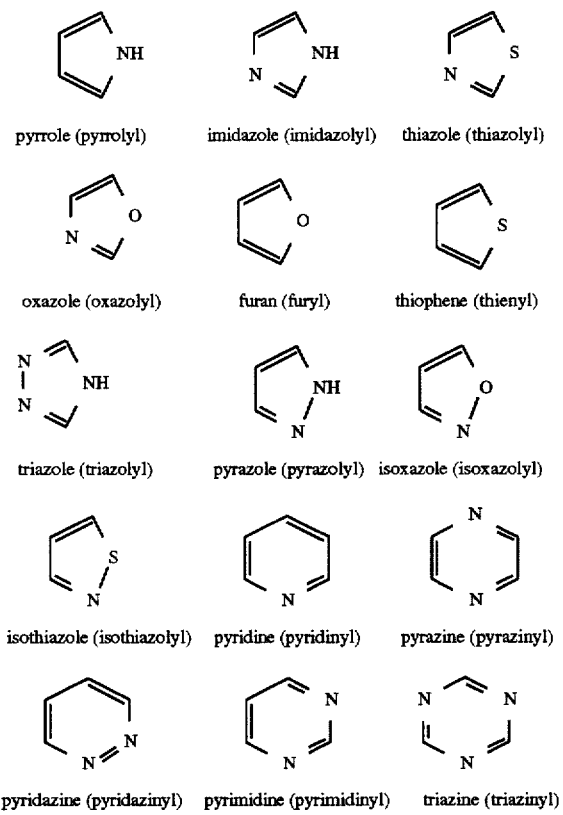

pyrrole (pyrrolyl)   imidazole (imidazolyl)   thiazole (thiazolyl)

oxazole (oxazolyl)   furan (furyl)   thiophene (thienyl)

triazole (triazolyl)   pyrazole (pyrazolyl)   isoxazole (isoxazolyl)

isothiazole (isothiazolyl)   pyridine (pyridinyl)   pyrazine (pyrazinyl)

pyridazine (pyridazinyl)   pyrimidine (pyrimidinyl)   triazine (triazinyl)

Heteroarylium refers to heteroaryl groups bearing a quaternary nitrogen atom and thus a positive charge. Examples include the following:

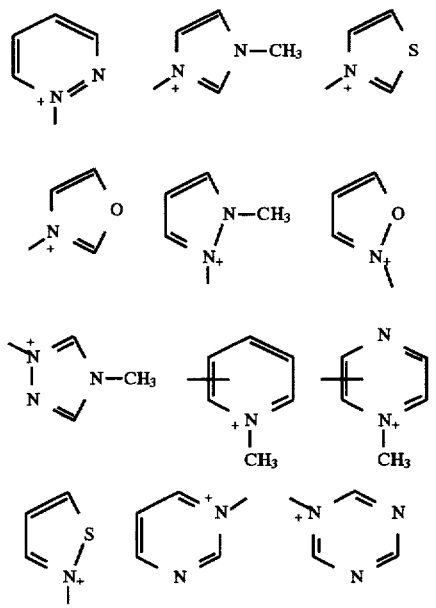

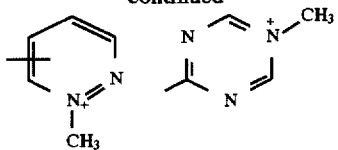

When a charge is shown on a particular nitrogen atom in a ring which contains one or more additional nitrogen atoms, it is understood that the charge may reside on a different nitrogen atom in the ring by virtue of charge resonance that occurs.

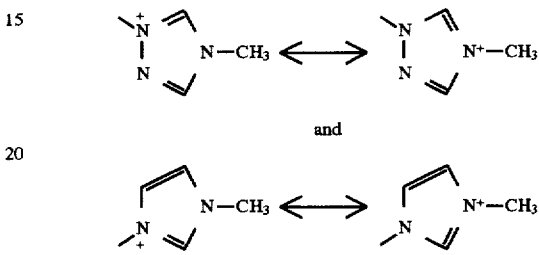

and

The term "heterocycloalkyl" refers to a cycloalkyl group (nonaromatic) in which one of the carbon atoms in the ring is replaced by a heteroatom selected from O, S or N, and in which up to three additional carbon atoms may be replaced by hetero atoms.

The terms "quaternary nitrogen" and "positive charge" refer to tetravalent, positively charged nitrogen atoms including, e.g., the positively charged nitrogen in a tetraalkylammonium group (e.g. tetramethylammonium), heteroarylium, (e.g., N-methylpyridinium), basic nitrogens which are protonated at physiological pH, and the like. Cationic groups thus encompass positively charged nitrogen-containing groups, as well as basic nitrogens which are protonated at physiologic pH.

The term "heteroatom" means O, S or N, selected on an independent basis.

Halogen and "halo" refer to bromine, chlorine, fluorine and iodine.

Alkoxy refers to $C_1$–$C_4$ alkyl-O—, with the alkyl group optionally substituted as described herein.

When a group is termed "substituted", unless otherwise indicated, this means that the group contains from 1 to 4 substituents thereon. With respect to R, $R^a$, $R^b$ and $R^c$, the substituents available on alkyl groups are selected from the values of $R^d$. Many of the variable groups are optionally substituted with up to four $R^i$ groups. With respect to $R^e$, $R^f$ and $R^g$, when these variables represent substituted alkyl, the substituents available thereon are selected from the values of $R^i$.

When a functional group is termed "protected", this means that the group is in modified form to preclude undesired side reactions at the protected site. Suitable protecting groups for the compounds of the present invention will be recognized from the present application taking into account the level of skill in the art, and with reference to standard textbooks, such as Greene, T. W. et al. *Protective Groups in Organic Synthesis* Wiley, New York (1991). Examples of suitable protecting groups are contained throughout the specification.

In some of the carbapenem compounds of the present invention, M is a readily removable carboxyl protecting group, and/or P represents a hydroxyl which is protected by a hydroxyl-protecting group. Such conventional protecting groups consist of known groups which are used to protectively block the hydroxyl or carboxyl group during the synthesis procedures described herein. These conventional blocking groups are readily removable, i.e., they can be removed, if desired, by procedures which will not cause cleavage or other disruption of the remaining portions of the molecule. Such procedures include chemical and enzymatic hydrolysis, treatment with chemical reducing or oxidizing agents under mild conditions, treatment with a transition metal catalyst and a nucleophile and catalytic hydrogenation.

Examples of carboxyl protecting groups include allyl, benzhydryl, 2-naphthylmethyl, benzyl, silyl such as t-butyldimethylsilyl (TBDMS), phenacyl, p-methoxybenzyl, o-nitrobenzyl, p-methoxyphenyl, p-nitrobenzyl, 4-pyridylmethyl and t-butyl.

Examples of suitable C-6 hydroxyethyl protecting groups include triethylsilyl, t-butyldimethylsilyl, o-nitrobenzyloxycarbonyl, p-nitrobenzyloxycarbonyl, benzyloxycarbonyl, allyloxycarbonyl, t-butyloxycarbonyl, 2,2,2-trichloroethyloxycarbonyl and the like.

The carbapenem compounds of the present invention are useful per se and in their pharmaceutically acceptable salt and ester forms for the treatment of bacterial infections in animal and human subjects. The term "pharmaceutically acceptable ester, salt or hydrate," refers to those salts, esters and hydrated forms of the compounds of the present invention which would be apparent to the pharmaceutical chemist, i.e., those which are substantially non-toxic and which may favorably affect the pharmacokinetic properties of said compounds, such as palatability, absorption, distribution, metabolism and excretion. Other factors, more practical in nature, which are also important in the selection, are cost of the raw materials, ease of crystallization, yield, stability, solubility, hygroscopicity and flowability of the resulting bulk drug. Conveniently, pharmaceutical compositions may be prepared from the active ingredients in combination with pharmaceutically acceptable carriers. Thus, the present invention is also concerned with pharmaceutical compositions and methods of treating bacterial infections utilizing as an active ingredient the novel carbapenem compounds.

With respect to —$CO_2M$, which is attached to the carbapenem nucleus at position 3, this represents a carboxylic acid group (M represents H), a carboxylate anion (M represents a negative charge), a pharmaceutically acceptable ester (M represents an ester forming group) or a carboxylic acid protected by a protecting group (M represents a carboxyl protecting group). The pharmaceutically acceptable salts referred to above may take the form —COOM, where M is a negative charge, which is balanced by a counterion, e.g., an alkali metal cation such as sodium or potassium. Other pharmaceutically acceptable counterions may be calcium, magnesium, zinc, ammonium, or alkylammonium cations such as tetramethylammonium, tetrabutylammonium, choline, triethylhydroammonium, meglumine, triethanolhydroammonium, etc.

The pharmaceutically acceptable salts referred to above also include acid addition salts. Thus, the Formula I compounds can be used in the form of salts derived from inorganic or organic acids. Included among such salts are the following: acetate, adipate, alginate, aspartate, benzoate, benzenesulfonate, bisulfate, butyrate, citrate, camphorate, camphorsulfonate, cyclopentanepropionate, digluconate, dodecylsulfate, ethanesulfonate, fumarate, glucoheptanoate, glycerophosphate, hemisulfate, heptanoate, hexanoate, hydrochloride, hydrobromide, hydroiodide, 2-hydroxyethanesulfonate, lactate, maleate, methanesulfonate, 2-naphthalenesulfonate, nicotinate, oxalate, pamoate, pectinate, persulfate, 3-phenylpropionate, picrate, pivalate, propionate, succinate, tartrate, thiocyanate, tosylate and undecanoate.

The pharmaceutically acceptable esters are such as would be readily apparent to a medicinal chemist, and include, for example, those described in detail in U.S. Pat. No. 4,309,438. Included within such pharmaceutically acceptable esters are those which are hydrolyzed under physiological conditions, such as pivaloyloxymethyl, acetoxymethyl, phthalidyl, indanyl and methoxymethyl, and others described in detail in U.S. Pat. No. 4,479,947. These are also referred to as "biolabile esters".

Biolabile esters are biologically hydrolizable, and may be suitable for oral administration, due to good absorption through the stomach or intenstinal mucosa, resistance to gastric acid degradation and other factors. Examples of biolabile esters include compounds in which M represents an alkoxyalkyl, alkylcarbonyloxyalkyl, alkoxycarbonyloxyalkyl, cycloalkoxyalkyl, alkenyloxyalkyl, aryloxyalkyl, alkoxyaryl, alkylthioalkyl, cycloalkylthioalkyl, alkenylthioalkyl, arylthioalkyl or alkylthioaryl group. These groups can be substituted in the alkyl or aryl portions thereof with acyl or halo groups. The following M species are examples of biolabile ester forming moieties.: acetoxymethyl, 1-acetoxyethyl, 1-acetoxypropyl, pivaloyloxymethyl, 1-isopropyloxycarbonyloxyethyl, 1-cyclohexyloxycarbonyloxyethyl, phthalidyl and (2-oxo-5-methyl-1,3-dioxolen-4-yl)methyl.

$L^-$ can be present or absent as necessary to maintain the appropriate charge balance. When present, $L^-$ represents a pharmaceutically acceptable counterion. Most anions derived from inorganic or organic acids are suitable. Representative examples of such counterions are the following: acetate, adipate, aminosalicylate, anhydromethylenecitrate, ascorbate, aspartate, benzoate, benzenesulfonate, bromide, citrate, camphorate, camphorsulfonate, chloride, estolate, ethanesulfonate, fumarate, glucoheptanoate, gluconate, glutamate, lactobionate, malate, maleate, mandelate, methanesulfonate, pantothenate, pectinate, phosphate/diphosphate, polygalacturonate, propionate, salicylate, stearate, succinate, sulfate, tartrate and tosylate. Other suitable anionic species will be apparent to the ordinarily skilled chemist.

Likewise, when L– represents a specie with more than one negative charge, such as malonate, tartrate or ethylenediaminetetraacetate (EDTA), an appropriate number of carbapenem molecules can be found in association therewith to maintain the overall charge balance and neutrality.

Numbering of the naphthosultam platform is as follows:

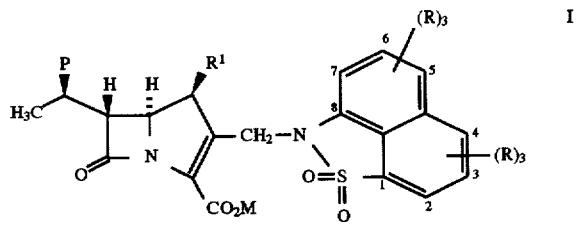

At least one of the R groups attached to the naphthosultam platform contains a positively charged moiety. Thus, it can include —R* or Q, or a moiety which in turn contains a positively charged group.

A subset of compounds of formula I which is of interest relates to those compounds where CO$_2$M represents a carboxylate anion. Hence, M in this instance represents a negative charge which will be balanced by a positively charged group, such as in the positively charged R group. Likewise, if the positively charged R group contains more than one positive charge, a negatively charged counterion may be present which in combination with the carboxylate anion, provides overall charge neutrality.

Another subset of compounds of formula I which is of interest relates to compounds of formula I wherein one R represents a group which contains a positively charged moiety, and the remaining R groups are selected from hydrogen and C$_{1-6}$ straight or branched chain alkyl, unsubstituted or substituted with one to four R$^d$ groups. More particularly, this subset of interest includes compounds of formula I wherein one R represents a group containing a positively charged moiety and the remaining R groups are hydrogen.

With respect to the positively charged moiety or moieties that are contained in one or more R groups, it is preferred that from 1–3 positive charges be present, and most preferably two positive charges be present, balanced by the carboxylate anion and a negatively charged counterion.

Another subset of compounds which is of interest is represented by formula I wherein one R group represents a —C$_{1-6}$ straight or branched chain alkyl group, substituted with one to four R$^d$ groups, wherein one R$^d$ group represents —R* or Q. Hence, a positively charged moiety —R* or Q is attached to an alkyl group.

Another group of compounds of interest is represented by formula I wherein Q is selected from the group consisting of:

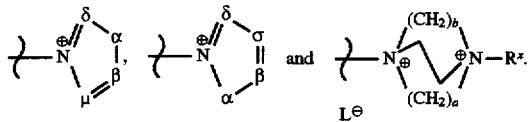

More particularly, the group of compounds which is of interest is represented by formula I wherein Q represents:

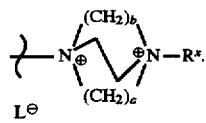

Within this subset of compounds, L⁻, a and b are as originally defined, and R$^x$ is as originally defined, and represents a member selected from the group consisting of: hydrogen or a C$_{1-8}$ straight- or branched-chain alkyl, optionally interrupted by one or two of O, S, SO, SO$_2$, NR$^w$, N$^+$R$^h$R$^w$, or —C(O)—, said chain being unsubstituted or substituted with one to four of halo, CN, NO$_2$, OR$^w$, SR$^w$, SOR$^w$, SO$_2$R$^w$, NR$^h$R$^w$, N$^+$(R$^h$)$_2$R$^w$, —C(O)—R$^w$, C(O)NR$^h$R$^w$, SO$_2$NR$^h$R$^w$, CO$_2$R$^w$, OC(O)R$^w$, OC(O)NR$^h$R$^w$, NR$^h$C(O)R$^w$, NR$^h$C(O)NR$^h$R$^w$, or a phenyl or heteroaryl group which is in turn optionally substituted with from one to four R$^i$ groups or with one to two C$_{1-3}$ straight- or branched-chain alkyl groups, said alkyl groups being unsubstituted or substituted with one to four R$^i$ groups.

Another group of compounds of interest is represented by formula I wherein Q represents —N$^+$R$^x$R$^y$R$^z$, wherein R$^x$, R$^y$ and R$^z$ are as originally defined.

Another group of compounds of interest is represented by formula I wherein one R* group is present and is selected from:

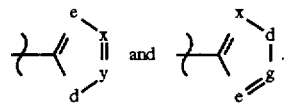

Within this subset, d represents NR$^k$; R$^k$ represents —C$_{1-6}$ straight or branched chain alkyl; and e, g, x and y represent CR$^m$ or N$^+$R$^k$, with R$^k$ as defined above and R$^m$ representing hydrogen.

A preferred subset of compounds of formula I which is of particular interest relates to compounds represented by formula I wherein:

CO$_2$M represents a carboxylate anion;

one R group which is attached to the naphthosultam platform contains at least one positively charged moiety, and the remaining R groups are selected from hydrogen and C$_{1-6}$ straight or branched chain alkyl, unsubstituted or substituted with one to four R$^d$ groups;

R$^d$ is as originally defined;

R$^h$ represents hydrogen or a C$_{1-6}$ straight or branched chain alkyl group;

Q is selected from the group consisting of:

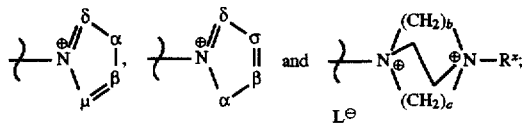

wherein L⁻, a and b are as originally defined, and R$^x$ represents a member selected from the group consisting of: hydrogen or a C$_{1-8}$ straight- or branched-chain alkyl, optionally interrupted by one or two of O, S, SO, SO$_2$, NR$^w$, N$^+$R$^h$R$^w$, or —C(O)—, said chain being unsubstituted or substituted with one to four of halo, CN, NO$_2$, OR$^w$, SR$^w$, SOR$^w$, SO$_2$R$^w$, NR$^h$R$^w$, N$^+$(R$^h$)$_2$R$^w$, —C(O)—R$^w$, C(O)NR$^h$R$^w$, SO$_2$NR$^h$R$^w$, CO$_2$R$^w$, OC(O)R$^w$, OC(O)NR$^h$R$^w$, NR$^h$C(O)R$^w$, NR$^h$C(O) NR$^h$R$^w$, or a phenyl or heteroaryl group which is in turn optionally substituted with from one to four RI groups or with one to two C$_{1-3}$ straight- or branched-chain alkyl groups, said alkyl groups being unsubstituted or substituted with one to four R$^i$ groups;

R* is selected from:

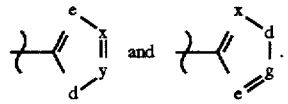

wherein d represents NR$^k$; R$^k$ represents —C$_{1-6}$ straight or branched chain alkyl; and e, g, x and y represent CR$^m$ or N$^+$R$^k$, with R$^k$ as defined above and R$^m$ representing hydrogen.

Within this subset, all other variables are as originally defined with respect to formula I.

A more preferred subset of compounds of the invention is represented by formula Ia:

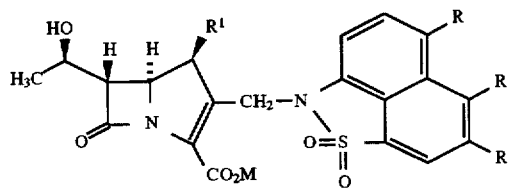

Ia or a pharmaceutically acceptable salt thereof, wherein:

CO$_2$M represents a carboxylate anion;

one R group is attached to the naphthosultam platform which contains a positively charged moiety, and the other R groups are selected from hydrogen and C$_{1-6}$ straight or branched chain alkyl, unsubstituted or substituted with one to four R$^d$ groups;

R$^d$ is as originally defined;

Q is selected from the group consisting of:

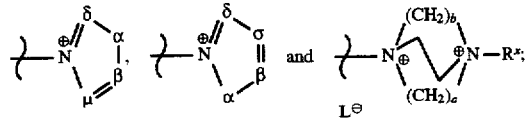

wherein L$^-$, a and b are as originally defined, and R$^x$ represents a member selected from the group consisting of: hydrogen or a C$_{1-8}$ straight- or branched-chain alkyl, optionally interrupted by one or two of O, S, SO, SO$_2$, NR$^w$, N$^+$R$^h$R$^w$, or —C(O)—, said chain being unsubstituted or substituted with one to four of halo, CN, NO$_2$, OR$^w$, SR$^w$, SOR$^w$, SO2R$^w$, NR$^h$R$^w$, N$^+$(R$^h$)$_2$R$^w$, —C(O)—R$^w$, C(O)NR$^h$R$^w$, SO$_2$NR$^h$R$^w$, CO2R$^w$, OC(O)R$^w$, OC(O)NR$^h$R$^w$, NR$^h$C(O)R$^w$, NR$^h$C(O)NR$^h$R$^w$, or a phenyl or heteroaryl group which is in turn optionally substituted with from one to four R$^1$ groups or with one to two C$_{1-3}$ straight- or branched-chain alkyl groups, said alkyl groups being unsubstituted or substituted with one to four R$^i$ groups;

R$^h$ represents hydrogen or a C$_{1-6}$ straight or branched chain alkyl group;

R$^w$ is as originally defined;

R* is selected from:

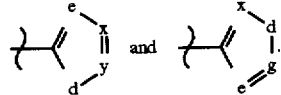

wherein d represents NR$^k$; R$^k$ represents —C$_{1-6}$ straight or branched chain alkyl; and e, g, x and y represent CR$^m$ or N$^+$R$^k$, with R$^k$ as defined above and R$^m$ representing hydrogen.

Within this subset, all other variables are as originally defined with respect to formula I.

Another more preferred subset of compounds is represented by formula Ib:

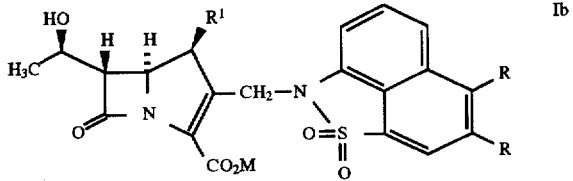

Ib or a pharmaceutically acceptable salt thereof, wherein:

CO$_2$M represents a carboxylate anion;

one R group is attached to the naphthosultam platform which contains a positively charged moiety, and the other R group is selected from hydrogen and C$_{1-6}$ straight or branched chain alkyl, unsubstituted or substituted with one to four R$^d$ groups;

R$^d$ is as originally defined;

Q is selected from the group consisting of:

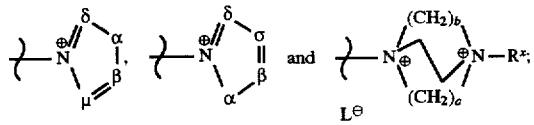

wherein L$^-$, a and b are as originally defined, and R$^x$ represents a member selected from the group consisting of: hydrogen or a C$_{1-8}$ straight- or branched-chain alkyl, optionally interrupted by one or two of O, S, SO, SO$_2$, NR$^w$, N$^+$R$^h$R$^w$, or —C(O)—, said chain being unsubstituted or substituted with one to four of halo, CN, NO$_2$, OR$^w$, SR$^w$, SOR$^w$, SO$_2$R$^w$, NR$^h$R$^w$, N$^+$(R$^h$)$_2$R$^w$, —C(O)—R$^w$, C(O)NR$^h$R$^w$, SO$_2$NR$^h$R$^w$, CO$_2$R$^w$, OC(O)R$^w$, OC(O)NR$^h$R$^w$, NR$^h$C(O)R$^w$, NR$^h$C(O)NR$^h$R$^w$, or a phenyl or heteroaryl group which is in turn optionally substituted with from one to four R$^1$ groups or with one to two C$_{1-3}$ straight- or branched-chain alkyl groups, said alkyl groups being unsubstituted or substituted with one to four R$^i$ groups;

R$^h$ represents hydrogen or a C$_{1-6}$ straight or branched chain alkyl group;

R$^w$ is as originally defined;

R* is selected from:

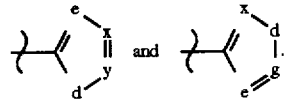

wherein d represents NR$^k$; R$^k$ represents —C$_{1-6}$ straight or branched chain alkyl; and e, g, x and y represent CR$^m$ or N$^+$R$^k$, with R$^k$ as defined above and R$^m$ representing hydrogen. Within this subset, all other variables are as originally defined with respect to formula I.

Another more preferred subset of compounds is represented by formula Ic:

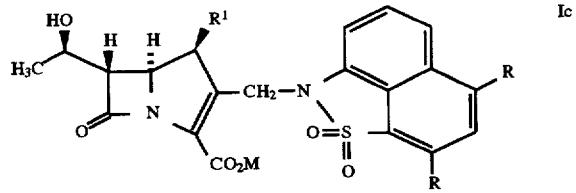

Ic or a pharmaceutically acceptable salt thereof, wherein:

CO$_2$M represents a carboxylate anion;

one R group is attached to the naphthosultam platform which contains a positively charged moiety, and the other R group is selected from hydrogen, halo and C$_{1-6}$ straight or branched chain alkyl, unsubstituted or substituted with one to four R$^d$ groups;

R$^d$ is as originally defined;

Q is selected from the group consisting of:

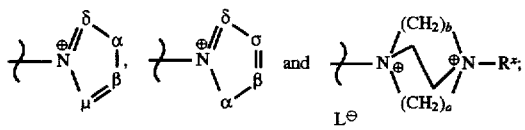

wherein L$^-$, a and b are as originally defined, and R$^x$ represents a member selected from the group consisting of: hydrogen or a C$_{1-8}$ straight- or branched-chain alkyl, optionally interrupted by one or two of O, S, SO, SO$_2$, NR$^w$, N$^+$R$^h$R$^w$, or —C(O)—, said chain being unsubstituted or substituted with one to four of halo, CN, NO$_2$, OR$^w$, SR$^w$, SOR$^w$, SO$_2$R$^w$, NR$^h$R$^w$, N$^+$(R$^h$)$_2$R$^w$, —C(O)—R$^w$, C(O)NR$^h$R$^w$, SO$_2$NR$^h$R$^w$, CO$_2$R$^w$, OC(O)R$^w$, OC(O)NR$^h$R$^w$, NR$^h$C(O)R$^w$, NR$^h$C(O)NR$^h$R$^w$, or a phenyl or heteroaryl group which is in turn optionally substituted with from one to four R$^i$ groups or with one to two C$_{1-3}$ straight- or branched-chain alkyl groups, said alkyl groups being unsubstituted or substituted with one to four R$^i$ groups;

R$^h$ represents hydrogen or a C$_{1-6}$ straight or branched chain alkyl group;

R$^w$ is as originally defined;

R* is selected from:

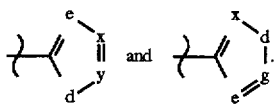

wherein d represents NR$^k$; R$^k$ represents —C$_{1-6}$ straight or branched chain alkyl; and e, g, x and y represent CR$^m$ or N$^+$R$^k$, with R$^k$ as defined above and R$^m$ representing hydrogen. Within this subset, all other variables are as originally defined with respect to formula I.

Another more preferred subset of compounds is represented by formula Id:

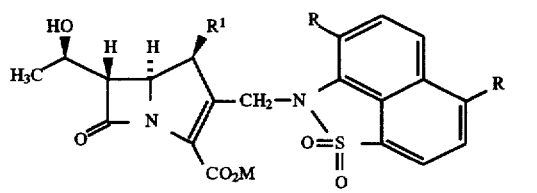

or a pharmaceutically acceptable salt thereof, wherein:

CO$_2$M represents a carboxylate anion;

one R group is attached to the naphthosultam platform which contains a positively charged moiety, and the other R group is selected from hydrogen, halo and C$_{1-6}$ straight or branched chain alkyl, unsubstituted or substituted with one to four R$^d$ groups;

R$^d$ is as originally defined;

Q is selected from the group consisting of:

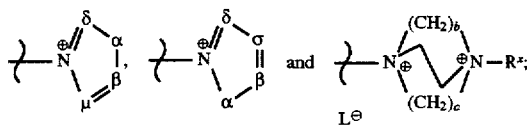

wherein L$^-$, a and b are as originally defined, and R$^x$ represents a member selected from the group consisting of: hydrogen or a C$_{1-8}$ straight- or branched-chain alkyl, optionally interrupted by one or two of O, S, SO, SO$_2$, NR$^w$, N$^+$R$^h$R$^w$, or —C(O)—, said chain being unsubstituted or substituted with one to four of halo, CN, NO$_2$, OR$^w$, SR$^w$, SOR$^w$, SO$_2$R$^w$, NR$^h$R$^w$, N$^+$(R$^h$)$_2$R$^w$, —C(O)—R$^w$, C(O)NR$^h$R$^w$, SO$_2$NR$^h$R$^w$, CO$_2$R$^w$, OC(O)R$^w$, OC(O)NR$^h$R$^w$, NR$^h$C(O)R$^w$, NR$^h$C(O)NR$^h$R$^w$, or a phenyl or heteroaryl group which is in turn optionally substituted with from one to four R$^1$ groups or with one to two C$_{1-3}$ straight- or branched-chain alkyl groups, said alkyl groups being unsubstituted or substituted with one to four R$^i$ groups;

R$^h$ represents hydrogen or a C$_{1-6}$ straight or branched chain alkyl group;

R$^w$ is as originally defined;

R* is selected from:

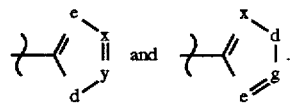

wherein d represents NR$^k$; R$^k$ represents —C$_{1-6}$ straight or branched chain alkyl; and e, g, x and y represent CR$^m$ or N$^+$R$^k$, with R$^k$ as defined above and R$^m$ representing hydrogen. Within this subset, all other variables are as originally defined with respect to formula I.

Still more preferably, the present invention relates to a compound represented by formula Ia wherein the R group at position 4 represents a positively charged moiety, and the R groups at position 3 and 5 represent hydrogen.

In particular, such compounds can be represented by formula Ie:

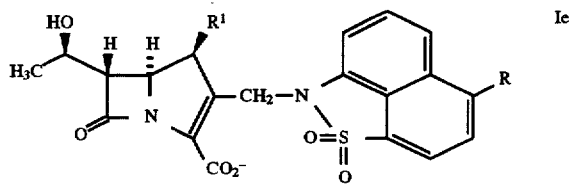

or a pharmaceutically acceptable salt thereof, wherein:

R contains a positively charged moiety selected from the group consisting of: —R*, Q, and a C$_{1-6}$ straight or branched alkyl chain substituted with one R$^d$ group;

R$^d$ is independently selected —R* or Q;

Q is selected from the group consisting of:

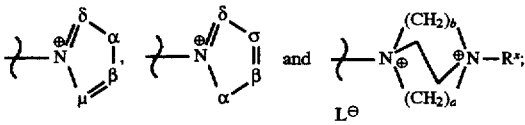

wherein L$^-$, a and b are as originally defined, and R$^x$ represents a member selected from the group consisting of: hydrogen or a $C_{1-8}$ straight- or branched-chain alkyl, optionally interrupted by one or two of O, S, SO, $SO_2$, $NR^w$, $N^+R^hR^w$, or —C(O)—, said chain being unsubstituted or substituted with one to four of halo, CN, $NO_2$, $OR^w$, $SR^w$, $SOR^w$, $SO_2R^w$, $NR^hR^w$, $N^+(R^h)_2R^w$, —C(O)—$R^w$, C(O)$NR^hR^w$, $SO_2NR^hR^w$, $CO_2R^w$, OC(O)$R^w$, OC(O)$NR^hR^w$, $NR^hC(O)R^w$, $NR^hC(O)NR^hR^w$, or a phenyl or heteroaryl group which is in turn optionally substituted with from one to four $R^i$ groups or with one to two $C_{1-3}$ straight- or branched-chain alkyl groups, said alkyl groups being unsubstituted or substituted with one to four $R^i$ groups;

R* is selected from:

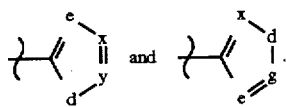

wherein d represents $NR^k$; $R^k$ represents —$C_{1-6}$ straight or branched chain alkyl; and e, g, x and y represent $CR^m$ or $N^+R^k$, with $R^k$ as defined above and $R^m$ representing hydrogen.

Likewise, such compounds can be represented by formula If:

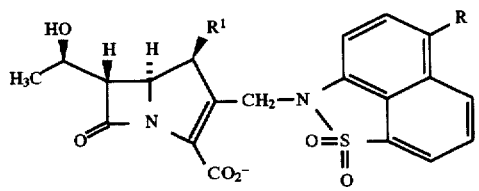

or a pharmaceutically acceptable salt thereof, wherein:

R contains a positively charged moiety selected from the group consisting of: —R*, Q, and a $C_{1-6}$ straight or branched alkyl chain substituted with one $R^d$ group;

$R^d$ is independently selected —R* or Q;

Q is selected from the group consisting of:

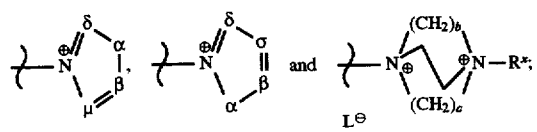

wherein $L^-$, a and b are as originally defined, and $R^x$ represents a member selected from the group consisting of: hydrogen or a $C_{1-8}$ straight- or branched-chain alkyl, optionally interrupted by one or two of O, S, SO, $SO_2$, $NR^w$, $N^+R^hR^w$, or —C(O)—, said chain being unsubstituted or substituted with one to four of halo, CN, $NO_2$, $OR^w$, $SR^w$, $SOR^w$, $SO_2R^w$, $NR^hR^w$, $N^+(R^h)_2R^w$, —C(O)—$R^w$, C(O)$NR^hR^w$, $SO_2NR^hR^w$, $CO_2R^w$, OC(O)$R^w$, OC(O)$NR^hR^w$, $NR^hC(O)R^w$, $NR^hC(O)NR^hR^w$, or a phenyl or heteroaryl group which is in turn optionally substituted with from one to four $R^i$ groups or with one to two $C_{1-3}$ straight- or branched-chain alkyl groups, said alkyl groups being unsubstituted or substituted with one to four $R^i$ groups;

R* is selected from:

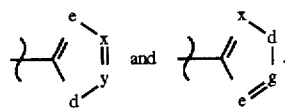

wherein d represents $NR^k$; $R^k$ represents —$C_{1-6}$ straight or branched chain alkyl; and e, g, x and y represent $CR^m$ or $N^+R^k$, with $R^k$ as defined above and $R^m$ representing hydrogen.

A still more preferred subset of compounds of the invention is represented by formula Ie wherein:

R represents

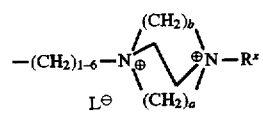

and $R^x$, a, b and $L^-$ are as originally defined.

Another more preferred subset of compounds of the invention is represented by formula Ig:

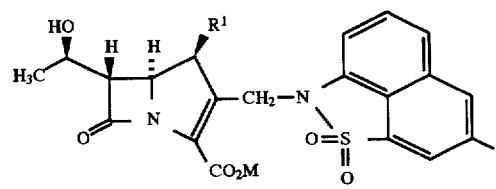

wherein:

R represents

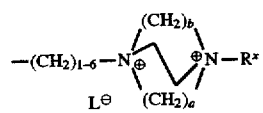

and $R^x$, a, b and $L^-$ are as originally defined.

Representative examples of compounds of the invention are as follows:

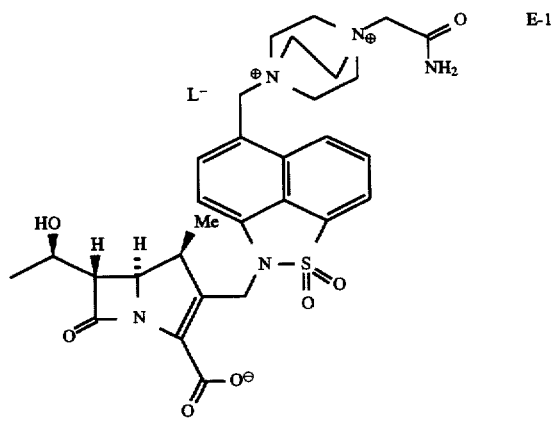

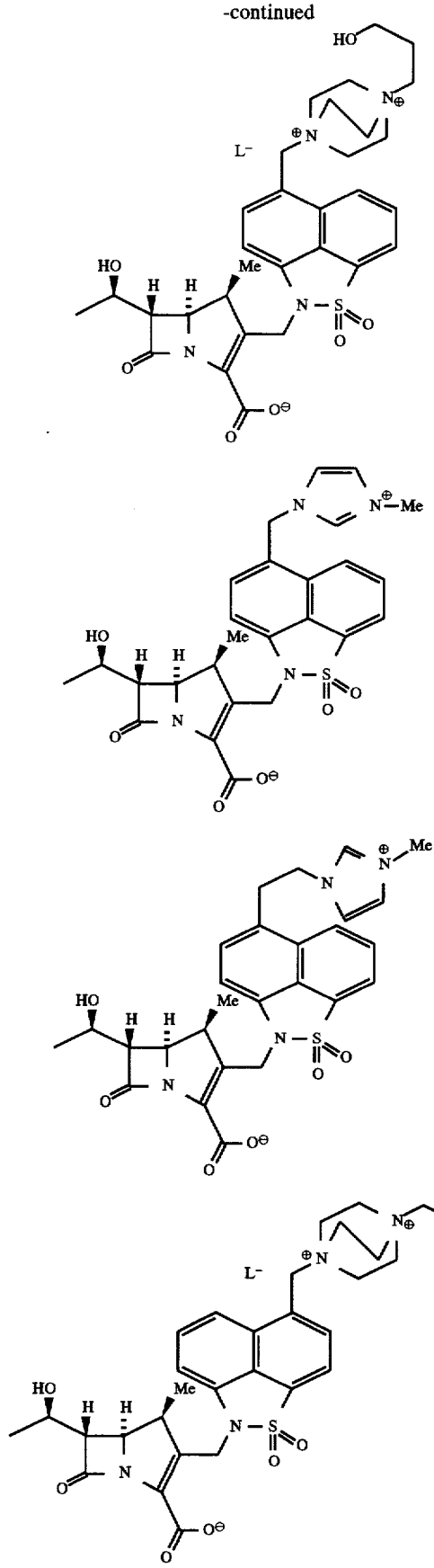
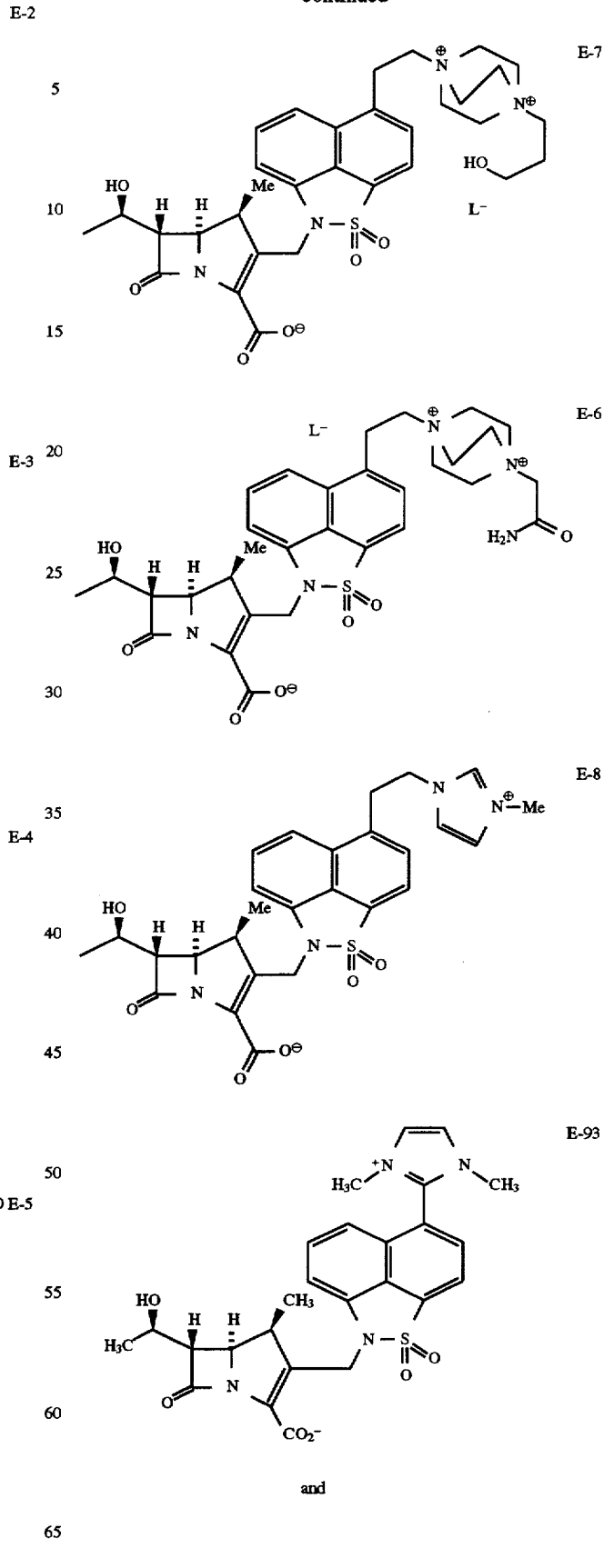
and

-continued
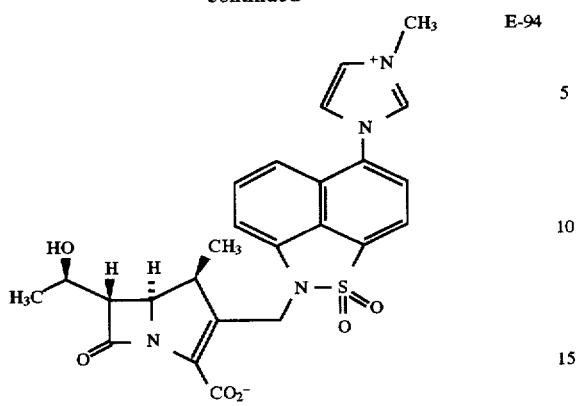
E-94
TABLE
| # | Q | # | Q | # | Q |
|---|---|---|---|---|---|
| 9 | OH-CH2CH2-N+(DABCO) | 10 | PhS-CH2CH2CH2-N+(DABCO) | 11 | F-CH2CH2-N+(DABCO) |
| 12 | F-CH2CH2CH2-N+(DABCO) | 13 | H2N-C(=O)-NH-CH2CH2CH2-N+(DABCO) | 14 | H2N-C(=O)-O-CH2CH2CH2-N+(DABCO) |

TABLE-continued
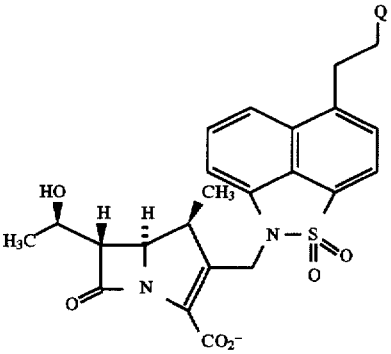
| # | Q | # | Q | # | Q |
|---|---|---|---|---|---|
| 15 | 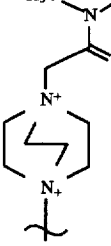 | 16 | 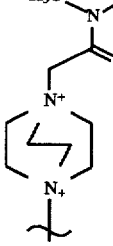 | 17 | 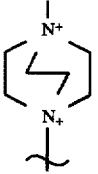 |
| 18 | 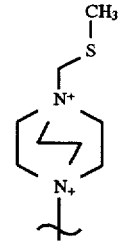 | 19 | 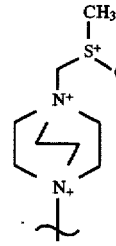 | 20 | 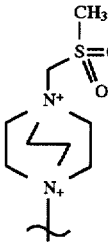 |
| 21 | 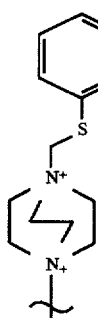 | 22 | 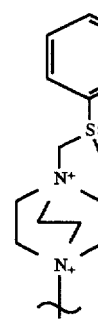 | 23 | 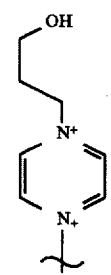 |
| 24 | 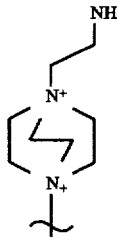 | 25 | 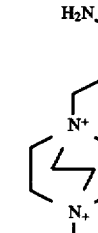 | 26 | 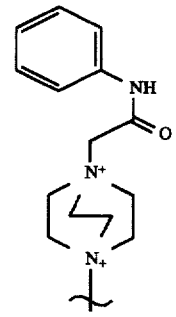 |

TABLE
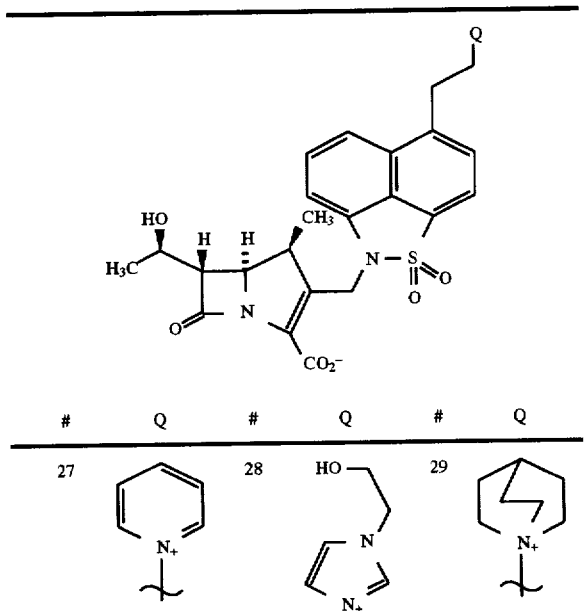
| # | Q | # | Q | # | Q |
|---|---|---|---|---|---|
| 27 | pyridinium | 28 | HO-ethyl-imidazolium | 29 | DABCO |
| 30 | thiazolium | 31 | oxazolium | 32 | quinuclidinium |
TABLE
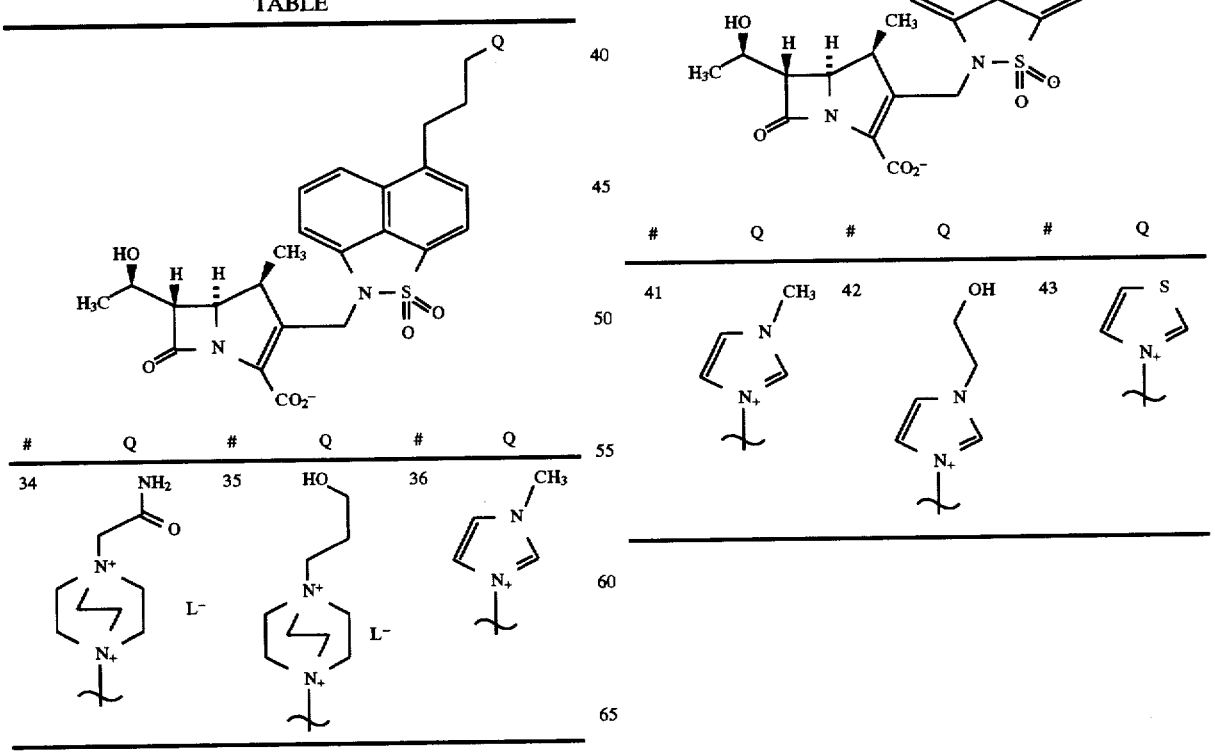
| # | Q | # | Q | # | Q |
|---|---|---|---|---|---|
| 34 | carbamoylmethyl-DABCO L⁻ | 35 | HO-propyl-DABCO L⁻ | 36 | N-methyl-imidazolium |
TABLE
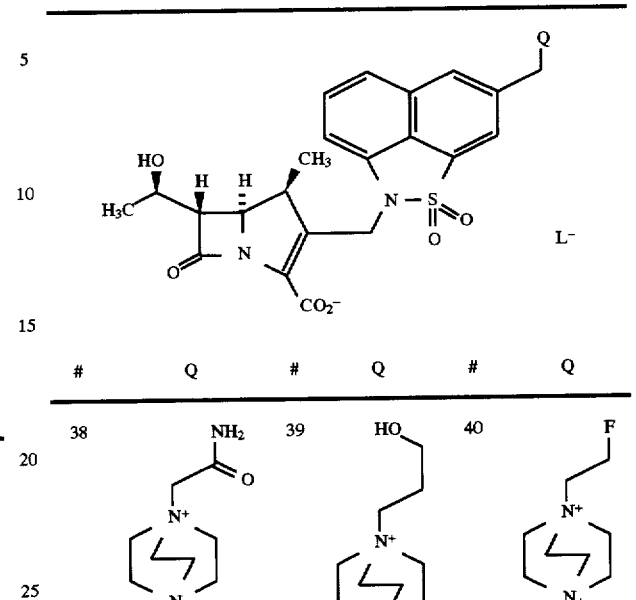
| # | Q | # | Q | # | Q |
|---|---|---|---|---|---|
| 38 | carbamoylmethyl-DABCO | 39 | HO-propyl-DABCO | 40 | F-ethyl-DABCO |
TABLE
| # | Q | # | Q | # | Q |
|---|---|---|---|---|---|
| 41 | N-methyl-imidazolium | 42 | HO-ethyl-imidazolium | 43 | thiazolium |

TABLE
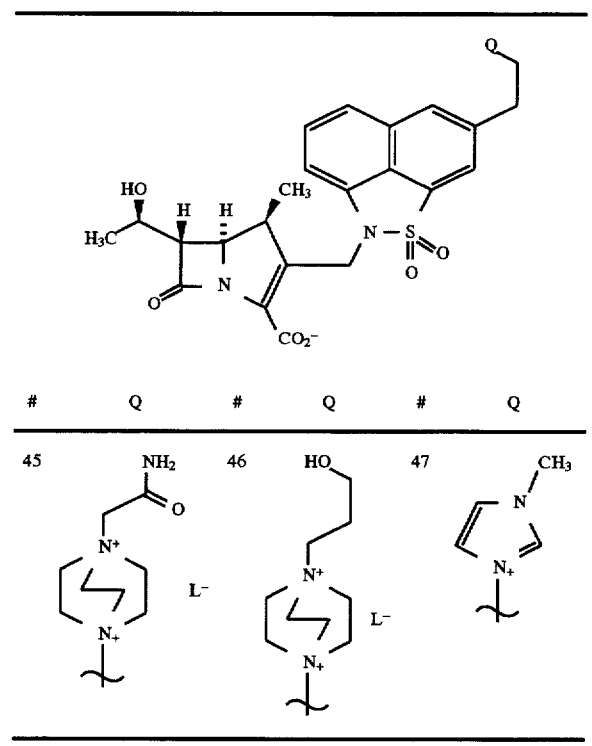
| # | Q | # | Q | # | Q |
|---|---|---|---|---|---|
| 45 | (NH₂ amide piperazinium) L⁻ | 46 | (HO-propyl piperazinium) L⁻ | 47 | (N-methyl imidazolium) |
TABLE
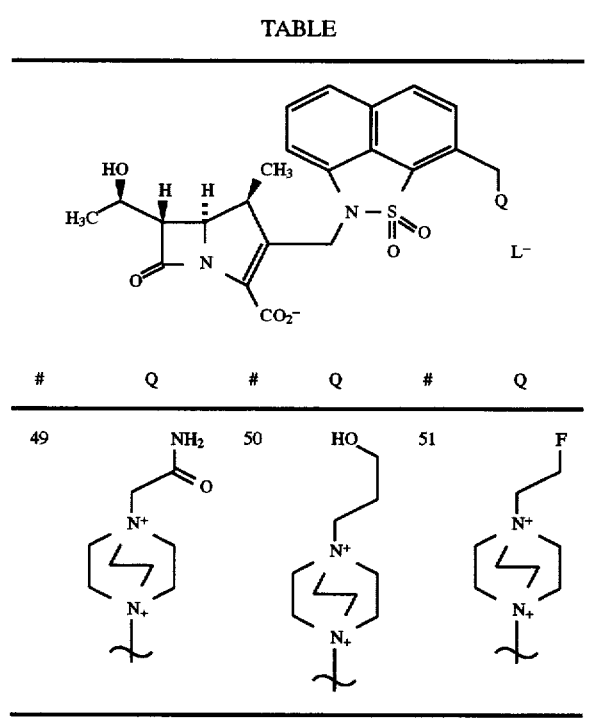
| # | Q | # | Q | # | Q |
|---|---|---|---|---|---|
| 49 | (NH₂ amide piperazinium) | 50 | (HO-ethyl piperazinium) | 51 | (F-ethyl piperazinium) |
TABLE
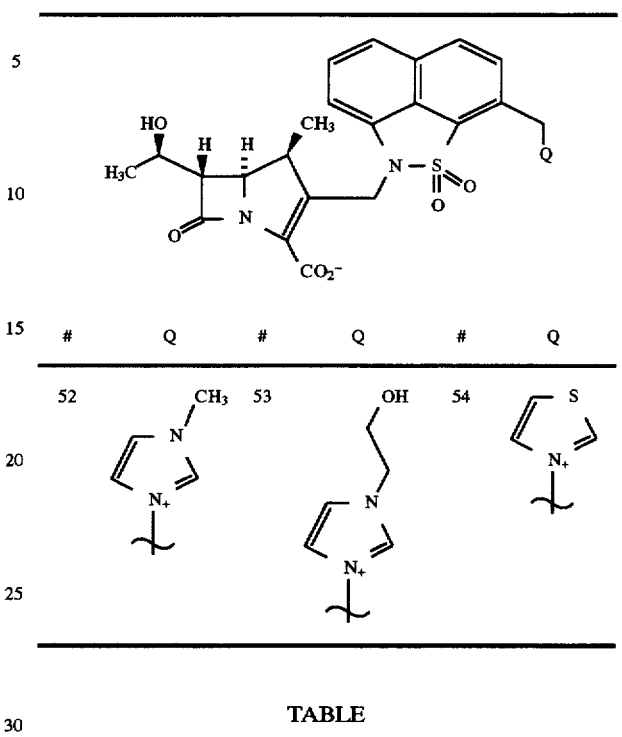
| # | Q | # | Q | # | Q |
|---|---|---|---|---|---|
| 52 | (N-methyl imidazolium) | 53 | (HO-ethyl imidazolium) | 54 | (S-thiazolium) |
TABLE
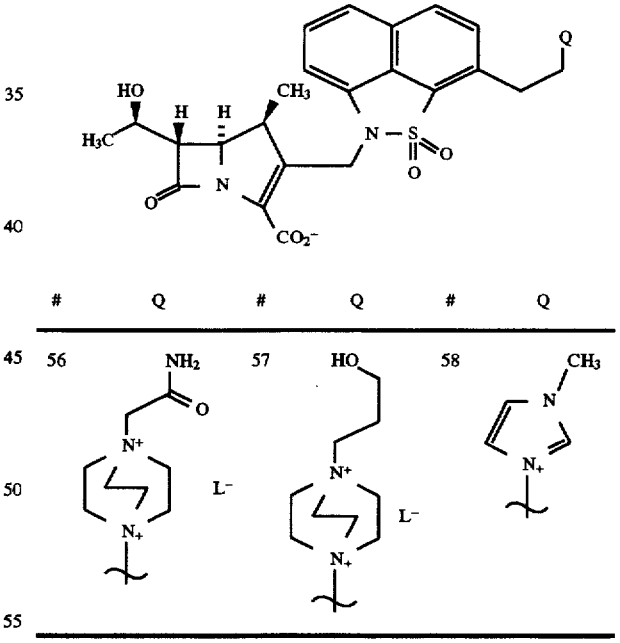
| # | Q | # | Q | # | Q |
|---|---|---|---|---|---|
| 56 | (NH₂ amide piperazinium) L⁻ | 57 | (HO-propyl piperazinium) L⁻ | 58 | (N-methyl imidazolium) |

TABLE
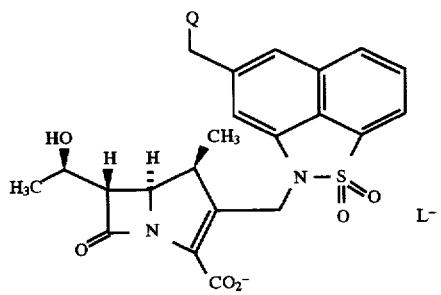
| # | Q | # | Q | # | Q |
|---|---|---|---|---|---|
| 60 | (NH2-C(=O)-CH2-N+ piperazinium) | 61 | (HO-CH2CH2CH2-N+ piperazinium) | 62 | (F-CH2CH2-N+ piperazinium) |
TABLE
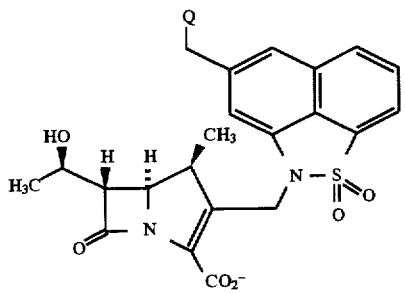
| # | Q | # | Q | # | Q |
|---|---|---|---|---|---|
| 63 | (N-methyl imidazolium) | 64 | (HO-CH2CH2- imidazolium) | 65 | (O=CH-N+ imidazolium) |
TABLE
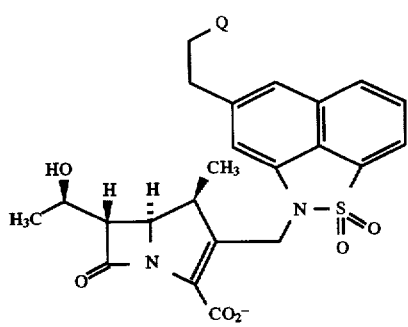
| # | Q | # | Q | # | Q |
|---|---|---|---|---|---|
| 67 | (NH2-C(=O)-CH2-N+ piperazinium) L− | 68 | (HO-CH2CH2CH2-N+ piperazinium) L− | 69 | (N-methyl imidazolium) |
TABLE
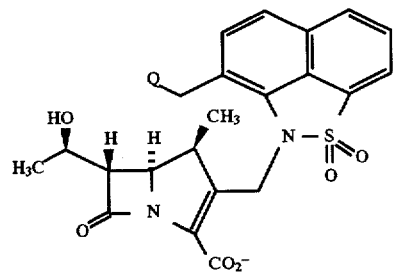
| # | Q | # | Q | # | Q |
|---|---|---|---|---|---|
| 74 | (N-methyl imidazolium) | 75 | (HO-CH2CH2- imidazolium) | 76 | (O=CH-N+ imidazolium) |

TABLE

| # | Q | # | Q | # | Q |
|---|---|---|---|---|---|
| 78 | (carboxamidomethyl-DABCO) L⁻ | 79 | (3-hydroxypropyl-DABCO) L⁻ | 80 | (N-methylimidazolium) |

TABLE

| # | Q | # | Q | # | Q |
|---|---|---|---|---|---|
| 82 | (carboxamidomethyl-DABCO) | 83 | (3-hydroxypropyl-DABCO) | 84 | (N-methylimidazolium) |

TABLE

| # | Q | # | Q | # | Q |
|---|---|---|---|---|---|
| 86 | (carboxamidomethyl-DABCO) | 87 | (3-hydroxypropyl-DABCO) | 88 | (N-methylimidazolium) |

TABLE

| # | Q | # | Q | # | Q |
|---|---|---|---|---|---|
| 90 | (carboxamidomethyl-DABCO) L⁻ | 91 | (3-hydroxypropyl-DABCO) L⁻ | 92 | (N-methylimidazolium) |

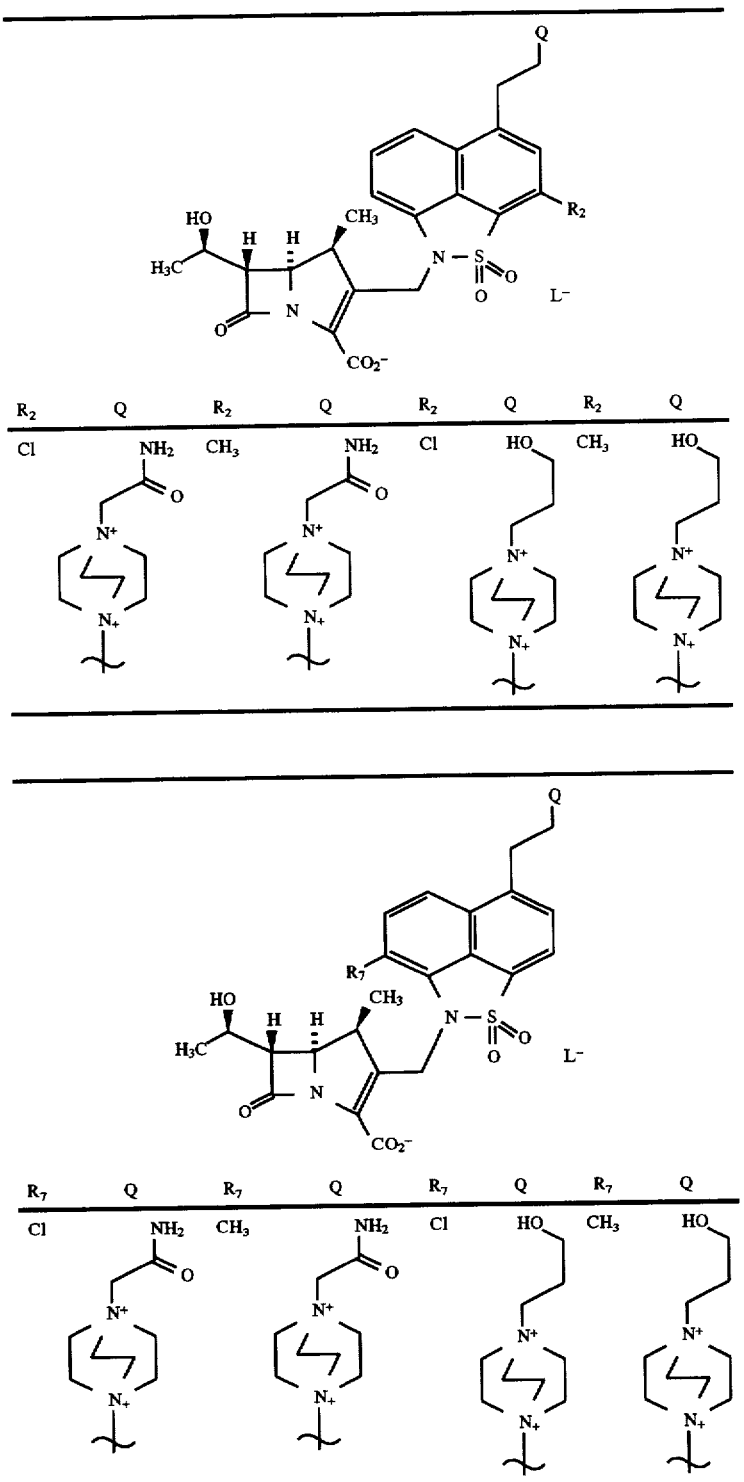

wherein Q is as defined in the tables and L⁻ represents a pharmaceutically acceptable counterion.

The compounds of the present invention are prepared by reacting a suitably protected, activated 2-hydroxymethyl-carbapen-2-em-3-carboxylate with a naphthosultam, modifying the thus-introduced side chain as desired, and then removing any protecting groups which are present to afford the desired final product. The process is illustrated by the following generic scheme:

FLOW SHEET A

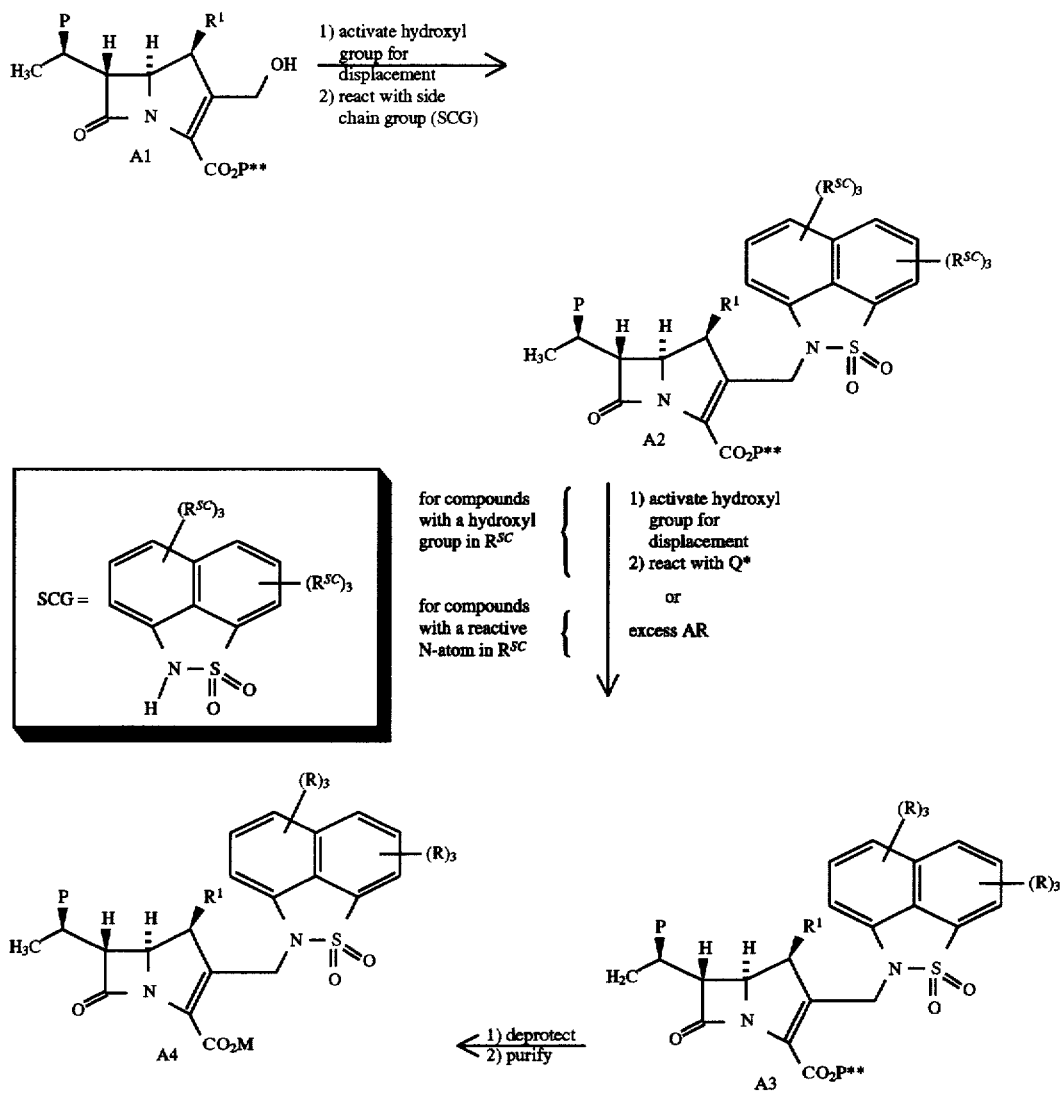

With reference to Flow Sheet A above, P, $R^1$, R, and M, are as defined with respect to the compounds of formula I. P** represents a carboxyl protecting group.

$R^{SC}$ represents a group which may or may not be selected from the group comprising R as defined above and is modified as necessary in the course of the synthesis of a compound of formula I to afford a member of that group, thus $R^{SC}$ may be viewed as a precursor for R.

Q* represents a group which reacts with intermediate A2 (upon activation of A2) in a manner which results in the incorporation in the final product of a member of the group defined as Q above, thus Q* may be viewed as a precursor for Q.

AR represents a suitable alkylating reagent, such as methyl iodide, methyl bromide, benzyl trichloroacetimidate, methyl trifluoromethanesulfonate, triethyloxonium tetrafluoroborate and the like.

The naphthosultam side chain group (SCG) used in the synthesis of the compounds of the present invention have, in some cases, been described in the chemical literature. In other cases, precursor compounds which may be readily converted to the requisite naphthosultam have been described in the literature. In cases where the requisite naphthosultam is not known in the literature it is neceessary to synthesize the naphthosultam by a newly developed synthesis. One skilled in the art can adapt a previously published synthesis of an analogous naphthosultam to prepare the requisite compound in a straightforward manner without undue experimentation. Numerous examples of naphthosultam synthesis are described herein (see below).

The naphthosultam side chain group (SCG) is initially reacted with a suitably protected carbapen-2-em-3-carboxylate having an activated hydroxymethyl group at the 2-position.

The carbapenem nucleus having a —$CH_2OH$ substituent at position 2 can be obtained in accordance with Schmitt, S. M. et al., *J. Antibiotics* 41(6): 780–787 (1988), the teachings of which are incorporated herein by reference. The carboxylic acid group at C-3 of the carbapenem is generally protected as a carboxyl protecting group such as p-nitrobenzyl (PNB), allyl, p-methoxybenzyl, trichloroethyl, 2-trimethylsilylethyl, and the like. Furthermore, the hydroxyl group of the 6-(hydroxyethyl) side-chain is optionally protected with a hydroxyl protecting group such as trimethylsilyl (TMS), triethylsilyl (TES), tertbutyldimethylsilyl (TBDMS), tert-butyldiphenylsilyl (TBDPS), acetyl, allyloxycarbonyl, 2-trimethylsilylethoxy carbonyl, 2-trichloroethoxycarbonyl and the like.

The addition of the naphthosultam side chain group (SCG) to the carbapenem is accomplished by treating a solution of the hydroxymethyl-carbapenem and the naphthosultam side chain group in a suitable solvent such as tetrahydrofuran (THF), ether, acetonitrile, dimethylformamide (DMF), benzene, dimethylsulfoxide (DMSO), and the like with a (premixed) suitable activating reagent such as diethyl azodicarboxylate (DEAD)/triphenylphosphine, diisopropyl azodicarboxylate (DIAD)/tributylphosphine, and the like, at a temperature between about −20° C. and 35° C. for about 5 to 90 minutes.

Alternatively, the naphthosultam and carbapenem can be mixed together with either the azodicarboxylate or the phosphine reagent in a suitable and the other component of the activating reagent (the phosphine or the azodicarboxylate, respectively) can be added to that mixture. Once the naphthosultam, carbapenem, and activating reagent(s) have been mixed, the reaction is allowed to proceed at a temperature between about −20° C. and 352° C. for about 5 to 90 minutes.

The resulting mixture is then subjected to a standard work-up procedure familiar to those skilled in the art to afford a crude 2-naphthosultam-methyl substituted carbapenem which is purified, if necessary, by recrystallization or by chromatography on silica gel, eluting with a suitable solvent or mixture of two or more solvents, such as hexane, ethyl acetate, ether, benzene, dichloromethane, chloroform, acetone, methanol and the like.

Modification of the naphthosultam side chain of compounds A2, which is generally necessary to introduce the charged substituent of A4, is best accomplished before removal of the protecting groups. For compounds which contain a hydroxyl group in the side chain, i.e. in $R^{SC}$, a positively charged substituent may be introduced into the side chain by first activating the hydroxyl group by converting it to a suitable leaving group such as a triflate, mesylate, tosylate, iodide, chloride, bromide, and the like, and then displacing the resulting leaving group with a compound Q*, such as N-methyl-imidazole, N-(2-hydroxyethyl)imidazole, N-methyl-diazabicyclooctane, 1-(carbamoylmethyl)-4-aza-1-azoniabicyclo-[2.2.2.]-octane, 1-(3-hydroxyprop-1-yl)-4-aza-1-azoniabicyclo-[2.2.2.]-octane, pyridine, morpholine and the like which contains a nitrogen atom that can act as a nucleophile. Alternatively, in some cases, the charged substituent may be incorporated in the naphthosultam side chain before addition of the naphthosultam to the carbapenem or may be introduced after deprotection of A2. However, introduction of the charged substituent by modification of A2 before deprotection is greatly preferred.

In some cases, activation of the hydroxyl group and displacement by Q* to produce A3 may be accomplished in a single step by taking advantage of the basic character of compound Q* and using it as a base in the activation reaction.

The conversion of the hydroxyl group to a suitable leaving group is accomplished by treating the hydroxyl substituted compound in a suitable solvent such as dichloromethane, tetrahydrofuran, ether, benzene, and the like with an activating reagent, such as trifluoromethanesulfonic anhydride, methanesulfonic anhydride, toluenesulfonic anhydride, methanesulfonyl chloride, benzenesulfonyl chloride, toluenesulfonyl chloride, and the like in the presence of a suitable base such as triethylamine, tributylamine, diisopropylethylamine, and the like at a temperature between about −100° C. and 0° C. for about 5 to 120 minutes. The intermediate thus obtained contains a leaving group, which may be converted to an alternative leaving group, iodide, by treating a solution of the intermediate in a suitable solvent such as acetone, methyl ethyl ketone, and the like at about −10° C. to 50° C. with an excess of sodium iodide or potassium iodide for about 0.25 to 24 hours.

In many cases, the iodide is obtained in sufficiently pure form that it may be used without further purification. For ease of handling, the iodide, if not crystalline, may be lyophilized from benzene afford an amorphous, easily handled, solid.

The activated hydroxyl group or iodide is displaced by reacting the activated intermediate with reagent Q*. In some cases, activation and displacement of the hydroxyl group may be accomplished in a single step. The activating reagent is added to a solution of the hydroxyl substituted compound in the presence of a suitable base in a suitable solvent such as dichloromethane, tetrahydrofuran, ether, DMF, benzene, acetonitrile, DMSO, and the like as described in the preceding paragraphs. The resulting activated intermediate is treated with 1–3 molar equivalents of compound Q* at a temperature between about −78° C. and 50° C. for about 15 to 120 minutes. In some cases, it is desirable to form the activated intermediate in one solvent, isolate the activated intermediate, and conduct the displacement reaction in a different solvent. In other cases, the displacement may be conducted without isolation of the intermediate and, in cases where Q* is also used as a base, may even be concurrent with the formation of the activated intermediate.

In cases where the displacement reaction is best accomplished by using the iodide, a solution of the iodide is combined with an approximately equivalent amount (0.9–1.05 molar equivalents) of compound Q*. A silver salt of a non-nucleophilic acid, such as silver trifluoromethanesulfonate, silver tetrafluoroborate and the like is then added. Although the reaction will proceed in the absence of the silver salt, the reaction proceeds more rapidly in the presence of the silver salt. In addition, the silver salt assists in the removal of the displaced iodide from the reaction mixture which can improve the efficiency of subsequent steps. The resulting mixture is then subjected to a standard work-up procedure familiar to those skilled in the art to afford a crude product which is purified, if necessary, by recrystallization or chromatography.

An alternative method for introducing a positive charge into the side chain may be applied to side chains (i.e. $R^{SC}$ groups) that contain a nitrogen atom which may be quaternized by reaction with a suitable alkylating reagent AR, such as methyl iodide, methyl bromide, benzyl trichloroacetimidate, methyl trifluoromethanesulfonate, triethyloxonium tetrafluoroborate, and the like. Quaternization of the nitrogen atom in the side chain is effected by treating a solution of the compound with a slight excess (1.05 to 1.2 molar equivalents) of the alkylating reagent.

The synthesis of the target compound is completed by removing any protecting groups which are present in the penultimate intermediate using standard techniques which are well known to those skilled in the art. The deprotected final product is then purified, as necessary, using standard techniques such as ion exchange chromatography, HPLC on reverse phase silica gel, MPLC on reverse phase polystyrene gel, and the like or by recrystallization.

The final product may be characterized structurally by standard techniques such as NMR, IR, MS, and UV. For ease of handling, the final product, if not crystalline, may be lyophilized from water to afford an amorphous, easily handled solid.

The compounds of the present invention are valuable antibacterial agents active against various Gram-positive and to a lesser extent Gram-negative bacteria, and accordingly find utility in human and veterinary medicine.

Many of compounds of the present invention are biologically active against MRSA/MRCNS. In vitro antibacterial activity is predictive of in vivo activity when the compounds are administered to a mammal infected with a susceptible bacterial organism.

Using standard susceptibility tests, the compounds of the invention are determined to be active against MRSA.

The compounds of the invention can be formulated in pharmaceutical compositions by combining the compound with a pharmaceutically acceptable carrier. Examples of such carriers are set forth below.

The compounds may be employed in powder or crystalline form, in liquid solution, or in suspension. They may be administered by a variety of means; those of principal interest include: topically, orally and parenterally by injection (intravenously or intramuscularly).

Compositions for injection, a preferred route of delivery, may be prepared in unit dosage form in ampules, or in multidose containers. The injectable compositions may take such forms as suspensions, solutions, or emulsions in oily or aqueous vehicles, and may contain various formulating agents. Alternatively, the active ingredient may be in powder (lyophillized or non-lyophillized) form for reconstitution at the time of delivery with a suitable vehicle, such as sterile water. In injectable compositions, the carrier is typically comprised of sterile water, saline or another injectable liquid, e.g., peanut oil for intramuscular injections. Also, various buffering agents, preservatives and the like can be included.

Topical applications may be formulated in carriers such as hydrophobic or hydrophilic bases to form ointments, creams, lotions, in aqueous, oleaginous or alcoholic liquids to form paints or in dry diluents to form powders.

Oral compositions may take such forms as tablets, capsules, oral suspensions and oral solutions. The oral composions may utilize carriers such as conventional formulating agents, and may include sustained release properties as well as rapid delivery forms.

The dosage to be administered depends to a large extent upon the condition and size of the subject being treated, the route and frequency of administration, the sensitivity of the pathogen to the particular compound selected, the virulence of the infection and other factors. Such matters, however, are left to the routine discretion of the physician according to principles of treatment well known in the antibacterial arts. Another factor influencing the precise dosage regimen, apart from the nature of the infection and peculiar identity of the individual being treated, is the molecular weight of the compound.

The compositions for human delivery per unit dosage, whether liquid or solid, may contain from about 0.01% to as high as about 99% of active material, the preferred range being from about 10–60%. The composition will generally contain from about 15 mg to about 2.5 g of the active ingredient; however, in general, it is preferable to employ dosage amounts in the range of from about 250 mg to 1000 mg. In parenteral administration, the unit dosage will typically include the pure compound in sterile water solution or in the form of a soluble powder intended for solution, which can be adjusted to neutral pH and isotonic.

The invention described herein also includes a method of treating a bacterial infection in a mammal in need of such treatment comprising administering to said mammal a compound of formula I in an amount effective to treat said infection.

The preferred methods of administration of the Formula I antibacterial compounds include oral and parenteral, e.g., i.v. infusion, i.v. bolus and i.m. injection.

For adults, about 5–50 mg of Formula I antibacterial compound per kg of body weight given one to four times daily is preferred. The preferred dosage is 250 mg to 1000 mg of the antibacterial given one to four times per day. More specifically, for mild infections a dose of about 250 mg two or three times daily is recommended. For moderate infections against highly susceptible gram positive organisms a dose of about 500 mg three or four times daily is recommended. For severe, life-threatening infections against organisms at the upper limits of sensitivity to the antibiotic, a dose of about 1000–2000 mg three to four times daily may be recommended.

For children, a dose of about 5–25 mg/kg of body weight given 2, 3, or 4 times per day is preferred; a dose of 10 mg/kg is typically recommended.

The compounds of Formula I are of the broad class known as carbapenems. Many carbapenems are susceptible to attack by a renal enzyme known as dehydropeptidase (DHP). This attack or degradation may reduce the efficacy of the carbapenem antibacterial agent. Many of the compounds of the present invention, on the other hand, are less subject to such attack, and therefore may not require the use of a DHP inhibitor. However, such use is optional and contemplated to be part of the present invention. Inhibitors of DHP and their use with carbapenems are disclosed in, e.g., [European Patent Application Nos. 79102616.4, filed Jul. 24, 1979 (Patent No. 0 007 614); and 82107174.3, filed Aug. 9, 1982 (Publication No. 0 072 014)].

The compounds of the present invention may, where DHP inhibition is desired or necessary, be combined or used with the appropriate DHP inhibitor as described in the aforesaid patents and published application. The cited European Patent Applications define the procedure for determining DHP susceptibility of the present carbapenems and disclose suitable inhibitors, combination compositions and methods of treatment. A preferred weight ratio of Formula I compound: DHP inhibitor in the combination compositions is about 1:1.

A preferred DHP inhibitor is 7-(L-2-amino-2-carboxyethylthio)-2-(2,2-dimethylcyclopropanecarboxamide)-2-heptenoic acid or a useful salt thereof.

The invention is further described in connection with the following non-limiting examples.

PREPARATIVE EXAMPLE 1

SYNTHESIS OF 5-(TRIMETHYLSILYLOXYMETHYL)-1,8-NAPHTHOSULTAM

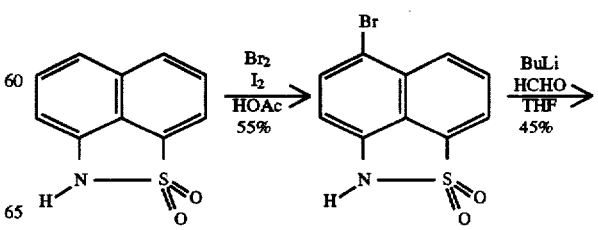

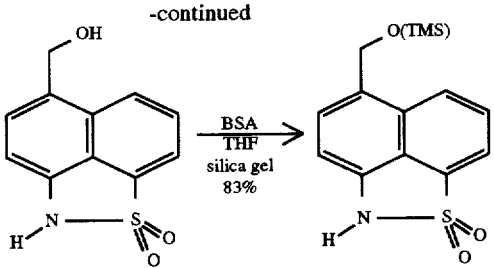

Step 1
5-Bromo-1,8-naphthosultam

A suspension of 1,8-naphthosultam (5 g, 24.4 mmol) in acetic acid (20 mL) was treated with a dark solution of iodine (6.5 g, 25.6 mmol) and bromine (1.3 mL, 25.2 mmol) in acetic acid (20 mL) over 10 minutes. The suspension was stirred an additional 95 minutes then placed in a 60° C. oil bath for 30 minutes. After cooling to room temperature, the mixture was added to a 1% aqueous $NaHSO_3$ solution (300 mL). The dark precipitate was filtered and dried overnight under a stream of nitrogen. The resulting solid (6 g) was dissolved in ethyl acetate then silica gel (ca. 6 g) was added and the mixture was evaporated under vacuum. The silica-adsorbed mixture was loaded onto a 4.5×30 cm silica column (silica gel 60) and was eluted with 5% ethyl acetate/ methylene chloride, collecting 25 mL fractions. Fractions 24–60 were combined and evaporated to give a green solid which was recrystallized from toluene to give the title compound as a light green solid (3.8 g).

$^1$H NMR ($CDCl_3$, 500 MHz) δ 6.82 (d, ArH), 6.83 (br.s, NH), 7.80 (d, ArH), 7.93 (t, ArH), 8.05 (d, ArH) and 8.38 (d, ArH).

Step 2
5-(hydroxymethyl)-1,8-naphthosultam

A solution of 5-bromo-1,8-naphthosultam (0.5 g, 1.76 mmol) in anhydrous tetrahydrofuran (10 mL) under nitrogen was cooled in a dry ice/acetone bath in a three neck flask. N-butyllithium (2.75 mL of a 1.6M solution in hexanes, 4.4 mmol) was added over 2 minutes and the suspension was stirred an additional 7 minutes. Paraformaldehyde (0.317 g, 10.6 mmol), placed in the bulb of a drying tube which was attached to the flask, was heated with a heat gun while a slow stream of nitrogen was blown over the solid. The generated formaldehyde was carried into the flask and the carrier gas vented through a line connected to a Firestone valve over a period of 13 minutes. After an additional 5 minutes, the mixture was removed from the bath and stirred for 10 minutes. Aqueous hydrochloric acid (3 mL of a 2N solution) was added and the clear suspension was stirred an additional 10 minutes. The mixture was partitioned between ethyl acetate (50 mL) and water (50 mL). The ethyl acetate layer was washed with saturated aqueous sodium chloride (20 mL), dried over magnesium sulfate, filtered, and evaporated. The solid residue (0.5 g) was dissolved in 5% methanol/ methylene chloride and was loaded onto a 24×4.5 cm silica gel column (silica gel 60, packed/loaded/eluted with 5% methanol/methylene chloride), collecting 8 mL fractions. Fractions 12–42 were combined and evaporated to give the title compound as a white solid (0.185 g).

$^1$H NMR (DMSO-$d_6$, 500 MHz) δ 4.85 (d, $CH_2OH$), 5.22 (t, $CH_2OH$), 6.82 (d, ArH), 7.52 (d, ArH), 7.83 (t, ArH), 8.13 (d, ArH) and 8.38 (d, ArH).

Step 3
5-(trimethylsilyloxymethyl)-1,8-naphthosultam

A solution of 5-(hydroxymethyl)-1,8-naphthosultam (0.185 g, 0.79 mmol) in tetrahydrofuran (1 mL) was treated with N,O-Bis(trimethylsilyl)acetamide ((BSA), 0.49 mL, 1.98 mmol). The mixture was stirred at room temperature for 1 hour then evaporated. The residual oil was dissolved in methylene chloride (1 mL) and was filtered through silica gel 60 (2.5 g), eluting the silica with additional methylene chloride (50 mL). The solvent was evaporated under vacuum and the residue was lyophilized from benzene (3 mL) to give the title compound as a white solid (0.20 g).

$^1$H NMR ($CDCl_3$, 500 MHz) δ 0.19 (s, $SiMe_3$), 5.07 (s, $CH_2$), 6.83 (d, ArH), 6.87 (br.s, NH), 7.50 (d, ArH), 7.78 (t, ArH), 7.95 (d, ArH) and 8.26 (d, ArH).

PREPARATIVE EXAMPLE 2

SYNTHESIS OF 5-(2-(TRIMETHYLSLYLOXY)-ETHYL)-1,8-NAPHTHOSULTAM

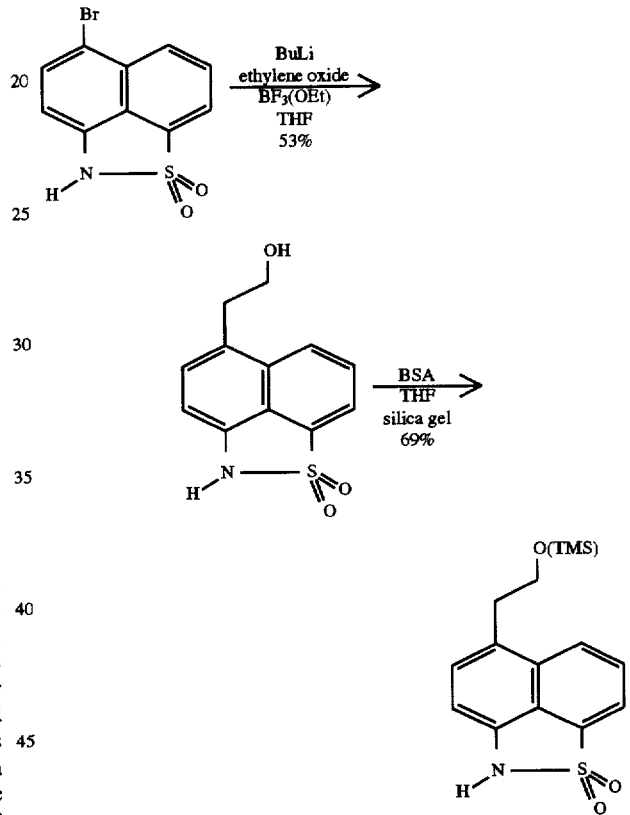

Step 1
5-(2-(hydroxy)-ethyl)-1,8-naphthosultam

A solution of 5-bromo-1,8-naphthosultam (0.6 g, 2.11 mmol) in anhydrous tetrahydrofuran (10 mL) under nitrogen was cooled in a dry ice/acetone bath. N-butyllithium (3.3 mL of a 1.6M solution in hexanes, 5.28 mmol) was added over 7 minutes and the suspension was stirred an additional 8 minutes. An excess of ethylene oxide was slowly bubbled into the mixture over 5 minutes. Boron trifluoride etherate (0.26 mL, 2.11 mmol) was then added over 5 minutes. After an additional 20 minutes, the reaction was quenched with the addition of acetic acid (0.35 mL, 6 mmol). The mixture was partitioned between ethyl acetate (100 mL) and water (100 mL). The ethyl acetate layer was washed with saturated aqueous sodium chloride (50 mL), dried over magnesium sulfate, filtered, and evaporated. The residual oil (0.7 g) was dissolved in 5% methanol/methylene chloride and was loaded onto a 24×2.75 cm silica gel column (silica gel 60, packed/loaded/eluted with 5% methanol/methylene chloride), collecting 8 mL fractions. Fractions 26–39 were combined and evaporated to give the title compound as an oil (0.28 g).

$^1$H NMR (DMSO-d$_6$, 500 MHz) δ 3.22 (t, CH$_2$Ar), 3.87 (t, CH$_2$OH), 6.79 (d, ArH), 7.35 (d, ArH), 7.74 (t, ArH), 7.91 (d, ArH) and 8.21 (d, ArH).

Step 2

5-(2-(trimethylsilyloxy)-ethyl)-1,8-naphthosultam

A solution of 5-(2-(hydroxy)-ethyl)-1,8-naphthosultam (0.09 g, 0.36 mmol) in tetrahydrofuran (1 mL) was treated with N,O-Bis(trimethylsilyl)acetamide (0.223 mL, 0.90 mmol). The mixture was stirred at room temperature for 20 minutes and was evaporated. The residual oil was dissolved in methylene chloride (3 mL) and was filtered through silica gel 60 (2.7 g), eluting the silica with additional methylene chloride (50 mL). The solvent was evaporated under vacuum and the residue was lyophilized from benzene (3 mL) to give the title compound as a white solid (0.08 g).

PREPARATIVE EXAMPLE 3

SYNTHESIS OF 4-(2-(TRIMETHYLSILYLOXY)-ETHYL)-1,8-NAPHTHOSULTAM

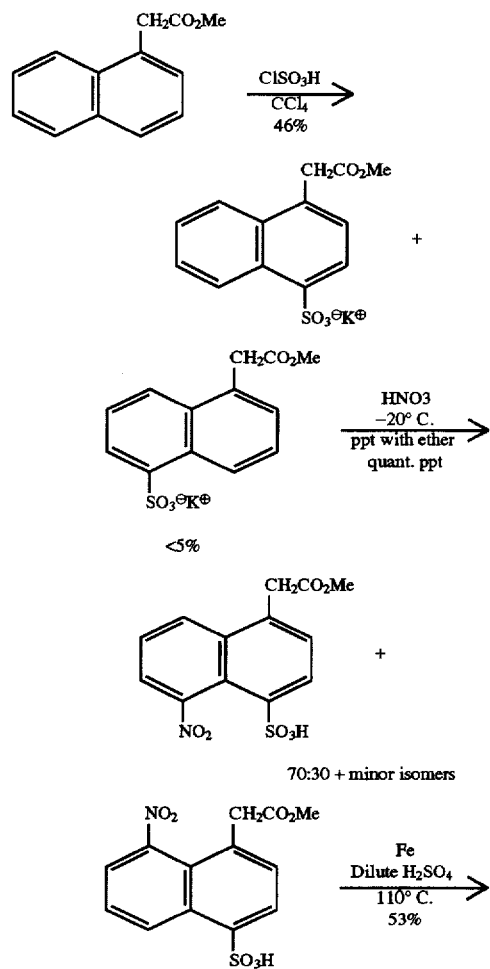

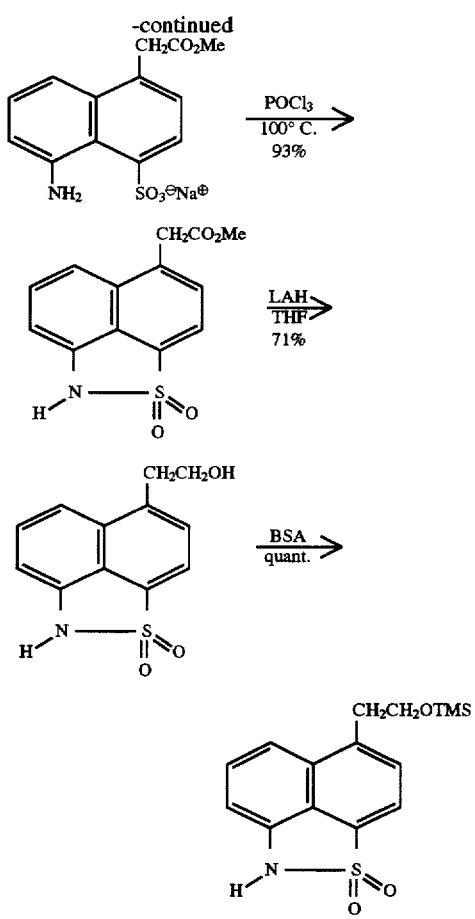

Step 1 potassium 1-(methoxycarbonylmethyl)-4-naphthalene sulfonate

A solution of methyl 1-naphthaleneacetate (1 mL, 5.77 mmol) in carbon tetrachloride (1 mL) was cooled under nitrogen in an ice bath. Chlorosulfonic acid (0.38 mL, 5.7 mmol) was added dropwise over 8 minutes. After an additional 30 minutes, the viscous mixture was removed from the bath and was stirred at room temperature for 17 hours to give a white solid. The solid was partitioned between methylene chloride (5 mL) and water (5 mL). After filtering through solka-floc, the methylene chloride layer was extracted with more water (2×5 mL), and the combined aqueous extracts were basified with potassium carbonate to give a precipitate. The suspension was concentrated to approximately 5 mL and was cooled in an ice bath. The suspension was then filtered and the collected solid was washed with cold water (2 mL). The solid was dried under a stream of nitrogen to give the title compound as a white solid (0.84 g).

$^1$H NMR (DMSO-d$_6$, 500 MHz) δ 3.73 (s, OMe), 4.27 (s, CH$_2$Ar), 7.53 (d, ArH), 7.71 (t, ArH), 7.76 (t, ArH), 8.06 (d, ArH), 8.10 (d, ArH) and 8.73 (d, ArH).

Step 2

1-(methoxycarbonymethyl)-5-nitro-4-naphthalene sulfonic acid

Potassium 1-(methoxycarbonylmethyl)-4-naphthalene sulfonate (10 g, 31.4 mmol) was added portionwise over 30 minutes to 90% nitric acid, which was cooled in a methanol/ice bath to approximately −15° C. After 2 hours, the bath temperature had reached −10° C. and diethyl ether (200 mL) was added to the mixture. The precipitated solid was filtered, washed with ether (100 mL) and isopropanol (20 mL), and dried under a stream of nitrogen to give the title compound as an approximately 70:30 mixture of the 5- and 8-nitro isomers (approximately 12 g).

$^1$H NMR (D$_2$O, 500 MHz) δ 3.69 (s, OMe), 4.30 (s, CH$_2$Ar), 7.67 (t, ArH), 7.71 (d, ArH), 8.18 (d, ArH), 8.29 (d, ArH) and 8.33 (d, ArH).

Step 3
sodium 1-(methoxycarbonylmethyl)-5-amino-4-naphthalene sulfonate 1-(methoxycarbonylmethyl)-5-nitro-4-naphthalene sulfonic acid (2 g, 6.15 mmol) was dissolved in water (20 mL), containing 0.5 mL concentrated sulfuric acid, and was added dropwise over 5 minutes to a refluxing suspension of iron (4 g, 71.6 mmol) in water (100 mL). After refluxing for one hour, the dark mixture was cooled to room temperature, made basic with sodium carbonate, and concentrated to approximately 30 mL. The residual mixture was placed on a CG-161 amberchrom resin column (2.5×30 cm). The column was washed with water (200 mL), 10% MeCN/H$_2$O (200 mL), and 25% MeCN/H$_2$O (400 mL), collecting 25 mL fractions. Fractions 21–28 were combined and evaporated to give the title compound as a dark solid (0.675 g).

$^1$H NMR (D$_2$O, 500 MHz) δ 3.64 (s, OMe), 4.18 (s, CH$_2$Ar), 7.04 (d, ArH), 7.38 (d, ArH), 7.41 (d, ArH), 7.45 (t, ArH) and 8.22 (d, ArH).

Step 4
4-(methoxycarbonylmethyl)-1,8-naphthosultam

Sodium 1-(methoxycarbonylnethyl)-5-amino-4-naphthalene sulfonate (0.675 g, 2.13 mmol) was suspended in phosphorous oxychloride (10 g, 65.2 mmol) and was refluxed for 1 hour to give a thin suspension. The mixture was cooled to room temperature and was partitioned between ethyl acetate (100 mL) and water (100 mL). The water layer was extracted with ethyl acetate (50 mL) and the combined ethyl acetate layers were washed with saturated aqueous sodium chloride (100 mL), dried over magnesium sulfate, filtered and evaporated to give the title compound as a solid (0.55 g).

$^1$H NMR (CDCl$_3$, 500 MHz) δ 3.72 (s, OMe), 4.15 (s, CH$_2$Ar), 6.86 (br s, NH), 6.97 (d, ArH), 7.60 (t, ArH), 7.67 (d, ArH), 7.71 (d, ArH) and 7.95 (d, ArH).

Step 5
4-(2-(hydroxy)-ethyl)-1,8-naphthosultam

A solution of 4-(methoxycarbonylmethyl)-1,8-naphthosultam (0.2 g, 0.72 mmol) in tetrahydrofuran (2 mL) was cooled under nitrogen in an ice bath. Lithium aluminum hydride (1.44 mL of a 1.0M solution in THF, 1.44 mmol) was added over 1 minute to give a light yellow suspension. After 30 minutes, water was carefully added and the mixture was partitioned between ethyl acetate (30 mL) and 1N hydrochloric acid (10 mL). The aqueous layer was extracted with ethyl acetate (50 mL) and the combined ethyl acetate layers were washed with saturated aqueous sodium chloride (10 mL), dried over magnesium sulfate, filtered and evaporated. The residual solid (0.16 g) was purified by preparative thin layer chromatography (2×1000 micron silica gel plates, developed/eluted with 5% MeOH/CH$_2$Cl$_2$) to give the title compound as a solid (0.127 g).

$^1$H NMR (0.14 mL CDCl$_3$ and 0.01 mL CD$_3$OD, 500 MHz) δ 3.33 (t, CH$_2$Ar), 3.91 (t, CH$_2$OH), 6.84 (d, ArH), 7.49 (dd, ArH), 7.59 (d, ArH), 7.59 (d, ArH) and 7.83 (d, ArH).

Step 6
4-(2-(trirmethylsilyloxy)-ethyl)-1,8-naphthosultam

N,O-Bistrimethylsilylacetamide (0.31 mL, 1.25 mmol) was added to a solution of 4-(2-(hydroxy)-ethyl)-1,8-naphthosultam (0.125 g, 0.50 mmol) in tetrahydrofuran (1 mL). After one hour the mixture was evaporated and the residue was dissolved in methylene chloride (2 mL) and filtered through silica gel (2.5 g). The silica gel was eluted with methylene chloride (50 mL), the solvent was evaporated and the residue was lyophilized from benzene (3 mL) to give the title compound as an oil (0.16 g, quant.).

$^1$H NMR (CDCl$_3$, 500 MHz) δ 0.035 (s, TMS), 3.37 (t, CH$_2$Ar), 3.94 (t, CH$_2$O(TMS)), 6.95 (d, ArH), 7.56 (dd, ArH), 7.64 (d, ArH), 7.71 (d, ArH) and 7.92 (d, ArH).

PREPARATIVE EXAMPLE 4

SYNTHESIS OF 4-(TRIMETHYLSILYLOXYMETHYL)-1,8-NAPHTHOSULTAM

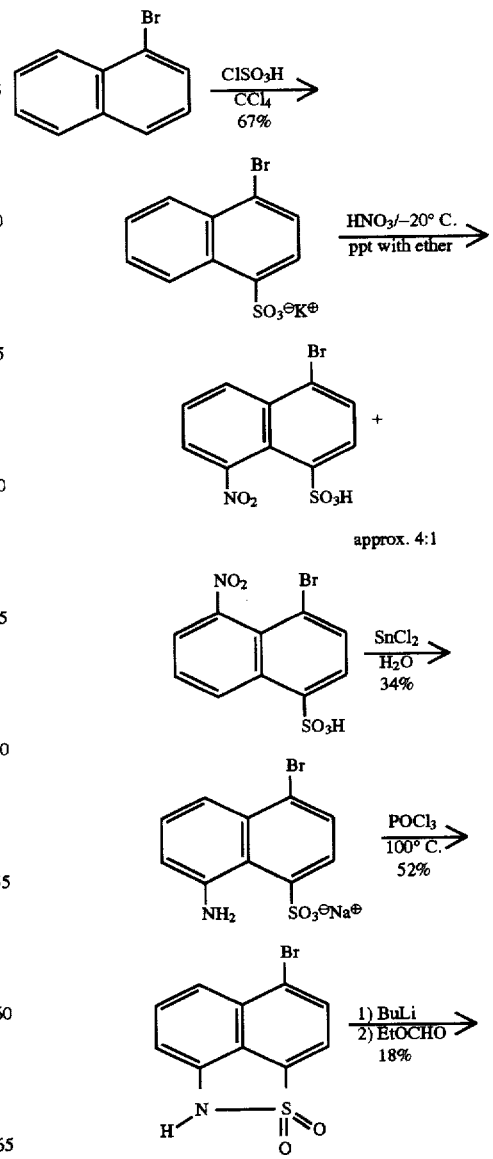

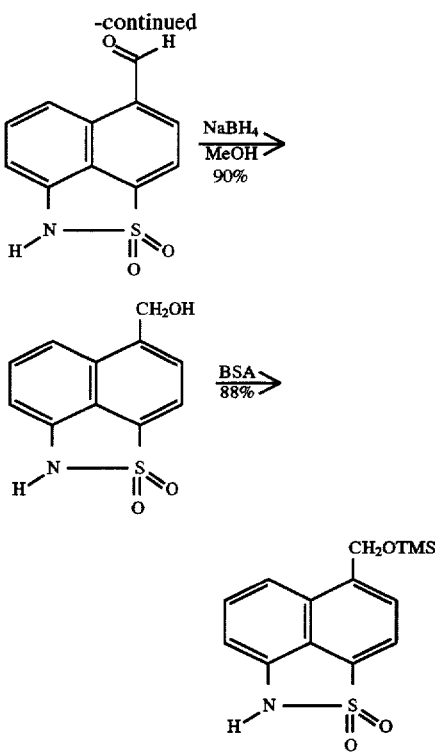

Step 1
potassium 1-bromo-4-naphthalenesulfonate

A solution of 1-bromonaphthalene (19 mL, 137 mmol) in carbon tetrachloride (24 mL) was cooled in an ice bath under nitrogen.

Chlorosulfonic acid (9.1 mL, 137 mmol) was added dropwise over 20 minutes. After an additional 5 minutes, the heavy grey suspension was removed from the ice bath and was stirred at room temperature for 16 hours to give a grey paste. The mixture was partitioned between methylene chloride (100 mL) and water (300 mL). The aqueous layer was made basic with potassium carbonate and the resulting suspension was filtered. The collected solid was washed with methylene chloride (50 mL) and water (50 mL), and dried under vacuum to give the title compound as a white solid (30 g, 67%).

$^1$H NMR (DMSO-$d_6$, 500 MHz) δ 7.61 (m, ArH), 7.65 (m, ArH), 7.82 (m, 2ArH), 8.14 (dd, ArH), and 8.90 (dd, ArH).

Step 2
1-bromo-5-nitro-4-naphthalene sulfonic acid

Potassium 1-bromo-4-naphthalenesulfonate (1.38 g, 4.24 mmol) was added portionwise over 20 minutes to 90% nitric acid (2 mL), which was cooled in a methanol/ice bath to approximately −15° C. After 1.5 hours, the mixture was placed in a refrigerator for 20 hours. Diethyl ether (20 mL) was added and the precipitated solid was filtered, washed with ether (100 mL) and isopropanol (20 mL), and dried under a stream of nitrogen to give the title compound as an approximately 4:1 mixture of the 5- and 8-nitro isomers (1.25 g).

$^1$H NMR (D$_2$O, 500 MHz) δ 7.70 (dd, ArH), 8.09 (d, ArH), 8.20 (d, ArH), 8.21 (dd, ArH), and 8.63 (d, ArH).

Step 3
sodium 1-bromo-5-amino-4-naphthalenesulfonate

1-Bromo-5-nitro-4-naphthalenesulfonate (1 g, 3.01 mmol) and tin chloride dihydrate (1.83 g, 8.1 mmol) were suspended in a mixture of water (10 mL) and ethanol (10 mL). The resulting mixture was heated for 3 hours in a 100° C. oil bath. The mixture was cooled to room temperature and filtered. The collected solid was suspended in water (20 mL) and the mixture was made basic with sodium carbonate then placed on a CG-161 amberchrom resin column (3×9 cm). The column was washed with water (300 mL) and was eluted with 25% MeCN/H$_2$O, collecting 12 mL fractions. Fractions 17–19 were combined and evaporated to give the title compound as a solid (0.33 g).

$^1$H NMR (D$_2$O, 500 MHz) δ 7.07 (dd, ArH), 7.49 (t, ArH), 7.83 (d, ArH), 7.85 (dd ArH) and 8.08 (d, ArH).

Step 4
4-bromo-1,8-naphthosultam

Sodium 1-bromo-5-amino-4-naphthalenesulfonate (1.2 g, 3.70 mmol) was suspended in phosphorous oxychloride (10 mL, 107 mmol) and the mixture was refluxed for 1 hour to give a thin suspension. The mixture was cooled to room temperature and was added to ice (100 mL). The precipitate was collected and washed with water (20 mL) then dried under vacuum (0.675 g). A second crop was obtained from the filtrate (0.186 g). The combined solids were dissolved in 5% methanol in methylene chloride and were placed on a silica gel column (29×3.5 cm, packed and eluted with 5% methanol in methylene chloride), collecting 8 mL fractions. Fractions 27–39 were combined and evaporated to give the title compound as a solid (0.55 g).

$^1$H NMR (0.14 mL CDCl$_3$ and 0.01 mL CD$_3$OD, 500 MHz) δ 6.89 (d, ArH), 7.58 (dd ArH), 7.68 (d, ArH), 7.73 (d, ArH) and 7.95 (d, ArH).

Step 5
4-formyl-1,8-naphthosultam

A solution of 4-bromo-1,8-naphthosultam (0.24 g, 0.845 mmol) in anhydrous tetrahydrofuran (5 mL) was cooled in a dry ice/acetone bath under nitrogen. n-Butyllithium (1.32 mL of a 1.6M solution in hexanes, 2.11 mmol) was added and the mixture was stirred for 5 minutes. Ethyl formate (1 mL, 12.4 mmol) was then added, and after an additional 5 minutes, 2N aqueous hydrochloric acid (3 mL) was added. The flask was removed from the bath and the yellow solution was partitioned between ethyl acetate (30 mL) and water (30 mL). The ethyl acetate layer was washed with saturated aqueous sodium chloride (20 mL), dried over magnesium sulfate, filtered, and evaporated. The residual oil was purified on preparative silica gel plates (3×1000 micron/ developed and eluted with 5% methanol/methylene chloride) to give the title compound as a red solid (0.035 g).

$^1$H NMR (CDCl$_3$, 500 MHz) δ 7.09 (d, ArH), 7.78 (dd, ArH), 8.12 (d, ArH), 8.30 (d, ArH), 8.70 (d, ArH) and 10.5 (s, CHO).

Step 6
4-(hydroxymethyl)-1,8-naphthosultam

A solution of 4-formyl-1,8-naphthosultam (0.035 g, 0.15 mmol) in anhydrous methanol (1 mL) was cooled in an ice bath under nitrogen. Sodium borohydride (0.011 g, 0.3 mmol) was added and the solution was stirred for 30 minutes. The mixture was partitioned between methylene chloride (10 mL) and 0.2N aqueous hydrochloric acid (10 mL). The aqueous layer was extracted with 5% methanol in methylene chloride (2×10 mL), and the combined organic layers were evaporated to give the title compound as a yellow solid (0.032 g).

$^1$H NMR (0.14 mL CDCl$_3$ and 0.01 mL CD$_3$OD, 500 MHz) δ 5.13 (s, CH$_2$OH), 6.85 (d, ArH), 7.50 (dd, ArH), 7.57 (d, ArH), 7.82 (d, ArH) and 7.88 (d, ArH).

Step 7
4-(trimethylsilyloxymethyl)-1,8-naphthosultam

A solution of 4-(hydroxymethyl)-1,8-naphthosultam (0.032 g, 0.136 mmol) in tetrahydrofuran (0.5 mL) was treated with N,O-Bis(trimethylsilyl)acetamide (0.084 mL, 0.34 mmol). The mixture was stirred at room temperature for 45 The residua was evaporated. The residual oil was dissolved in methylene chloride (1 mL) and was filtered through silica gel 60 (1 g), eluting the silica with additional methylene chloride (50 mL). The solvent was evaporated under vacuum and the residue was lyophilized from benzene (3 mL) to give the title compound as a white solid (0.037 g).

$^1$H NMR (CDCl$_3$, 500 MHz) δ 0.23 (s, SiMe$_3$), 6.78 (brs, NH), 5.23 (s, CH$_2$), 6.97 (d, ArH), 7.58 (dd, ArH), 7.64 (d, ArH), 7.90 (d, ArH) and 7.97 (d, ArH).

PREPARATIVE EXAMPLE 5

SYNTHESIS OF 4-(3-TRIMETHYLSILYLOXYPROP-1-YL)-1,8-NAPHTHOSULTAM

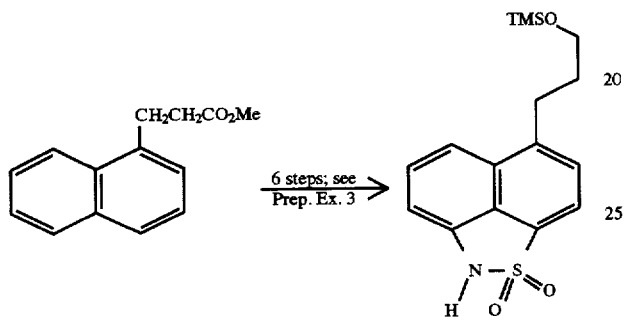

Steps 1–6

Synthesis of 4-(3-trimethylsilyloxyprop-1-yl)-1,8-naphthosultam

By substitution of methyl 1-naphthalenepropionate for methyl 1-naphthaleneacetate in the procedure of Preparative Example 3, 4-(3-trimethylsilyloxyprop-1-yl)-1,8-naphthosultam is prepared.

EXAMPLE 1

SYNTHESIS OF (1S,5R,6S)-2-(5-((CARBAMOYLMETHYL)-1,4-DIAZONIABICYCLO[2.2.2]OCT-1-YL)METHYL)(1,8-NAPHTHOSULTAM)METHYL)-6-[1(R)-HYDROXYETHYL]-1-METHYLCARBAPEN-2-EM-3-CARBOXYLATE CHLORIDE

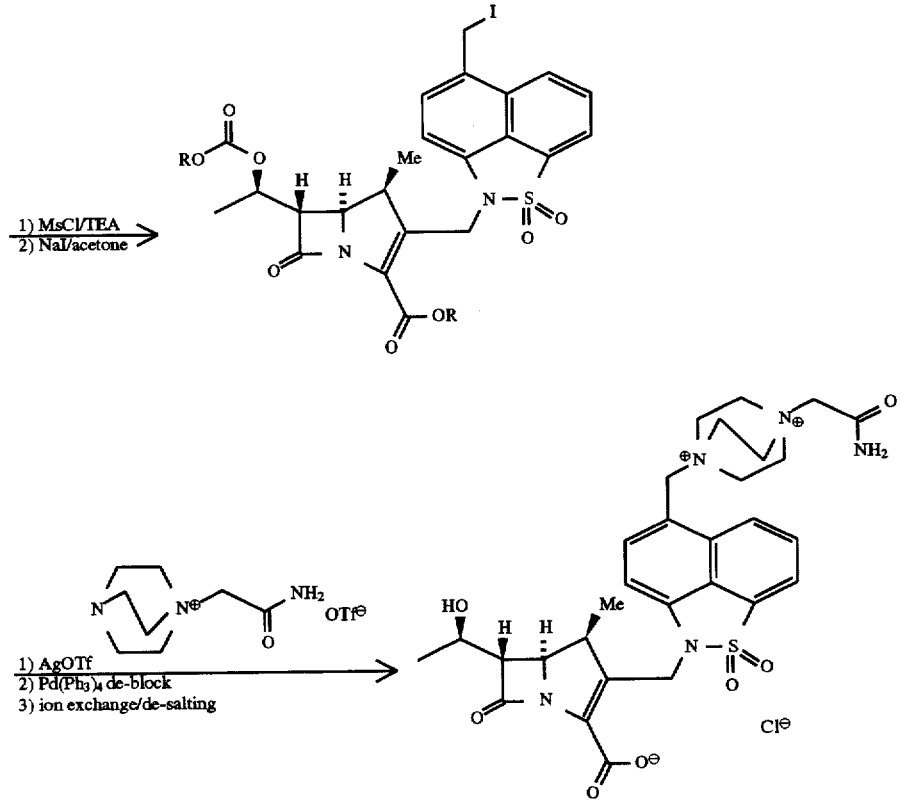

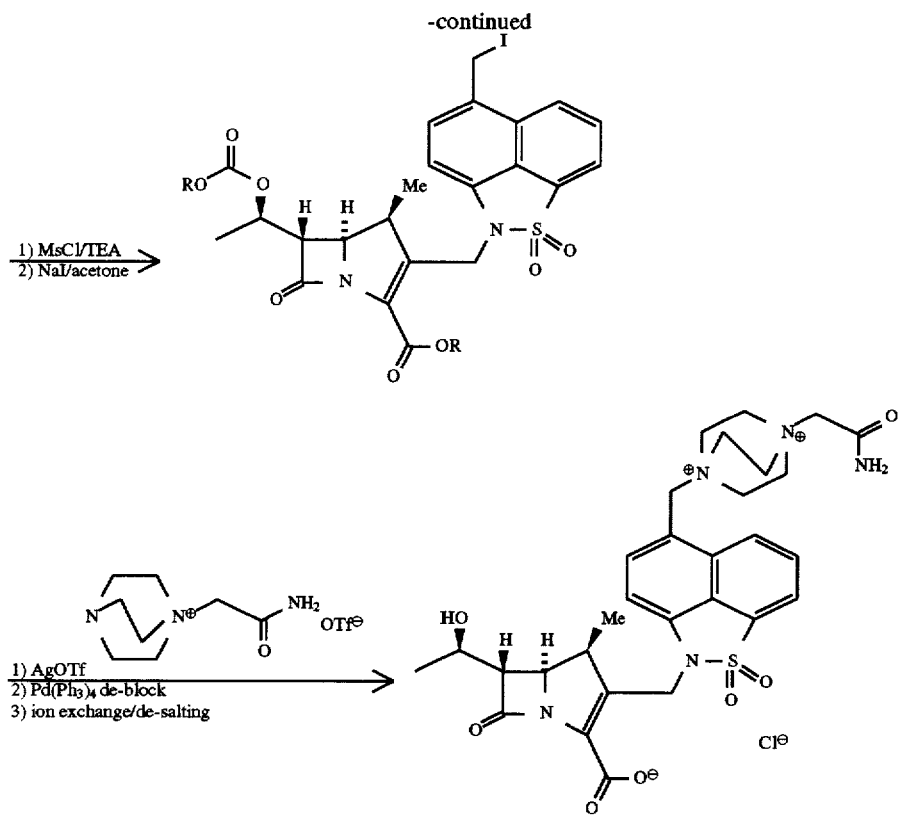

Step 1
allyl(1S,5R,6S)-2-(5-(trimethylsilyloxymethyl-1,8-naphthosultam)methyl)-6-[1(R)-(allyloxycarbonyl)oxyethyl]-1-methylcarbapen-2-em-3-carboxylate To a solution of allyl(1S,5R,6S)-2-(hydroxymethyl)-6-[1(R)-(allyloxycarbonyl)oxyethyl]-1-methylcarbapen-2-em-3-carboxylate (0.09 g, 0.246 mmol), 5-(trimethylsilyloxymethyl)-1,8-naphthosultam (0.076 g, 0.246 mmol) and triphenylphosphine (0.097 g, 0.369 mmol) in tetrahydrofuran (1.5 mL), cooled in an ice bath, was added diethylazodicarboxylate (DEAD) (0.058 mL, 0.369 mmol). After 25 minutes the mixture was partitioned between ethyl acetate (20 mL) and water (20 mL). The water layer was extracted with ethyl acetate (10 mL) and the combined ethyl acetate layers were washed with saturated aqueous sodium chloride (20 mL), dried with magnesium sulfate, filtered, and evaporated. The residual oil was purified by preparative thin layer chromatography (3×1000 micron silica gel plates, developed/eluted with 5% EtOAc/$CH_2Cl_2$) to give the title compound as an oil (0.134 g).

$^1$H NMR ($CDCl_3$, 500 MHz) δ 0.18 (s, TMS), 1.31 (d, 1-$CH_3$), 1.46 (d, $CH_3CHO(ALLOC)$), 3.38 (dq, H-1), 3.45 (dd, H-6), 4.17 (dd, H-5), 4.60 and 4.89 (2 m's, 2$CH_2$vinyl), 5.07 (s, $CH_2O$), 5.13 (dq, H-8), 5.26, 5.34, 5.36 and 5.53 (4 m's, 4 vinyl H's), 4.68 and 5.39 (2d's, $CH_2N$), 5.91 and 6.05 (2m's, 2$CH_2$vinyl), 6.67 (d, ArH), 7.49 (d, ArH), 7.83 (dd, ArH), 8.02 (d, ArH) and 8.33 (d, ArH).

Step 2
allyl(1S,5R,6S)-2-(5-(hydroxymethyl-1,8-naphthosultam)methyl)-6-[1(R)-(allyloxycarbonyl)oxyethyl]-1-methylcarbapen-2-em-3-carboxylate To a solution of allyl(1S,5R,6S)-2-(5-(trimethylsilyloxymethyl-1,8-naphthosultam)methyl)-6-[1(R)-(allyloxycarbonyl)oxyethyl]-1-methylcarbapen-2-em-3-carboxylate (0.068 g, 0.104 mmol) in a mixture of tetrahydrofuran (1 mL) and water (0.5 mL), was added 1N aqueous trifluoromethane sulfonic acid (0.02 mL, 0.02 mmol). After 5 minutes the mixture was partitioned between methylene chloride (5 mL) and 5% aqueous bicarbonate (5 mL). The water layer was extracted with methylene chloride (5 mL) and the combined methylene chloride layers were dried with magnesium sulfate, filtered and evaporated to give the title compound as an oil (0.06 g, quant).

$^1$H NMR ($CDCl_3$, 500 MHz) δ 1.31 (d, 1-$CH_3$), 1.45 (d, $CH_3CHO(ALLOC)$), 3.38 (dq, H-1), 3.45 (dd, H-6), 4.16 (dd, H-5), 4.59 and 4.89 (2m's, 2$CH_2$vinyl), 5.08 (m, $CH_2O$), 5.13 (dq, H-8), 5.26, 5.34, 5.36 and 5.53 (4m's, 4 vinyl H's), 4.68 and 5.41 (2d's, $CH_2N$), 5.91 and 6.05 (2m's, 2$CH_2$vinyl), 6.67 (d, ArH), 7.50 (d, ArH), 7.85 (dd, ArH), 8.03 (d, ArH) and 8.41 (d, ArH).

Step 3
allyl(1S,5R,6S)-2-(5-(iodomethyl-1,8-naphthosultam)methyl)-6-[1(R)-(allyloxycarbonyl)oxyethyl]-1-methylcarbapen-2-em-3-carboxylate To a solution of allyl(1S,5R,6S)-2-(5-(hydroxymethyl-1,8-naphthosultam)methyl)-6-[1(R)-(allyloxycarbonyl)oxyethyl]-1-methylcarbapen-2-em-3-carboxylate (0.12 g, 0.206 mmol) in dichloromethane (4 mL), cooled in an ice bath under nitrogen, was added triethylamine (0.05 mL, 0.361 mmol) followed by methane sulfonyl chloride (0.024 mL, 0.31 mmol). After 20 minutes, additonal triethylamine (0.025 mL, 0.18 mmol) and methane sulfonyl chloride (0.012 mL, 0.16 mmol) were added. After an additional 50 minutes, still more triethylamine (0.05mL, 0.36 mmol) and methane sulfonyl chloride (0.024 mL, 0.31 mmol) were added. After a total of 90 minutes the mixture was partitioned between methylene chloride (30 mL) and 0.1N aqueous hydrochloric acid (20 mL). The methylene chloride layer was washed with water (80 mL), dried over magnesium sulfate and evaporated. Examination of the residual oil by $^1$H NMR showed mostly the chloromethyl derivative, with a trace of the expected mesylate. (The tlc, 5% ethyl acetate/methylene chloride, of the mesylate and the starting alcohol are almost identical, apprx. R$_f$ of 0.2, with the chloromethyl derivative at approximately 0.5. The addition of the excess reagents was therefore unnecessary). The oil was dissolved in acetone (3 mL) then sodium iodide (0.093 g, 0.618 mmol) was added and the mixture was stirred at room temperature for 3 hours. The reaction mixture was partitioned between methylene chloride (20 mL) and water (20 mL), the methylene chloride layer was washed with 5% aqueous NaHSO$_3$, dried over magnesium sulfate, filtered and evaporated. The residual oil was lyophilized from benzene (3 mL) to give the title compound as a foam (0.132 g)

$^1$H NMR (CDCl$_3$, 500 MHz) δ 1.30 (d, 1-CH$_3$), 1.42 (d, CH$_3$CHO(ALLOC)), 3.40 (dq, H-1), 3.43 (dd, H-6), 4.18 (dd, H-5), 4.59 and 4.89 (2m's, 2CH$_2$vinyl), 4.88 (m, CH$_2$O), 5.15 (dq, H-8), 5.26, 5.34, 5.36 and 5.53 (4m's, 4 vinyl H's), 4.65 and 5.55 (2d's, CH$_2$N), 5.91 and 6.05 (2m's, 2CH$_2$vinyl), 6.60 (d, ArH), 7.60 (d, ArH), 7.95 (dd, ArH), 8.03 (d, ArH) and 8.37 (d, ArH).

Step 4

(1S,5R,6S)-2-(5-(((carbamoylmethyl)-1,4-diazoniabicyclo[2.2.2]oct-1-yl)methyl)(1,8-naphthosultam)methyl)-6-[1(R)-hydroxyethyl]-1-methylcarbapen-2-em-3-carboxylate chloride To a solution of allyl(1S,5R,6S)-2-(5-(iodomethyl-1,8-naphthosultam)methyl)-6-[1(R)-(allyloxycarbonyl)oxyethyl]-1-methylcarbapen-2-em-3-carboxylate (0.025 g, 0.036 mmol) in acetonitrile (0.3 mL) was added 1-carbamoylmethyl-4-aza-1-azoniabicyclo[2.2.2]-octane trifluoromethane sulfonate (0.012 g, 0.036 mmol) and silver trifluoromethane sulfonate (0.036 mL of a 1.0M solution in acetonitrile, 0.036 mmol). The suspension was stirred for 40 minutes at room temperature, filtered and evaporated. The residual oil was dissolved in dimethylformamide (0.5 mL). The solution was cooled in an ice bath and 0.5M sodium ethyl hexanoate in ethyl acetate (0.08 mL, 0.04 mmol) and ethyl hexanoic acid (0.006 mL, 0.04 mmol) were added. The solution was blanketed with nitrogen, using a Firestone valve, and triphenylphosphine (0.003 g, 0.012 mmol) and tetrakis(triphenylphosphine)palladium (0.014 g, 0.012 mmol) were added. After one hour, diethyl ether (5 mL) was added and the supernatant was decanted from the precipitate. The solid was washed with additional diethyl ether (5 mL) and was dried under vacuum. The solid was dissolved in 1:1 acetonitrile/water (3 mL) and was loaded onto a Bio-Rad weak cation exchange resin (3 mL, macroprep cm ion exchange resin, sodium cycle). The column was washed with 1:1 acetonitrile/water (2 mL) and water (12 mL). The column was then eluted with 5% aqueous sodium chloride, collecting 3 mL fractions. Fractions 1–5 were cooled in an ice bath and were then loaded onto an amberchrom CG-161 resin (3 mL). The column was washed with cold de-ionized water (20 mL) and was eluted with 20% isopropanol in water, collecting 4 mL fractions. Fractions 1–4 were combined and concentrated to approximately 1 mL which was lyophilized to give the title compound (0.005 g).

$^1$H NMR (D$_2$O, 500 MHz) δ 1.16 (d, 1-CH$_3$), 1.21 (d, CH$_3$CHOH), 3.10 (dq, H-1), 3.42 (dd, H-6), 4.03 (dd, H-5), 4.18 (dq, H-8), 4.05 and 4.20 (2m, NCH$_2$CH$_2$N), 4.36 (s, CH$_2$CONH$_2$), 4.63 and 5.25 (2d's, CH$_2$N), 5.20 (s, ArCH$_2$), 6.89 (d, ArH), 7.78 (d ArH), 7.99 (dd, ArH), 8.13 (d, ArH) and 8.40 (d, ArH).

EXAMPLE 2

SYNTHESIS OF (1S,5R,6S)-2-(5-(((3-HYDROXYPROP-1-YL)-1,4-DIAZONIABICYCLO[2.2.2]OCT-1-YL)METHYL)(1,8-NAPHTHOSULTAM)METHYL)-6-[1(R)-HYDROXYETHYL]-1-METHYLCARBAPEN-2-EM-3-CARBOXYLATE CHLORIDE

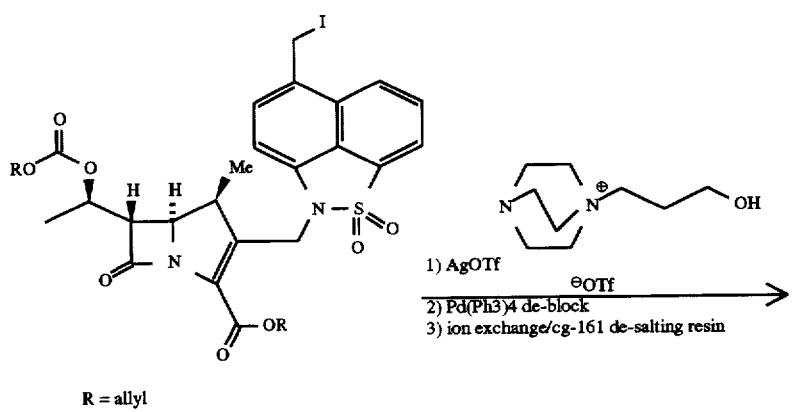

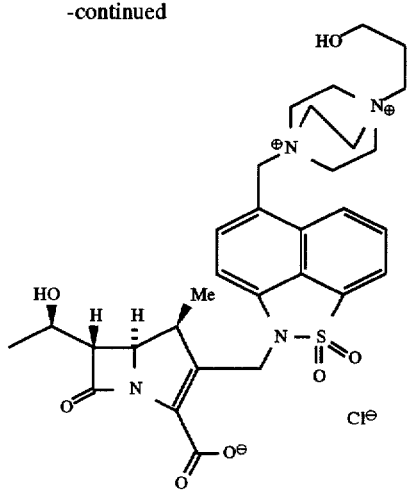

To a solution of allyl(1S,5R,6S)-2-(5-(iodomethyl-1,8-naphthosultam)methyl)-6-[1(R)-(allyloxycarbonyl)oxyethyl]-1-methylcarbapen-2-em-3-carboxylate (0.035 g, 0.051 mmol) in acetonitrile (0.3 mL) was added 1-(3-hydroxypropyl)-4-aza-1-azoniabicyclo[2.2.2]octane trifluoromethane sulfonate (0.018 g, 0.056 mmol) and silver trifluoromethane sulfonate (0.05 mL of a 1.0M solution in acetonitrile, 0.05 mmol). The suspension was stirred for 45 minutes at room temperature, filtered and evaporated. The residual oil was dissolved in dimethylformamide (0.5 mL). The resulting solution was cooled in an ice bath and 0.5M sodium ethyl hexanoate in ethyl acetate (0.08 mL, 0.04 mmol) and ethyl hexanoic acid (0.006 mL, 0.04 mmol) were added. The solution was blanketed with nitrogen, using a Firestone valve, and triphenylphosphine (0.003 g, 0.012 mmol) and tetrakis(triphenylphosphine)palladium (0.014 g, 0.012 mmol) were added. After one hour, diethyl ether (4 mL) was added and the supernatant was decanted from the precipitate. The solid was washed with additional diethyl ether (4 mL) and was dried under vacuum. The solid was dissolved in 1:1 acetonitrile/water (3 mL) and was loaded onto a Bio-Rad weak cation exchange resin (3 mL, macro-prep cm ion exchange resin, sodium cycle). The column was washed with 1:1 acetonitrile/water (2 mL) and water (18 mL). The column was then eluted with 5% aqueous sodium chloride, collecting 3 mL fractions. Fractions 1–4 were cooled in an ice bath and were then loaded onto an amberchrom CG-161 resin (3 mL). The column was washed with cold de-ionized water (20 mL) and was eluted with 20% isopropanol in water, collecting 5 mL fractions. Fractions 1–4 were combined and concentrated to approximately 1 mL, which was lyophilized to give the title compound (0.006 g).

$^1$H NMR (D$_2$O, 500 MHz) δ 1.16 (d, 1-CH$_3$), 1.21 (d, CH$_3$CHOH), 2.00 (m, ArCH$_2$CH$_2$CH$_2$OH), 3.11 (dq, H-1), 3.42 (dd, H-6), 3.62 and 3.65 (m, ArCH$_2$CH$_2$CH$_2$OH), 3.93 and 4.05 (2 m, NCH$_2$CH$_2$N), 4.05 (dd, H-5), 4.17 (dq, H-8), 4.36 (s, CH$_2$CONH$_2$), 4.63 and 5.26 (2d's, CH$_2$N), 5.20 (s, ArCH$_2$), 6.89 (d, ArH), 7.78 (d ArH), 7.99 (dd, ArH), 8.15 (d, ArH) and 8.40 (d, ArH).

EXAMPLE 3

SYNTHESIS OF (1S,5R,6S)-2-(5-((1-METHYLIMIDAZOL-3-IUM)METHYL)(1,8-NAPHTHOSULTAM)METHYL)-6-[1(R)-HYDROXYETHYL]-1-METHYLCARBAPEN-2-EM-3-CARBOXYLATE

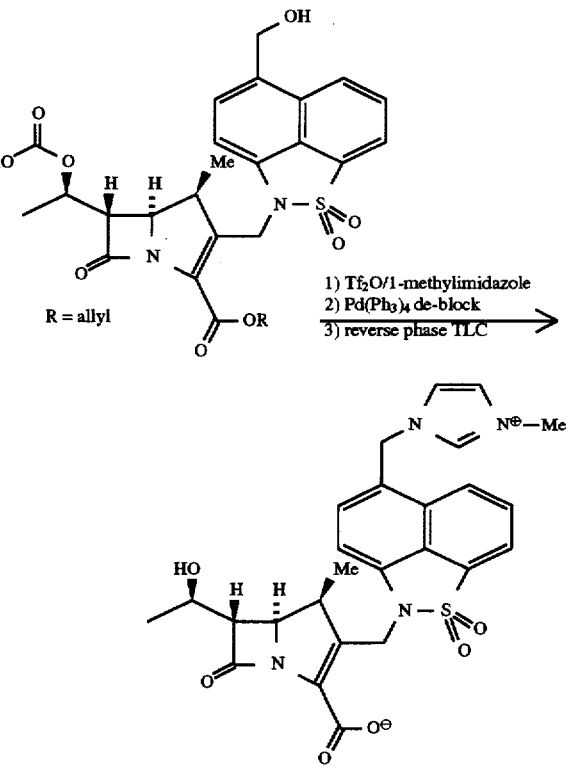

To a solution of allyl(1S,5R,6S)-2-(5-(hydroxymethyl-1,8-naphthosultam)methyl)-6-[1(R)-(allyloxycarbonyl)oxyethyl]-1-methylcarbapen-2-em-3-carboxylate (0.065 g, 0.11 mmol) in dichloromethane (2 mL), cooled in a dry ice/acetone bath under nitrogen, was added 1-methylimidazole (0.035 mL, 0.44 mmol) followed by trifluoromethanesulfonic anhydride (0.038 mL, 0.22 mmol). After 5 minutes the flask was removed from the bath and the mixture was stirred at room temperature for 45 minutes. The mixture was then partitioned between methylene chloride (10 mL) and water (10 mL). The methylene chloride layer was washed with water (10 mL), dried over magnesium sulfate, filtered, and evaporated. The residual oil (0.08 g) was dissolved in methylene chloride (2 mL) then 0.5M sodium ethyl hexanoate in ethyl acetate (0.22 mL, 0.11 mmol) and ethyl hexanoic acid (0.017mL, 0.11 mmol) were added. The solution was blanketed with nitrogen, using a Firestone valve, and triphenylphosphine (0.008 g, 0.03 mmol) and tetrakis(triphenylphosphine)palladium (0.035 g, 0.03 mmol) were added. After 40 minutes the methylene chloride was evaporated under a stream of nitrogen and dimethylformamide (1.5 mL) was added. After an additional 15 minutes, diethyl ether (6 mL) was added and the supernatant was decanted from the precipitate. The solid was washed with additional diethyl ether (6 mL) and dried under vacuum. The solid was purified on a 1000 micron reverse phase TLC plate developed with 30% acetonitrile/water and eluted with 80% acetonitrile/water (25 mL). The eluent was diluted with water (15 mL), washed with hexanes (25 mL), concentrated to approximately 1 mL and lyophilized to give the title compound (0.024 g).

$^1$H NMR (D$_2$O, 500 MHz) δ 1.13 (d, 1-CH$_3$), 1.21 (d, C H$_3$CHOH), 3.06 (dq, H-1), 3.40 (dd, H-6), 3.78 (s, ImMe), 4.02 (dd, H-5), 4.17 (dq, H-8), 4.57 and 5.22 (2d's, CH$_2$N), 5.70 (s, ArCH$_2$), 6.78 (d, ArH), 7.37 and 7.41 (2 m, ImH), 7.59 (d, ArH), 7.83 (t, ArH), 8.05 (d, ArH), 8.14 (d, ArH) and 8.63 (s, ImH).

EXAMPLE 4

SYNTHESIS OF (1S,5R,6S)-2-(5-(((2-(1-METHYLIMIDAZOL-3-IUM)-ETHYL)(1,8-NAPHTHOSULTAM)METHYL)-6-[1(R)-HYDROXYETHYL]-1-METHYLCARBAPEN-2-EM-3-CARBOXYLATE

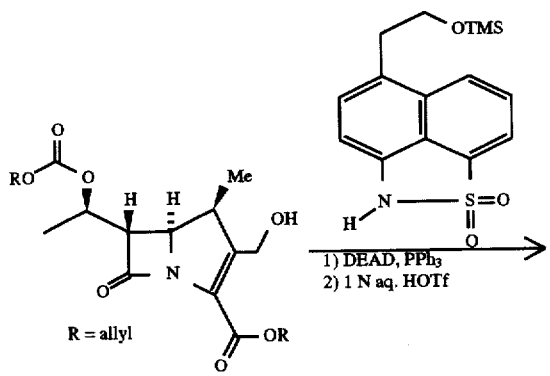

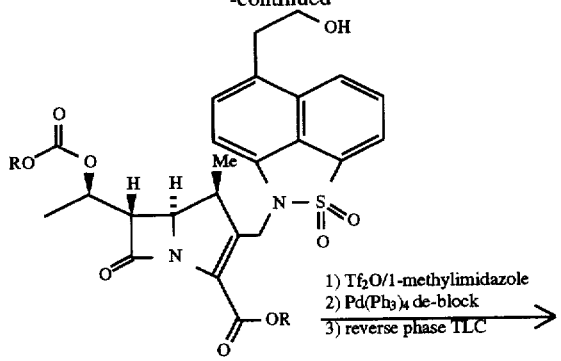

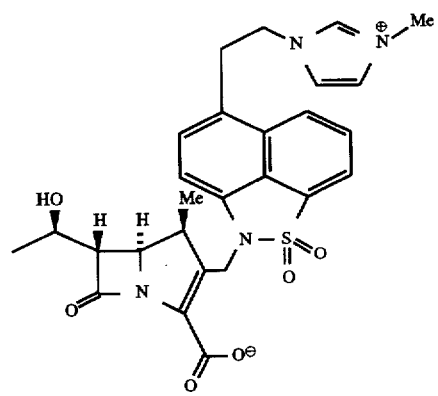

Step 1
Synthesis of allyl(1S,5R,6S)-2-(5-((2-hydroxy)-ethyl-1,8-naphthosultam)methyl)-6-[1(R)-(allyloxycarbonyl) oxyethyl]-1-methylcarbapen-2-em-3-carboxylate To a solution of allyl(1S,5R,6S)-2-(hydroxymethyl)-6-[1 (R)-(allyloxycarbonyl)oxyethyl]-1-methylcarbapen-2-em-3-carboxylate (0.086 g, 0.235 mmol), 4-((2-trimethylsilyloxy)-ethyl)-1,8-naphthosultam (0.08 g, 0.247 mmol) and triphenylphosphine (0.093 g, 0.353 mmol) in tetrahydrofuran (1 mL), cooled in an ice bath, was added diethylazodicarboxylate (0.056 mL, 0.353 mmol). After 30 minutes the mixture was partitioned between ethyl acetate (20 mL) and water (20 mL). The water layer was extracted with ethyl acetate (10 mL) and the combined ethyl acetate layers were washed with saturated aqueous sodium chloride (20 mL), dried over magnesium sulfate, filtered, and evaporated. The residual oil was purified by preparative thin layer chromatography (2×1000 micron silica gel plates, developed/eluted with 5% EtOAc/CH$_2$Cl$_2$) to give an oil (0.074 g, 47%). This oil was dissolved in a mixture of tetrahydrofuran (2 mL) and water (0.5 mL) then 1N aqueous trifluoromethane sulfonic acid (0.02 mL, 0.02 mmol) was added. After 5 minutes the mixture was partitioned between methylene chloride (20 mL) and 1% aqueous bicarbonate (20 mL). The water layer was extracted with methylene chloride (5 mL) and the combined methylene chloride layers were dried over magnesium sulfate, filtered, and evaporated. The residue was lyophilized from benzene (3 mL) to give the title compound as a solid (0.062 g).

¹H NMR (CDCl₃, 500 MHz) δ 1.32 (d, 1-CH₃), 1.46 (d, C$\underline{H}$₃CHO(ALLOC)), 3.29 (m, ArC$\underline{H}$₂CH₂OH), 3.40 (dq, H-1), 3.45 (dd, H-6), 3.97 (dt, ArC$\underline{H}$₂CH₂OH), 4.17 (dd, H-5), 4.59 and 4.88 (2m's, 2CH₂vinyl), 5.14 (dq, H-8), 5.26, 5.33, 5.35 and 5.53 (4m's, 4 vinyl H's), 4.67 and 5.40 (2d's, CH₂N), 5.91 and 6.05 (2m's, 2CH₂vinyl), 6.69 (d, ArH), 7.40 (d, ArH), 7.83 (dd, ArH), 8.02 (d, ArH) and 8.28 (d, ArH).

Step 2
(1S,5R,6S)-2-(5-((2-(1-methylimidazol-3-ium)-ethyl)(1,8-naphthosultam)methyl)-6-[1(R)-hydroxyethyl]-1-methylcarbapen-2-em-3-carboxylate To a solution of allyl(1S,5R,6S)-2-(5-(2-hydroxy)ethyl-1,8-naphthosultam)methyl)-6-[1(R)-(allyloxycarbonyl)oxyethyl]-1-methylcarbapen-2-em-3-carboxylate (0.03 g, 0.05 mmol) in dichloromethane (0.5 mL), cooled in a dry ice/acetone bath under nitrogen, was added 1-methylimidazole (0.032 mL, 0.40 mmol) followed by trifluoromethane-sulfonic anhydride (0.017 mL, 0.10 mmol). After 5 minutes the flask was removed from the bath and stirred at room temperature for 20 minutes. The mixture was partitioned between methylene chloride (20 mL) and water (20 mL). The methylene chloride layer was washed with water (100 mL), dried over magnesium sulfate, filtered and evaporated. The residual oil (0.053 g) was dissolved in dimethylformamide (0.7 mL) and was cooled in an ice bath. A solution of 0.5M sodium ethyl hexanoate in ethyl acetate (0.11 mL, 0.055 mmol) and ethyl hexanoic acid (0.018 mL, 0.11 mmol) were added. The solution was blanketed with nitrogen, using a Firestone valve, and triphenylphosphine (0.004 g, 0.0165 mmol) and tetrakis(triphenylphosphine) palladium (0.019 g, 0.0165 nunol) were added. After 70 minutes, diethyl ether (5 mL) was added and the supernatant was decanted from the precipitate. The solid was washed with additional diethyl ether (5 mL) and was dried under vacuum. The solid was purified on a 1000 micron reverse phase plate developed, in an ice bath, with 30% acetonitrile/water and eluted with 80% acetonitrile/water (15 mL). The eluent was diluted with de-ionized water (10 mL), washed with hexanes (40 mL), evaporated to approximately 2 mL and lyophilized to give the title compound (0.020 g).

¹H NMR (D₂O, 500 MHz) δ 1.11 (d, 1-CH₃), 1.20 (d, C$\underline{H}$₃CHOH), 3.06 (dq, H-1), 3.29 (m, ArC$\underline{H}$₂CH₂Q), 3.38 (dd, H-6), 3.60 (s, ImMe), 4.04 (dd, H-5), 4.17 (dq, H-8), 4.38 (m, ArCH₂C$\underline{H}$₂Q), 4.50 and 5.14 (2d's, CH₂N), 6.56 (d, ArH), 6.96 (d, ArH), 7.15 and 7.20 (2m, ImH), 7.69 (dd, ArH), 7.91 (d, ArH), 7.95 (d, ArH) and 8.15 (s, ImH).

EXAMPLE 5

SYNTHESIS OF (1S,5R,6S)-2-(4-((
(CARBAMOYLMETHYL)-1,4-
DIAZONIABICYCLO[2.2.2]OCT-1-YL)METHYL)
(1,8-NAPHTHOSULTAM)METHYL)-6-[1(R)-
HYDROXYETHYL]1-METHYLCARBAPEN-2-
EM-3-CARBOXYLATE CHLORIDE

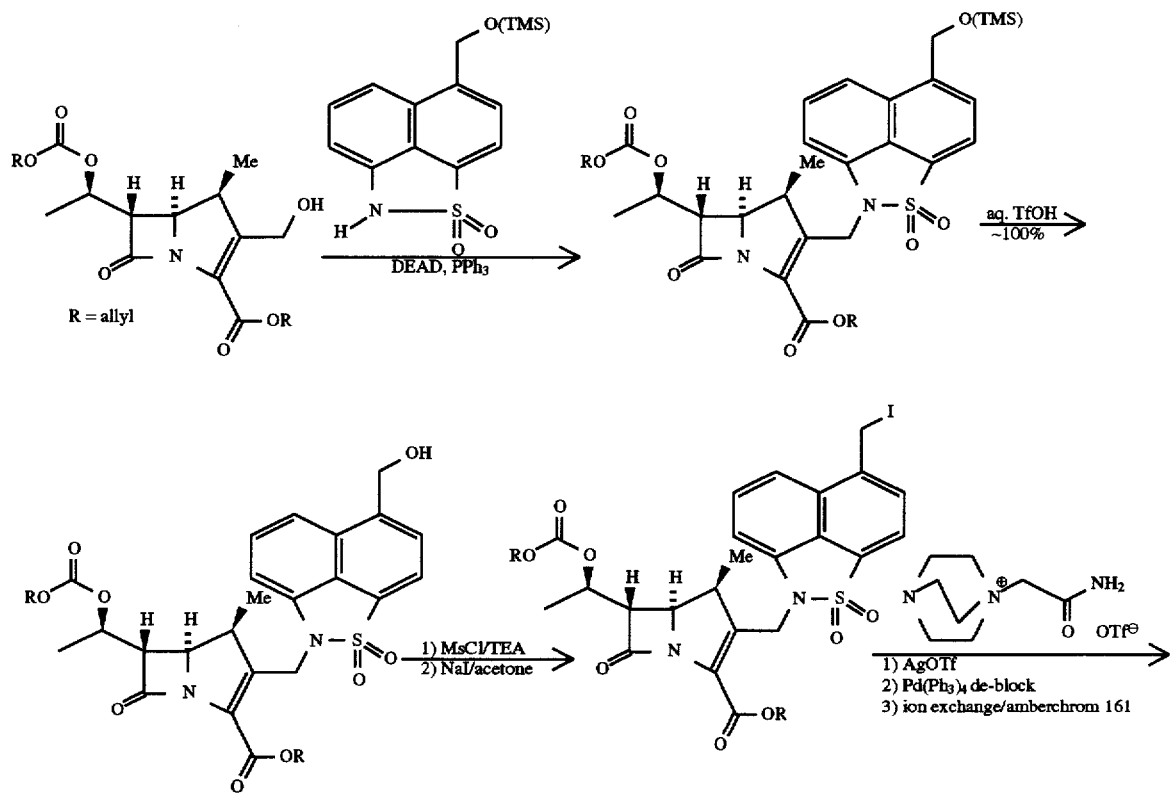

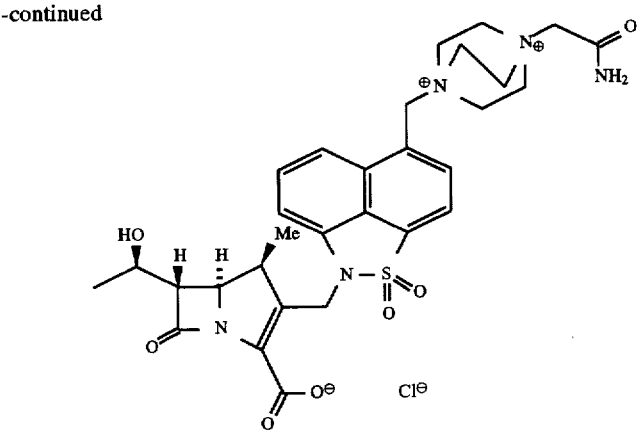

Step 1 allyl(1S,5R,6S)-2-(4-(trimethylsilyloxymethyl-1,8-naphthosultam)methyl)-6-[1(R)-(allyloxycarbonyl)oxyethyl]-1-methylcarbapen-2-em-3-carboxylate To a solution of allyl(1S,5R,6S)-2-(hydroxymethyl)-6-[1(R)-(allyloxycarbonyl)oxyethyl]-1-methylcarbapen-2-em-3-carboxylate (0.037 g, 0.12 mmol), 4-(trimethylsilyloxymethyl)-1,8-naphthosultam (0.049 g, 0.12 mmol) and triphenylphosphine (0.047 g, 0.18 mmol) in tetrahydrofuran (0.7 mL), cooled in an ice bath, was added diethylazodicarboxylate (0.028 mL, 0.18 mmol). After 30 minutes, the mixture was partitioned between ethyl acetate (20 mL) and water (20 mL). The water layer was extracted with ethyl acetate (10 mL) and the combined ethyl acetate layers were washed with saturated aqueous sodium chloride (20 mL), dried over magnesium sulfate, filtered and evaporated. The residual oil was purified by preparative thin layer chromatography on a 1000 micron silica gel plate, developed/eluted with 5% EtOAc/CH$_2$Cl$_2$) to give the title compound as an oil (0.045 g).

$^1$H NMR (CDCl$_3$, 500 MHz) δ 0.23 (s, TMS), 1.31 (d, 1-CH$_3$), 1.45 (d, C$\underline{H}_3$CHO(ALLOC)), 3.40 (dq, H-1), 3.45 (dd, H-6), 4.16 (dd, H-5), 4.59 and 4.88 (2m's, 2CH$_2$vinyl), 5.13 (dq, H-8), 5.22 (s, CH$_2$O), 5.26, 5.34, 5.35 and 5.53 (4m's, 4 vinyl H's), 4.68 and 5.40 (2d's, CH$_2$N), 5.91 and 6.05 (2m's, 2CH$_2$vinyl), 6.72 (m, ArH), 7.53 (m, 2ArH), 7.90 (m, ArH), and 7.98 (d, ArH).

Step 2 allyl(1S,5R,6S)-2-(4-(hydroxymethyl-1,8-naphthosultam)methyl)-6-[1(R)-(allyloxycarbonyl)oxyethyl]-1-methylcarbapen-2-em-3-carboxylate To a solution of allyl(1S,5R,6S)-2-(4-(trimethylsilyloxymethyl-1,8-naphthosultam)methyl)-6-[1(R)-(allyloxycarbonyl)oxyethyl]-1-methylcarbapen-2-em-3-carboxylate (0.045 g, 0.069 mmol) in a mixture of tetrahydrofuran (1 mL) and water (0.5 mL), was added 1N aqueous trifluoromethane sulfonic acid (0.01 mL, 0.01 mmol). After 5 minutes, the mixture was partitioned between methylene chloride (20 mL) and 5% aqueous bicarbonate (5 mL). The water layer was extracted with methylene chloride (5 mL) and the combined methylene chloride layers were dried over magnesium sulfate, filtered and evaporated to give the title compound as an oil (0.04 g, quant).

$^1$H NMR (CDCl$_3$, 500 MHz) δ 1.30 (d, 1-CH$_3$), 1.44 (d, C$\underline{H}_3$CHO(ALLOC)), 3.39 (dq, H-1), 3.44 (dd, H-6), 4.15 (dd, H-5), 4.58 and 4.88 (2m's, 2CH$_2$vinyl), 5.13 (dq, H-8), 5.22 (d, CH$_2$O), 5.25, 5.33, 5.34 and 5.52 (4m's, 4 vinyl H's), 4.67 and 5.40 (2d's, CH$_2$N), 5.90 and 6.04 (2m's, 2CH$_2$vinyl), 6.73 (d, ArH), 7.53 (dd, ArH), 7.59 (dd, ArH), 7.88 (d, ArH) and 7.97 (d, ArH).

Step 3 allyl(1S,5R,6S)-2-(4-(iodomethyl-1,8-naphthosultam)methyl)-6-1(R)-(allyloxycarbonyl)oxyethyl]-1-methylcarbapen-2-em-3-carboxylate To a solution of allyl(1S,5R,6S)-2-(4-(hydroxymethyl-1,8-naphthosultam)methyl)-6-[1(R)-(allyloxycarbonyl)oxyethyl]-1-methylcarbapen-2-em-3-carboxylate (0.043 g, 0.074 mmol) in dichloromethane (1.5 mL), cooled in an ice bath under nitrogen, was added triethylamine (0.018 mL, 0.13 mmol) followed by methane sulfonyl chloride (0.009 mL, 0.111 mmol). After a total of 30 minutes the mixture was partitioned between methylene chloride (20 mL) and 0.1N aqueous hydrochloric acid (20 mL). The methylene chloride layer was dried over magnesium sulfate then filtered and evaporated. Examination of the residual oil by $^1$H NMR showed a complete conversion to the mesylate. The oil was dissolved in acetone (2 mL) then sodium iodide (0.067 g, 0.444 mmol) was added and the mixture was stirred at room temperature for 75 minutes. The reaction was partitioned between methylene chloride (20 mL) and water (20 mL). The methylene chloride layer was washed with 5% aqueous NaHSO$_3$ (20 mL), dried over magnesium sulfate, filtered, and evaporated. The residual oil was lyophilized from benzene (3 mL) to give the title compound as a foam (0.039 g)

$^1$H NMR (CDCl$_3$, 500 MHz) δ 1.31 (d, 1-CH$_3$), 1.46 (d, C$\underline{H}_3$CHO(ALLOC)), 3.40 (dq, H-1), 3.46 (dd, H-6), 4.17 (dd, H-5), 4.59 and 4.89 (2m's, 2CH$_2$vinyl), 4.90 (m, CH$_2$I), 5.14 (dq, H-8), 5.26, 5.34, 5.36 and 5.53 (4m's, 4 vinyl H's), 4.67 and 5.42 (2d's, CH$_2$N), 5.91 and 6.05 (2m's, 2CH$_2$vinyl), 6.74 (m, ArH), 7.65 (m, 2ArH), 7.81 (d, ArH), and 7.87 (d, ArH).

Step 4

(1S,5R,6S)-2-(4-(((carbamoylmethyl)-1,4-diazoniabicyclo [2.2.2]oct-1-yl)methyl)(1,8-naphthosultam)methyl)-6-[1(R)-hydroxyethyl]-1-methylcarbapen-2-em-3-carboxylate chloride To a solution of allyl(1S,5R,6S)-2-(4-(iodomethyl-1,8-naphthosultam)methyl)-6-[1(R)-(allyloxycarbonyl)oxyethyl]-1-methylcarbapen-2-em-3-carboxylate (0.039 g, 0.056 mmol) in acetonitrile (0.5 mL) was added 1-carbamoylmethyl-4-aza-1-azoniabicyclo-[2.2.2]octane trifluoromethane sulfonate (0.022 g, 0.0676 mmol) and silver trifluoromethane sulfonate (0.056 mL of a 1.0M solution in acetonitrile, 0.056 mmol). The suspension was stirred for 1 hour at room temperature, then filtered and the solvent was evaporated under vacuum. The residual oil was dissolved in dimethylformamide (0.9 mL) and the solution was cooled in an ice bath as 0.5M sodium ethyl hexanoate in ethyl acetate (0.12 mL, 0.062 mmol) and ethyl hexanoic acid (0.01 mL, 0.062 mmol) were added. The solution was blanketed with nitrogen, using a Firestone valve, and triphenylphosphine (0.0044 g, 0.017 mmol) and tetrakis (triphenylphosphine)palladium (0.02 g, 0.017 mmol) were added. After one hour, diethyl ether (25 mL) was added and the supernatant was decanted from the precipitate. The solid was washed with additional diethyl ether (25 mL) and dried under vacuum. The combined ether layers were extracted with water (10 mL) and the aqueous layer was loaded onto a Bio-Rad weak cation exchange resin (2.5 mL, macroprep CM weak cation exchange resin, sodium cycle). The solid was dissolved in 1:1 acetonitrile/water (2 mL) and was also loaded onto the ion-exchange resin. The column was washed with 1:1 acetonitrile/water (10 mL) and water (50 mL). The column was then eluted with 5% aqueous sodium chloride, collecting 8 mL fractions. Fractions 1–6 were cooled in an ice bath and were then loaded onto an amberchrom CG-161 resin (3 mL). The column was washed with cold de-ionized water (50 mL) and was eluted with 20% isopropanol in water, collecting 3 mL fractions. Fractions 1+2 were combined and concentrated to approximately 1 mL which was lyophilized to give the title compound (0.01 g).

$^1$H NMR (D$_2$O, 500 MHz) δ 1.07 (d, 1-CH$_3$), 1.22 (d, CH$_3$CHOH), 2.98 (dq, H-1), 3.37(dd, H-6), 3.95 (dd, H-5), 4.15 (dq, H-8), 4.15 and 4.22 (2m, NCH$_2$CH$_2$N), 4.36 (s, CH$_2$CONH$_2$), 4.57 and 5.17 (2d's, CH$_2$N), 5.34 (s, ArCH$_2$), 6.89 (d, ArH), 7.72 (m, 2ArH), 8.10 (dd, ArH) and 8.16 (d, ArH).

EXAMPLE 6

SYNTHESIS OF (1S,5R,6S)-2-(4-(2-((CARBAMOYLMETHYL)-1,4-DIAZONIABICYCLO[2.2.2]OCT-1-YL))-ETHYL)(1,8-NAPHTHOSULTAM)METHYL)-6-[1(R)-HYDROXYETHYL]-1-METHYLCARBAPEN-2-EM-3-CARBOXYLATE CHLORIDE

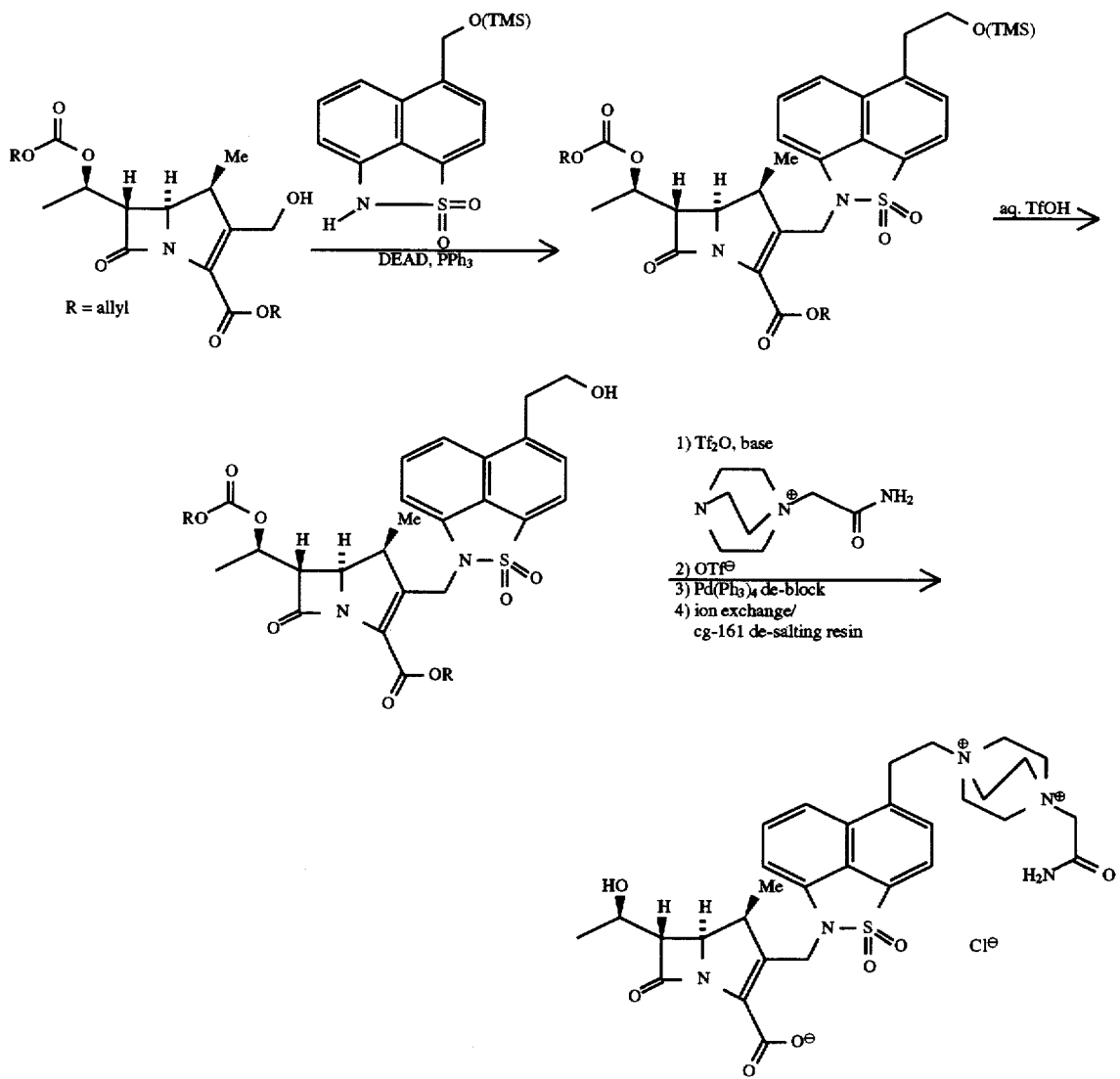

Step 1
Synthesis of allyl(1S,5R,6S)-2-(4-(trimethylsilyloxyethyl-1,8-naphthosultam)methyl)-6-[1(R)-(allyloxycarbonyl)oxyethyl]-1-methylcarbapen-2-em-3-carboxylate To a solution of allyl(1S,5R,6S)-2-(hydroxymethyl)-6-[1(R)-(allyloxycarbonyl)oxyethyl]-1-methylcarbapen-2-em-3-carboxylate (0.086 g, 0.235 mmol), 4-(2(-trimethylsilyloxy)-ethyl)-1,8-naphthosultam (0.08 g, 0.247 mmol) and triphenylphosphine (0.093 g, 0.353 mmol) in tetrahydrofuran (1 mL), cooled in an ice bath, was added diethylazodicarboxylate (0.056 mL, 0.353 mmol). After 30 minutes the mixture was partitioned between ethyl acetate (20 mL) and water (20 mL). The aqueous layer was extracted with ethyl acetate (10 mL), and the combined organic layers were washed with saturated aqueous sodium chloride (30 mL), dried over magnesium sulfate, filtered and evaporated. The residual oil was purified by preparative thin layer chromatography (2×1000 micron silica gel plates, developed/eluted with 5% EtOAc/$CH_2Cl_2$) to give the title compound as an oil (0.105 g).

$^1$H NMR ($CDCl_3$, 500 MHz) δ 0.04 (s, TMS), 1.31 (d, 1-$CH_3$), 1.45 (d, $CH_3$CHO(ALLOC)), 3.36 (t, $ArCH_2CH_2O$(TMS)), 3.40 (dq, H-1), 3.45 (dd, H-6), 3.93 (t, $ArCH_2CH_2O$(TMS)), 4.16 (dd, H-5), 4.60 and 4.89 (2m's, $2CH_2$vinyl), 5.14 (dq, H-8), 5.26, 5.34, 5.36 and 5.53 (4m's, 4 vinyl H's), 4.69 and 5.40 (2d's, $CH_2N$), 5.91 and 6.05 (2m's, $2CH_2$vinyl), 6.72 (d, ArH), 7.52 (t, ArH), 7.63 (d, ArH), 7.64 (d, ArH) and 7.93 (d, ArH).

Step 2
allyl(1S,5R,6S)-2-(4-(2-(hydroxy)-ethyl-1,8-naphthosultam)methyl)-6-[1(R)-(allyloxycarbonyl)oxyethyl]-1-methylcarbapen-2-em-3-carboxylate To a solution of allyl(1S,5R,6S)-2-(4-(2-(trimethylsilyloxy)-ethyl-1,8-naphthosultam)methyl)-6-[1(R)-(allyloxycarbonyl)oxyethyl]-1-methylcarbapen-2-em-3-carboxylate (0.105 g, 0.157 mmol) in a mixture of tetrahydrofuran (2 mL) and water (0.5 mL), was added 1N aqueous trifluoromethanesulfonic acid (0.02 mL, 0.02 mmol). After 5 minutes, the mixture was partitioned between methylene chloride (20 mL) and 5% aqueous bicarbonate (20 mL). The water layer was extracted with methylene chloride (5 mL), and the combined methylene chloride layers were dried over magnesium sulfate, filtered and evaporated to give the title compound as an oil (0.096 g, quant).

$^1$H NMR ($CDCl_3$, 500 MHz) δ 1.31 (d, 1-$CH_3$), 1.45 (d, $CH_3$CHO(ALLOC)), 3.41 (t, $ArCH_2CH_2OH$), 3.41 (dq, H-1), 3.45 (dd, H-6), 4.04 (dt, $ArCH_2CH_2O$(TMS), 4.16 (dd, H-5), 4.59 and 4.89 (2m's, $2CH_2$vinyl), 5.14 (dq, H-8), 5.26, 5.33, 5.35 and 5.53 (4m's, 4 vinyl H's), 4.69 and 5.41 (2d's, $CH_2N$), 5.91 and 6.05 (2m's, $2CH_2$vinyl), 6.73 (d, ArH), 7.54 (dd, ArH), 7.63 (d, ArH), 7.68 (d, ArH) and 7.95 (d, ArH).

Step 3
(1S,5R,6S)-2-(4-(2-(((carbamoylmethyl)-1,4-diazoniabicyclo[2.2.2]oct-1-yl))-ethyl)(1 8-naphthosultam)methyl)-6-[1(R)-hydroxyethyl]-1-methylcarbapen-2-em-3-carboxylate chloride To a solution of allyl(1S,5R,6S)-2-(4-((2-hydroxy)-ethyl-1,8-naphthosultam)methyl)-6-[1(R)-(allyloxycarbonyl)oxyethyl]-1-methylcarbapen-2-em-3-carboxylate (0.25 g, 0.419 mmol) in dichloromethane (8 mL), cooled in a methanol/ice bath (−15° C.) under nitrogen, was added 2,6-lutidine (0.147 mL, 1.26 mmol) followed by trifluoromethanesulfonic anhydride ($Tf_2O$) (0.106 mL, 0.629 mmol). After 30 minutes the mixture was partitioned between methylene chloride (80 mL) and 0.05N aqueous hydrochloric acid (80 mL). The methylene chloride layer was washed with water (80 mL), dried over magnesium sulfate and filtered into a flask containing a solution of 1-carbamoylmethyl-4-aza-1-azoniabicyclo[2.2.2]octane trifluoromethanesulfonate (0.147 g, 0.461 mmol) in acetonitrile (4 mL). The mixture was concentrated under vacuum to give a viscous oil (ca. 1 mL). After 30 minutes, additional 1-carbamoylmethyl-4-aza-1-azoniabicyclo[2.2.2]octane trifluoromethanesulfonate (0.015 g, 0.047 mmol) was added and the mixture was diluted with dimethylformamide (5 mL). The solution was cooled in an ice bath and 0.5M sodium ethyl hexanoate in ethyl acetate (0.84 mL, 0.419 mmol) and ethyl hexanoic acid (0.067 mL, 0.419 mmol) were added. The solution was blanketed with nitrogen, using a Firestone valve, and triphenylphosphine (0.033 g, 0.126 mmol) and tetrakis(triphenylphosphine)palladium (0.146 g, 0.126 mmol) were added. After one hour, diethyl ether (50 mL) was added and the supernatant was decanted from the precipitate. The solid was washed with additional diethyl ether (50 mL) and was dried under vacuum. The solid was dissolved in 1:1 acetonitrile/water (5 mL) and was loaded onto a Bio-Rad weak cation exchange resin (21 mL, 2.75×4 cm, macroprep cm ion exchange resin, sodium cycle). The column was washed with 1:1 acetonitrile/water (20 mL) and water (100 mL). The column was then eluted with 5% aqueous sodium chloride, collecting 8 mL fractions. Fractions 4–36 were cooled in an ice bath and were then loaded onto an amberchrom CG-161 resin (30 mL, 8×2.5 cm). The column was washed with cold de-ionized water (200 mL) and was eluted with 20% isopropanol in water, collecting 8 mL fractions. Fractions 5–10 were combined and concentrated to approximately 15 mL, which was lyophilized to give the title compound (0.157 g).

$^1$H NMR ($D_2O$, 500 MHz) δ 1.08 (d, 1-$CH_3$), 1.18 (d, $CH_3$CHOH), 3.01 (dq, H-1), 3.36 (dd, H-6), 3.67 (m, $ArCH_2CH_2Q$), 3.93 (m, $ArCH_2CH_2Q$), 3.93 (dd, H-5), 4.10 (dq, H-8), 4.25 and 4.37 (2m, $NCH_2CH_2N$), 4.46 (s, $CH_2CONH_2$), 4.51 and 5.12 (2d's, $CH_2N$), 6.63 (d, ArH), 7.37 (t, ArH), 7.42 (d, ArH), 7.73 (d, ArH) and 8.00 (d, ArH).

EXAMPLE 7

SYNTHESIS OF (1S,5R,6S)-2-(4-(2-(((3-HYDROXYPROP-1-YL)-1,4-DIAZONIABICYCLO[2.2.2]OCT-1-YL))-ETHYL)(1,8-NAPHTHOSULTAM)METHYL)-6-[1(R)-HYDROXYETHYL]-1-METHYLCARBAPEN-2-EM-3-CARBOXYLATE CHLORIDE

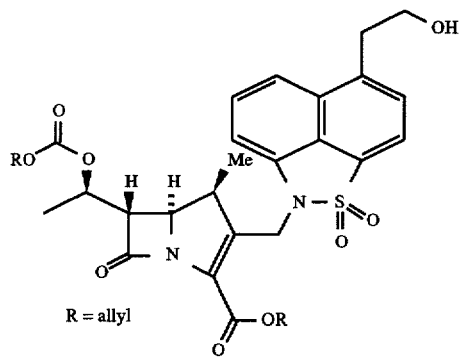
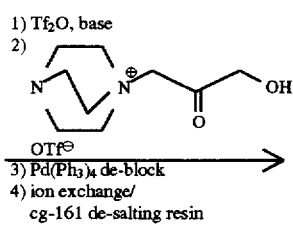

R = allyl

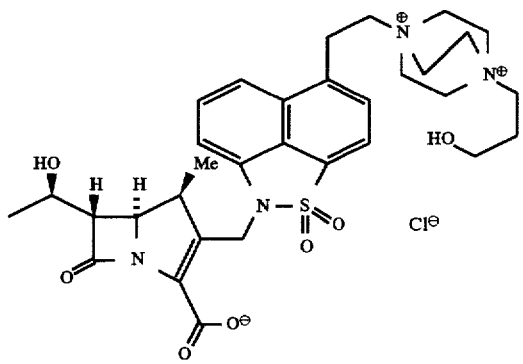

To a solution of allyl(1S,5R,6S)-2-(4-((2-hydroxy)-ethyl-1,8-naphthosultam)methyl)-6-[1(R)-(allyloxycarbonyl)oxyethyl]-1-methylcarbapen-2-em-3-carboxylate (0.29 g, 0.486 mmol) in dichloromethane (9 mL), cooled in a methanol/ice bath (−15° C.) under nitrogen, was added 2,6-lutidine (0.17 mL, 1.46 mmol) followed by trifluoromethane sulfonic anhydride (0.123 mL, 0.729 mmol). After 30 minutes the mixture was partitioned between methylene chloride (100 mL) and 0.05N aqueous hydrochloric acid (100 mL). The methylene chloride layer was washed with water (100 mL), dried over magnesium sulfate and filtered into a flask containing a solution of 1-carbamoylmethyl-4-aza-1-azoniabicyclo[2.2.2]octane trifluoromethanesulfonate (0.187 g, 0.461 mmol) in acetonitrile (4 mL). The solvents were evaporated under vacuum to give a viscous oil (ca. 1 mL). After 30 minutes the mixture was diluted with dimethylformamide (5 mL) and was cooled in an ice bath. A solution of 0.5M Sodium ethyl hexanoate in ethyl acetate (0.84 mL, 0.419 mmol) and ethyl hexanoic acid (0.067 mL, 0.419 mmol) were added, the solution was blanketed with nitrogen, using a Firestone valve, and triphenylphosphine (0.033 g, 0.126 mmol) and tetrakis(triphenylphosphine)palladium (0.146 g, 0.126 mmol) were added. After one hour, diethyl ether (50 mL) was added and the supernatant was decanted from the precipitate. The solid was washed with additional diethyl ether (50 mL) and was dried under vacuum. The solid was dissolved in 1:1 acetonitrile/water (5 mL) and was loaded onto a Bio-Rad weak cation exchange resin (21 mL, 2.75×4 cm, macroprep cm ion exchange resin, sodium cycle). The column was washed with 1:1 acetonitrile/water (22 mL) and then water (100 mL). The column was then eluted with 5% aqueous sodium chloride, collecting 8 mL fractions. Fractions 5–30 were cooled in an ice bath and were then loaded onto an amberchrom 161 resin (30 mL, 8×2.5 cm). The column was washed with cold de-ionized water (200 mL) and was eluted with 20% isopropanol in water, collecting 8 mL fractions.

Fractions 5–9 were combined and concentrated to approximately 15 mL which was lyophilized to give the title compound (0.18 g).

$^1$H NMR (D$_2$O, 500 MHz) δ 0.97 (d, 1-CH$_3$), 1.14 (d, C$\underline{H}_3$CHOH), 2.05 (m, ArCH$_2$C$\underline{H}_2$CH$_2$OH), 2.89 (dq, H-1), 3.29 (dd, H-6), 3.61 (m, ArC$\underline{H}_2$CH$_2$Q), 3.74 (2m, ArCH$_2$CH$_2$OH), 3.83 (dd, H-5), 3.91 (m, ArCH$_2$C$\underline{H}_2$Q), 4.05 (dq, H-8), 4.13 and 4.24 (2m, NCH$_2$CH$_2$N), 4.37 and 5.03 (2d's, CH$_2$N), 6.47 (d, ArH), 7.19 (t, ArH), 7.29 (d, ArH), 7.67 (d, ArH) and 7.91 (d, ArH).

EXAMPLE 8

SYNTHESIS OF (1S,5R,6S)-2-(4-(2-((1-METHYLIMIDAZOL-3-IUM))-ETHYL)(1,8-NAPHTHOSULTAM)METHYL)-6-|1(R)-HYDROXYETHYL|-1-METHYLCARBAPEN-2-EM-3-CARBOXYLATE

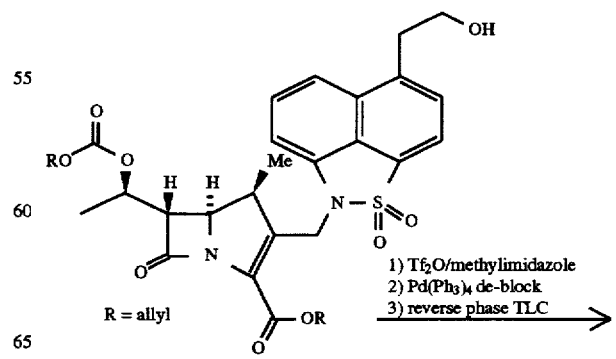

R = allyl

1) Tf$_2$O/methylimidazole
2) Pd(Ph$_3$)$_4$ de-block
3) reverse phase TLC

67
-continued

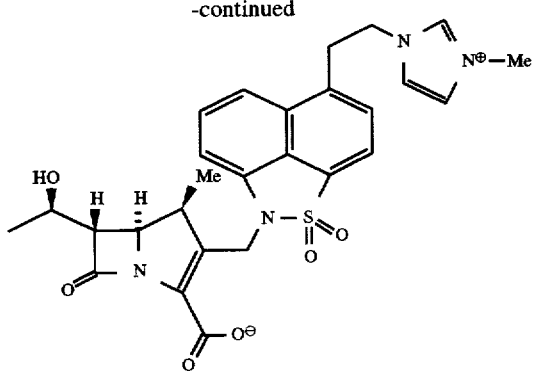

To a solution of allyl(1S,5R,6S)-2-(4-(2-(hydroxy)-ethyl-1,8-naphthosultam)methyl)-6-[1(R)-(allyloxycarbonyl)oxyethyl]-1-methylcarbapen-2-em-3-carboxylate (0.03 g, 0.05 mmol) in dichloromethane (0.5 mL), cooled in a dry ice/acetone bath under nitrogen, was added 1-methylimidazole (0.016 mL, 0.20 mmol) followed by trifluoromethane-sulfonic anhydride (0.017 mL, 0.10 mmol). After 5 minutes the flask was removed from the bath and stirred at room temperature for 50 minutes. Aditional 1-methylimidazole (0.016 mL, 0.20 mmol) was added and after 20 minutes the mixture was partitioned between methylene chloride (20 mL) and water (20 mL). The methylene chloride layer was washed with water (100 mL), dried over magnesium sulfate, filtered and evaporated to an oil (0.0436 g). The oil was dissolved in dimethylformamide (0.7 mL) and cooled in an ice bath. A solution of 0.5M sodium ethyl hexanoate in ethyl acetate (0.11 mL, 0.055 mmol) and ethyl hexanoic acid (0.018 mL, 0.11 mmol) were added, the solution was blanketed with nitrogen, using a Firestone valve, and triphenylphosphine (0.004 g, 0.0165 mmol) and tetrakis(triphenylphosphine)palladium (0.019 g, 0.0165 mmol) were added. After 70 minutes, diethyl ether (6 mL) was added and the supernatant was decanted from the precipitate. The solid was washed with additional diethyl ether (6 mL) and was dried under vacuum. The solid was purified on a 1000 micron reverse phase plate developed with 30% acetonitrile/water and eluted with 80% acetonitrile/water (15 mL). The eluent was diluted with water (15 mL), washed with hexanes (40 mL), evaporated to approximately 2 mL and lyophilized to give the title compound (0.017 g).

68

$^1$H NMR (D$_2$O, 500 MHz) δ 1.14 (d, 1-CH$_3$), 1.22 (d, C H$_3$CHOH), 3.08 (dq, H-1), 3.40 (dd, H-6), 3.55 (m, ArC H$_2$CH$_2$Q), 3.60 (s, ImMe), 4.04 (dd, H-5), 4.18 (dq, H-8), 4.52 (m, ArCH$_2$CH$_2$Q), 4.57 and 5.19 (2d's, CH$_2$N), 6.75 (d, ArH), 7.20 and 7.22 (2m, ImH), 7.24 (d, ArH), 7.39 (t, ArH), 7.47 (d, ArH), 7.93 (d, ArH) and 8.20 (s, ImH).

EXAMPLES 9-23

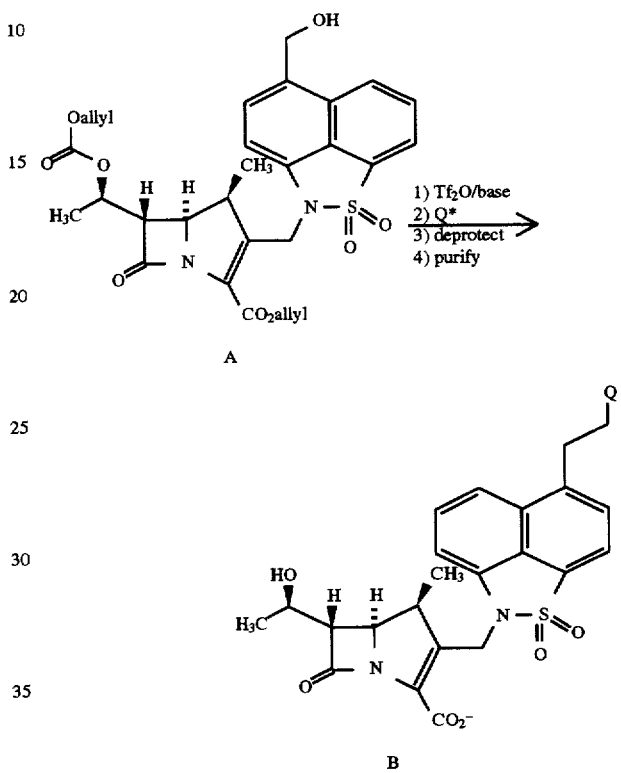

By appropriately modifying the procedure of Example 7, allyl(1S,5R,6S)-2-[N-(4-(2-hydroxy)-ethyl)-1,8-naphthosultam)methyl]-6-[(1R)-(allyloxycarbonyloxy)ethyl]-1-methylcarbapen-2-em-3-carboxylate (compound A) is reacted with compound Q* as set forth in the following Table to produce compounds of formula B in which Q is as defined in the following Table.

TABLE

| # | Q* | Q | # | Q* | Q | # | Q* | Q |
|---|----|---|---|----|---|---|----|---|
| 9 | TfO⁻, OH, N⁺(piperidine)-N | Cl⁻, OH, N⁺(piperidine)-N⁺ | 10 | PhS, TfO⁻, N⁺(piperidine)-N⁺ | PhS, Cl⁻, N⁺(piperidine)-N⁺ | 11 | TfO⁻, F, N⁺(piperidine)-N | Cl⁻, F, N⁺(piperidine)-N⁺ |

TfO⁻ represents a triflate anion

EXAMPLES 27–32

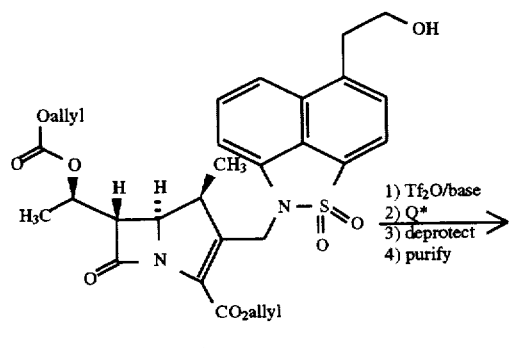

A

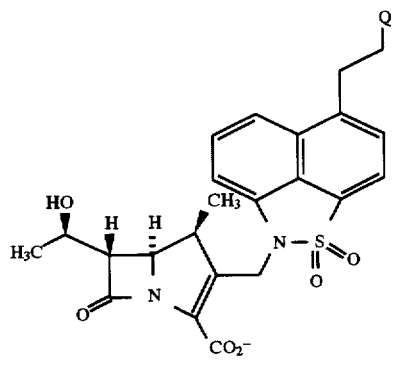

B

By appropriately modifying the procedure of Example 8, allyl(1S,5R,6S)-2-[N-(4-(2-hydroxy)-ethyl)-1,8-naphthosultam)methyl]-6-[(1R)-(allyloxycarbonyloxy)ethyl]-1-methylcarbapen-2-em-3-carboxylate (compound A) is reacted with compound Q* as set forth in the following Table to produce compounds of formula B in which Q is as defined in the following Table.

TABLE

| # | Q* | Q | # | Q* | Q | # | Q* | Q |
|---|----|---|---|----|---|---|----|---|
| 27 | pyridine | pyridinium | 28 | HO-ethyl-imidazole | HO-ethyl-imidazolium | 29 | quinuclidine | quinuclidinium |
| 30 | thiazole | thiazolium | 31 | oxazole | oxazolium | 32 | DABCO | DABCO+ |

EXAMPLE 33

SYNTHESIS OF ALLYL(1S,5R,6S)-2-(4-(3-(HYDROXY)-PROPYL-1,8-NAPHTHOSULTAM) METHYL)-6-[1(R)-(ALLYLOXYCARBONYL) OXYETHYL-]-1-METHYLCARBAPEN-2-EM-3-CARBOXYLATE

-(allyloxycarbonyl)oxyethyl]-1-methylcarbapen-2-em-3-carboxylate is reacted with 4-(3-trimethylsilyloxyprop-1-yl)-1,8-naphthosultam to afford allyl(1S,5R,6S)-2-[N-(4-(3-hydroxy)-propyl)-1,8-naphthosultam)-methyl]-6-[(1R)-(allyloxycarbonyloxy)ethyl]-1-methylcarbapen-2-em-3-carboxylate.

EXAMPLES 34-36

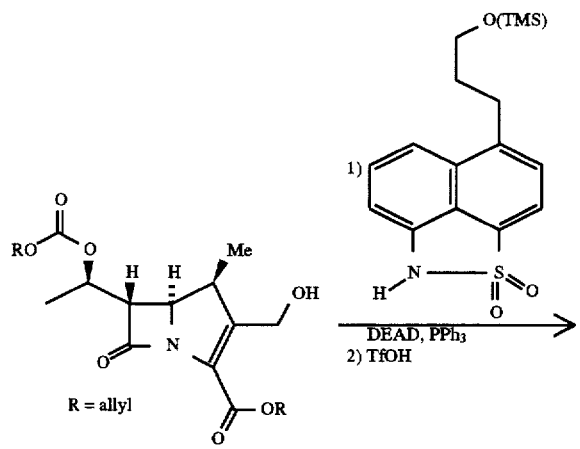

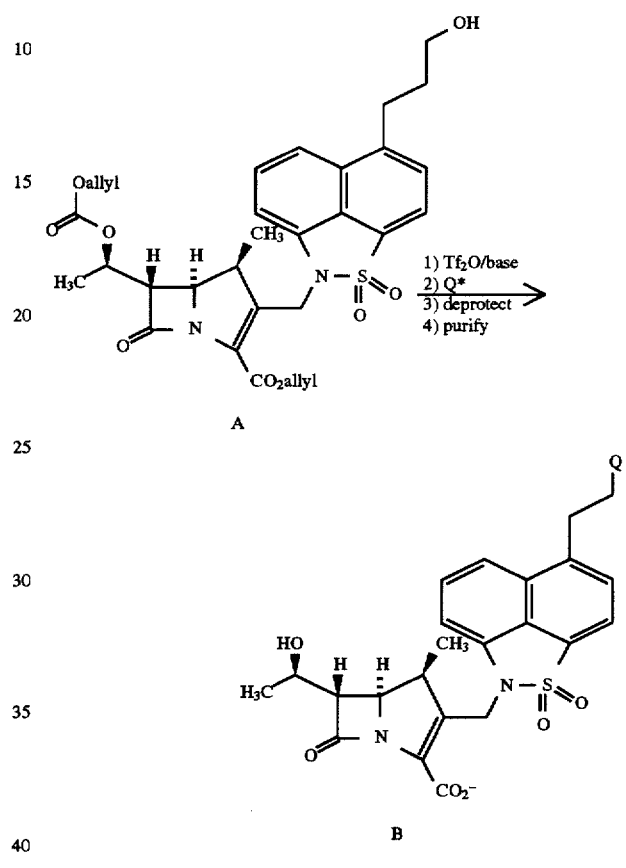

Steps 1 and 2
allyl(1S,5R,6S)-2-(4-(3-(hydroxy)-propyl-1,8-naphthosultam)methyl)-6-[1(R)-(allyloxycarbonyl)oxyethyl]-1-methylcarbapen-2-em-3-carboxylate By appropriately modifying the procedures of Steps 1 and 2 of Example 6, allyl(1S,5R,6S)-2-(hydroxymethyl)-6-[1(R)

By appropriately modifying the procedures of Example 7 and 8, allyl(1S,5R,6S)-2-[N-(4-(3-hydroxy)-propyl)-1,8-naphthosultam)-methyl]-6-[(1R)-(allyloxycarbonyloxy) ethyl]-1-methylcarbapen-2-em-3-carboxylate (compound A) is reacted with compound Q* as set forth in the following Table to produce compounds of formula B in which Q is as defined in the following Table.

TABLE

| # | Q* | Q | # | Q* | Q | # | Q* | Q |
|---|---|---|---|---|---|---|---|---|
| 34 | TfO⁻ [piperidinyl-N⁺-CH₂-C(=O)NH₂] | Cl⁻ [piperidinyl-N⁺-CH₂-C(=O)NH₂] | 35 | TfO⁻ HO-CH₂CH₂CH₂-N⁺(piperidinyl) | Cl⁻ HO-CH₂CH₂CH₂-N⁺(piperidinyl) | 36 | CH₃-N-pyrazolyl | CH₃-N⁺-pyrazolyl |

EXAMPLE 37

SYNTHESIS OF ALLYL(1S,5R,6S)-2-(3-(HYDROXYMETHYL-1,8-NAPHTHOSULTAM) METHYL)-6-[1(R)-(ALLYLOXYCARBONYL) OXYETHYL]-1-METHYLCARBAPEN-2-EM-3-CARBOXYLATE

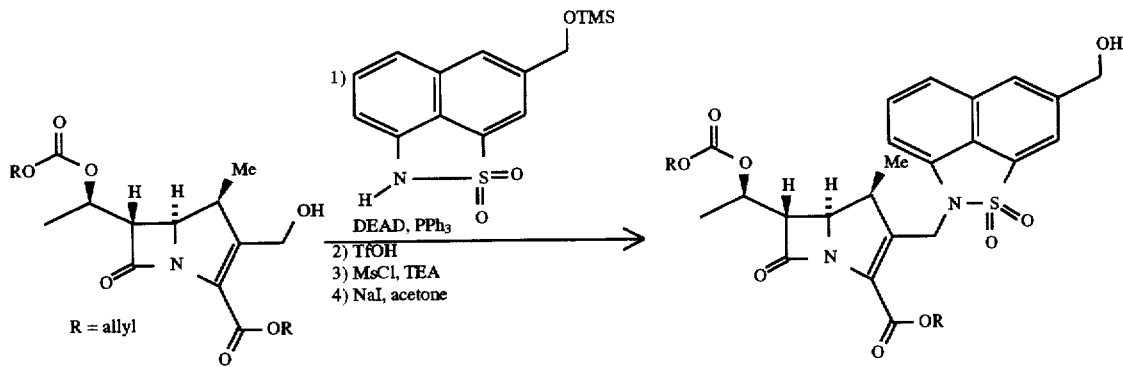

Steps 1 and 2 allyl(1S,5R,6S)-2-(3-(hydroxymethyl-1,8-naphthosultam) methyl)-6-[1(R)-(allyloxycarbonyl)oxyethyl]-1-methylcarbapen-2-em-3-carboxylate By appropriately modifying the procedures of Steps 1 and 2 of Example 1, allyl(1S,5R,6S)-2-(hydroxymethyl)-6-[1(R)-(allyloxycarbonyl) oxyethyl]-1-methylcarbapen-2-em-3-carboxylate is reacted with 3-(trimethylsilyloxymethyl)-1,8-naphthosultam to afford allyl(1S,5R,6S)-2-[N-(3-(hydroxymethyl)-1,8-naphthosultam)-methyl]-6-[(1R)-(allyloxycarbonyloxy)ethyl]-1-methylcarbapen-2-em-3-carboxylate.

EXAMPLES 38-40

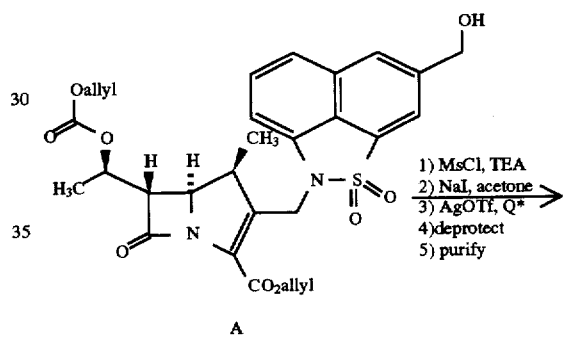

A

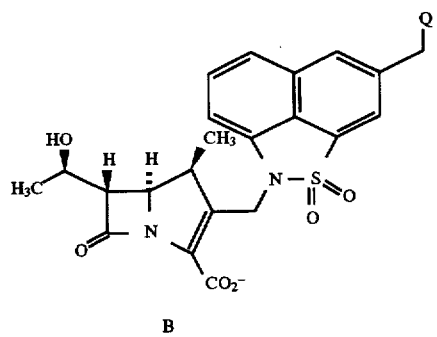

B

By appropriately modifying the procedures of Steps 3 and 4 of Example 1, allyl(1S,5R,6S)-2-[N-(3-(hydroxymethyl)-1,8-naphthosultam)-methyl]-6-[(1R)-(allyloxycarbonyloxy) ethyl]-1-methylcarbapen-2-em-3-carboxylate (compound A) is reacted with compound Q* as set forth in the following Table to produce compounds of formula B in which Q is as defined in the following Table.

TABLE

| # | Q* | Q | # | Q* | Q | # | Q* | Q |
|---|---|---|---|---|---|---|---|---|
| 38 | TfO⁻, NH₂-C(=O)-CH₂-N⁺(piperazine) | Cl⁻, NH₂-C(=O)-CH₂-N⁺(piperazinium) | 39 | TfO⁻, HO-CH₂CH₂-N⁺(piperazine) | Cl⁻, HO-CH₂CH₂-N⁺(piperazinium) | 40 | TfO⁻, F-CH₂CH₂-N⁺(piperazine) | Cl⁻, F-CH₂CH₂-N⁺(piperazinium) |

EXAMPLES 41–43

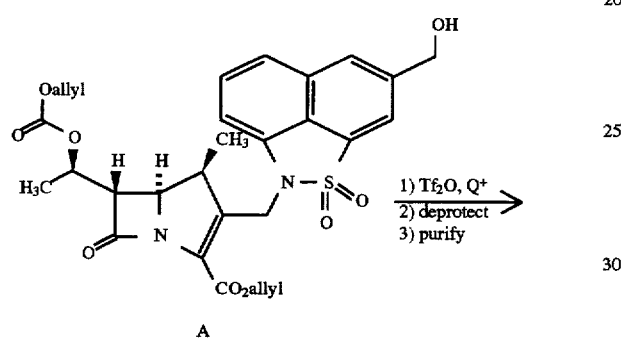

A

1) Tf₂O, Q⁺
2) deprotect
3) purify

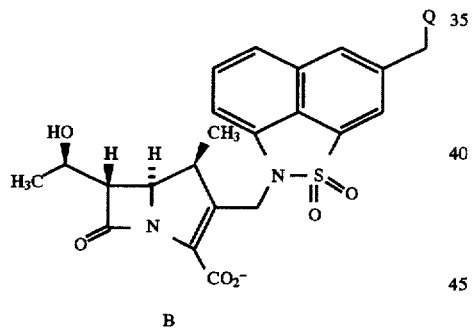

B

By appropriately modifying the procedure of Example 3, allyl(1S,5R,6S)-2-[N-(3-(hydroxymethyl)-1,8-naphthosultam)-methyl]-6-[(1R)-(allyloxycarbonyloxy)ethyl]-1-methylcarbapen-2-em-3-carboxylate (compound A) is reacted with compound Q* as set forth in the following Table to produce compounds of formula B in which Q is as defined in the following Table.

TABLE

| # | Q* | Q | # | Q* | Q | # | Q* | Q |
|---|---|---|---|---|---|---|---|---|
| 41 | CH₃-imidazole | CH₃-imidazolium | 42 | OH-CH₂CH₂-imidazole | OH-CH₂CH₂-imidazolium | 43 | thiazole | thiazolium |

EXAMPLE 44

SYNTHESIS OF ALLYL(1S,5R,6S)-2-(3-(2-(HYDROXY)-ETHYL-1,8-NAPHTHOSULTAM) METHYL)-6-[1(R)-(ALLYLOXYCARBONYL) OXYETHYL]-1-METHYLCARBAPEN-2-EM-3-CARBOXYLATE

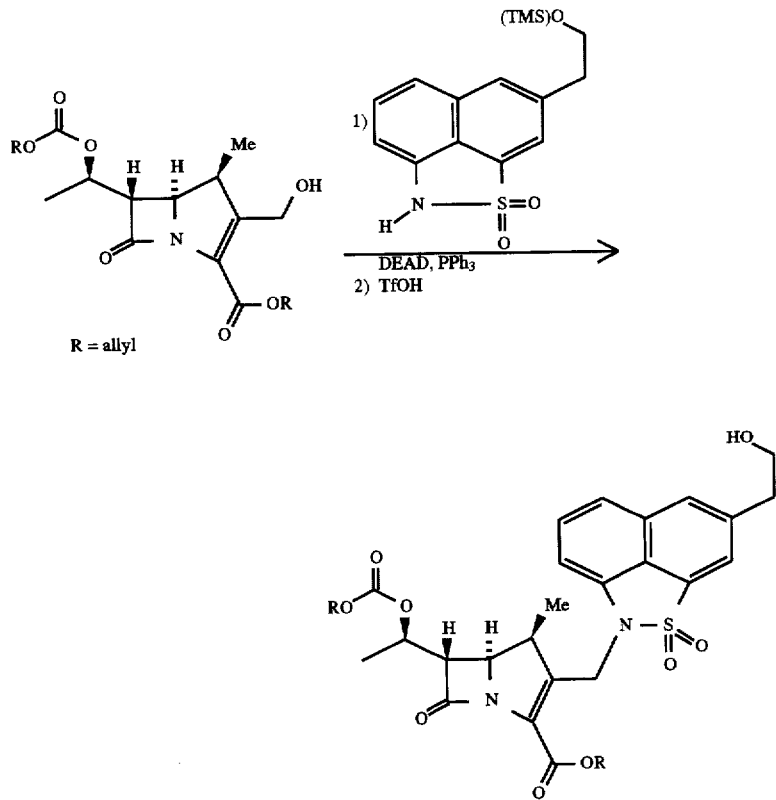

Steps 1 and 2 allyl(1S,5R,6S)-2-(3-(2-(hydroxy)-ethyl-1,8-naphthosultam)methyl)-6-[1(R)-(allyloxycarbonyl)oxyethyl]-1-methylcarbapen-2-em-3-carboxylate By appropriately modifying the procedures of Steps 1 and 2 of Example 6, allyl(1S,5R,6S)-2-(hydroxymethyl)-6-[1(R)-(allyloxycarbonyl)oxyethyl]-1-methylcarbapen-2-em-3-carboxylate is reacted with 3-(2-trimethylsilyloxyeth-1-yl)-1,8-naphthosultam to afford allyl(1S,5R,6S)-2-[N-(3-(2-hydroxy)-ethyl)-1,8-naphthosultam)methyl]-6-[(1R)-(allyloxycarbonyloxy)ethyl]-1-methylcarbapen-2-em-3-carboxylate.

EXAMPLES 45–47

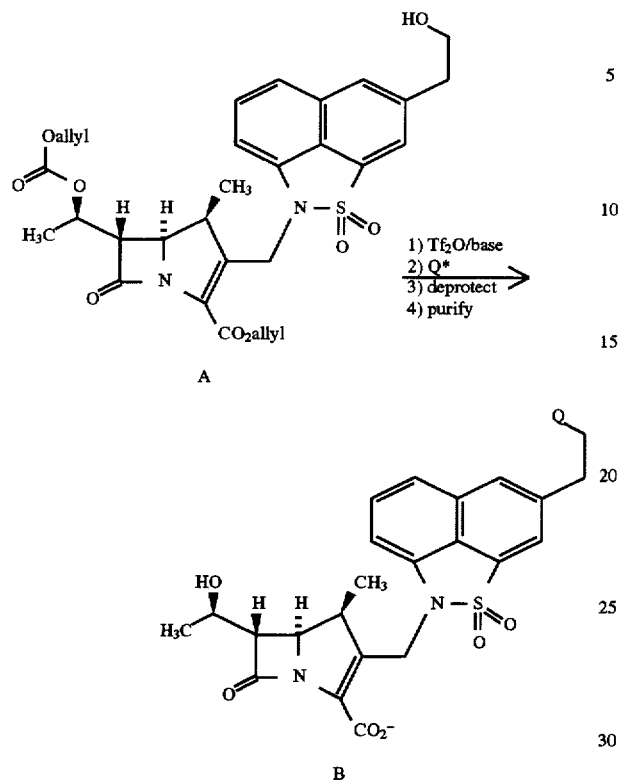

By appropriately modifying the procedures of Example 7 and 8, allyl(1S,5R,6S)-2-[N-(3-(2-hydroxy)-ethyl)-1,8-naphthosultam)methyl]-6-[(1R)-(allyloxycarbonyloxy)ethyl]-1-methylcarbapen-2-em-3-carboxylate (compound A) is reacted with compound Q* as set forth in the following Table to produce compounds of formula B in which Q is as defined in the following Table.

TABLE

| # | Q* | Q | # | Q* | Q | # | Q* | Q |
|---|----|----|---|----|----|---|----|----|
| 45 | ![NH2, TfO−, piperazinium] | ![NH2, Cl−, piperazinium] | 46 | ![HO, TfO−, piperazinium] | ![HO, Cl−, piperazinium] | 47 | ![CH3, N-imidazole] | ![CH3, N+-imidazole] |

EXAMPLE 48

SYNTHESIS OF ALLYL(1S,5R,6S)-2-(2-(HYDROXYMETHYL-1,8-NAPHTHOSULTAM)METHYL)-6-[1(R)-(ALLYLOXYCARBONYL)OXYETHYL]-1-METHYLCARBAPEN-2-EM-3-CARBOXYLATE

Steps 1 and 2 allyl(1S,5R,6S)-2-(2-(hydroxymethyl-1,8-naphthosultam) methyl)-6-[1(R)-(allyloxycarbonyl)oxyethyl]-1-methylcarbapen-2-em-3-carboxylate By appropriately modifying the procedures of Steps 1 and 2 of Example 1, allyl(1S,5R,6S)-2-(hydroxymethyl)-6-[1(R)-(allyloxycarbonyl)oxyethyl]-1-methylcarbapen-2-em-3-carboxylate is reacted with 2-(trimethylsilyloxymethyl)-1,8-naphthosultam to afford allyl(1S,5R,6S)-2-[N-(2-(hydroxymethyl)-1,8-naphthosultam)-methyl]-6-[(1R)-(allyloxycarbonyloxy)ethyl]-1-methylcarbapen-2-em-3-carboxylate.

EXAMPLES 49–51

EXAMPLES 52–54

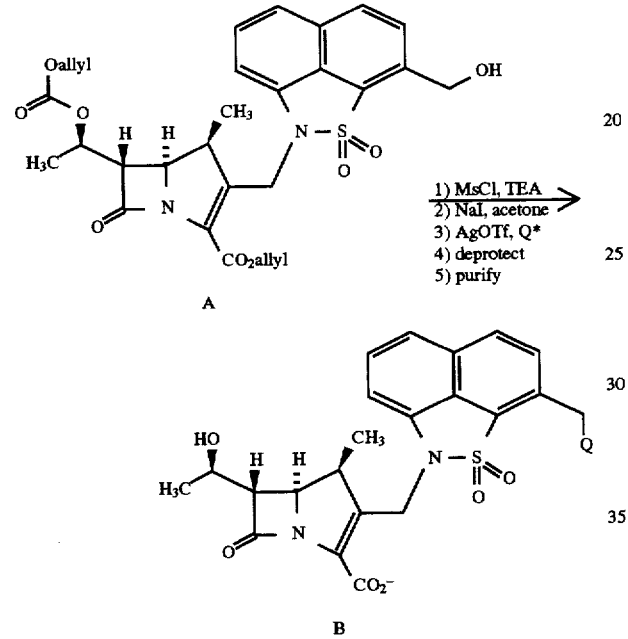

By appropriately modifying the procedures of Steps 3 and 4 of Example 1, allyl(1S,5R,6S)-2-[N-(2-(hydroxymethyl)-1,8-naphthosultam)-methyl]-6-[(1R)-(allyloxycarbonyloxy)ethyl]-1-methylcarbapen-2-em-3-carboxylate (compound A) is reacted with compound Q* as set forth in the following Table to produce compounds of formula B in which Q is as defined in the following Table.

By appropriately modifying the procedure of Example 3, allyl(1S,5R,6S)-2-[N-(2-(hydroxymethyl)-1,8-naphthosultam)methyl]-6-[(1R)-(allyloxycarbonyloxy)ethyl]-1-methylcarbapen-2-em-3-carboxylate (compound A) is reacted with compound Q* as set forth in the following Table to produce compounds of formula B in which Q is as defined in the following Table.

TABLE

| # | Q* | Q | # | Q* | Q | # | Q* | Q |
|---|----|----|----|----|----|----|----|----|
| 52 | ![CH3-N imidazole] | ![CH3-N+ imidazole] | 53 | ![OH-ethyl-N imidazole] | ![OH-ethyl-N+ imidazole] | 54 | ![S-thiazole-N] | ![S-thiazole-N+] |

EXAMPLE 55

SYNTHESIS OF ALLYL(1S,5R,6S)-2-(2-(2-(HYDROXY)-ETHYL-1,8-NAPHTHOSULTAM)METHYL)-6-[1(R)-(ALLYLOXYCARBONYL)OXYETHYL]-1-METHYLCARBAPEN-2-EM-3-CARBOXYLATE

By appropriately modifying the procedures of Steps 1 and 2 of Example 6, allyl(1S,5R,6S)-2-(hydroxymethyl)-6-[1(R)-(allyloxycarbonyl)oxyethyl]-1-methylcarbapen-2-em-3-carboxylate is reacted with 2-(2-trimethylsilyloxyeth-1-yl)-1,8-naphthosultam to afford allyl(1S,5R,6S)-2-[N-(2-(2-hydroxy)-ethyl)-1,8-naphthosultam)methyl]-6-[(1R)-(allyloxycarbonyloxy)ethyl]-1-methylcarbapen-2-em-3-carboxylate.

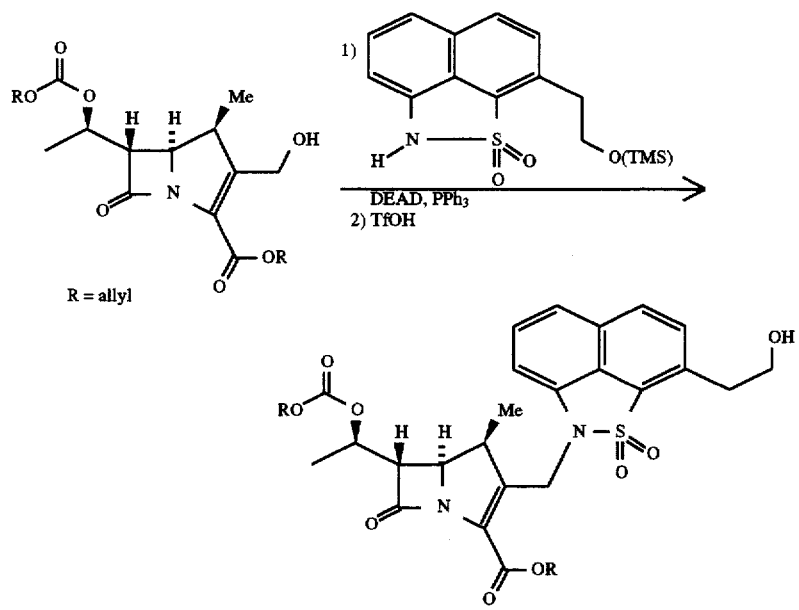

Steps 1 and 2 allyl(1S,5R,6S)-2-(2-(2-(hydroxy)-ethyl-1,8-naphthosultam)methyl)-6-[1(R)-(allyloxycarbonyl)oxyethyl]-1-methylcarbapen-2-em-3-carboxylate

EXAMPLES 56-58

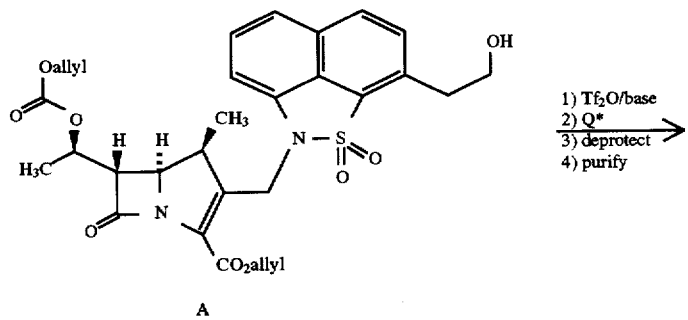

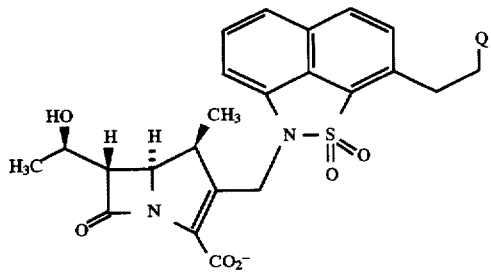

By appropriately modifying the procedures of Example 7 and 8, allyl(1S,5R,6S)-2-[N-(2-(2-hydroxy)-ethyl)-1,8-naphthosultam)methyl]-6-[(1R)-(allyloxycarbonyloxy)ethyl]-1-methylcarbapen-2-em-3-carboxylate (compound A) is reacted with compound Q* as set forth in the following Table to produce compounds of formula B in which Q is as defined in the following Table.

TABLE

| # | Q* | Q | # | Q* | Q | # | Q* | Q |
|---|----|----|---|----|----|---|----|----|
| 56 | TfO⁻, piperazinium-CH₂-C(=O)-NH₂ | Cl⁻, piperazinium-CH₂-C(=O)-NH₂ | 57 | TfO⁻, piperazinium-CH₂CH₂-OH | Cl⁻, piperazinium-CH₂CH₂-OH | 58 | N-methylimidazole | N-methylimidazolium |

EXAMPLE 59

SYNTHESIS OF ALLYL(1S,5R,6S)-2-(6-(HYDROXYMETHYL-1,8-NAPHTHOSULTAM)METHYL)-6-[1(R)-(ALLYLOXYCARBONYL)OXYETHYL]-1-METHYLCARBAPEN-2-EM-3-CARBOXYLATE

Steps 1 and 2
allyl(1S,5R,6S)-2-(6-(hydroxymethyl-1,8-naphthosultam) methyl)-6-[1(R)-(allyloxycarbonyl)oxyethyl]-1-methylcarbapen-2-em-3-carboxylate By appropriately modifying the procedures of Steps 1 and 2 of Example 1, allyl(1S,5R,6S)-2-(hydroxymethyl)-6-[1(R)-(allyloxycarbonyl)oxyethyl]-1-methylcarbapen-2-em-3-carboxylate is reacted with 6-(trimethylsilyloxymethyl)-1,8-naphthosultam to afford allyl(1S,5R,6S)-2-[N-(6-(hydroxymethyl)-1,8-naphthosultam)-methyl]-6-[(1R)-(allyloxycarbonyloxy)ethyl]-1-methylcarbapen-2-em-3-carboxylate.

TABLE

| # | Q* | Q | # | Q* | Q | # | Q* | Q |
|---|----|----|---|----|----|---|----|----|
| 60 | TfO⁻ NH₂-piperidinium-acetyl | Cl⁻ NH₂-piperidinium-acetyl | 61 | TfO⁻ HO-ethyl-piperidinium | Cl⁻ HO-ethyl-piperidinium | 62 | TfO⁻ F-ethyl-piperidinium | Cl⁻ F-ethyl-piperidinium |

EXAMPLES 60–62

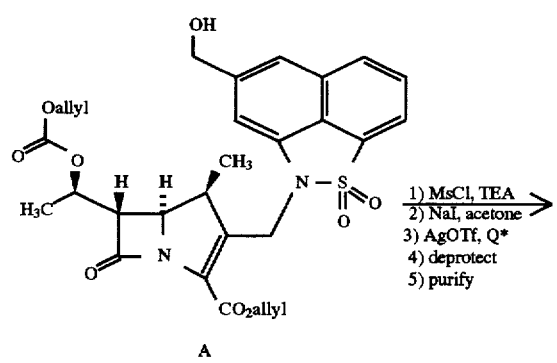

By appropriately modifying the procedures of Steps 3 and 4 of Example 1, allyl(1S,5R,6S)-2-[N-(6-(hydroxymethyl)-1,8-naphthosultam)-methyl]-6-[(1R)-(allyloxycarbonyloxy)ethyl]-1-methylcarbapen-2-em-3-carboxylate (compound A) is reacted with compound Q* as set forth in the following Table to produce compounds of formula B in which Q is as defined in the following Table.

EXAMPLES 63–65

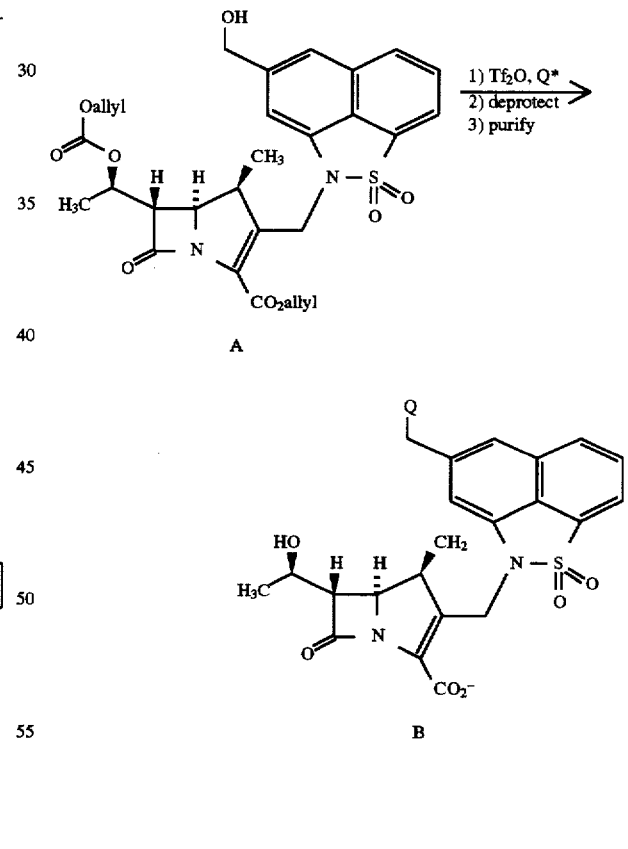

By appropriately modifying the procedure of Example 3, allyl(1S,5R,6S)-2-[N-(6-(hydroxymethyl)-1,8-naphthosultam)-methyl]-6-[(1R)-(allyloxycarbonyloxy)ethyl]-1-methylcarbapen-2-em-3-carboxylate (compound A) is reacted with compound Q* as set forth in the following Table to produce compounds of formula B in which Q is as defined in the following Table.

TABLE

| # | Q* | Q | # | Q* | Q | # | Q* | Q |
|---|---|---|---|---|---|---|---|---|
| 63 | ![imidazole N-CH3] | ![imidazolium N-CH3] | 64 | ![imidazole N-CH2CH2OH] | ![imidazolium N-CH2CH2OH] | 65 | ![oxazole] | ![oxazolium] |

EXAMPLE 66

SYNTHESIS OF ALLYL(1S,5R,6S)-2-(6-(2-(HYDROXY)-ETHYL-1,8-NAPHTHOSULTAM)METHYL)-6-[1(R)-(ALLYLOXYCARBONYL)OXYETHYL]-1-METHYLCARBAPEN-2-EM-3-CARBOXYLATE

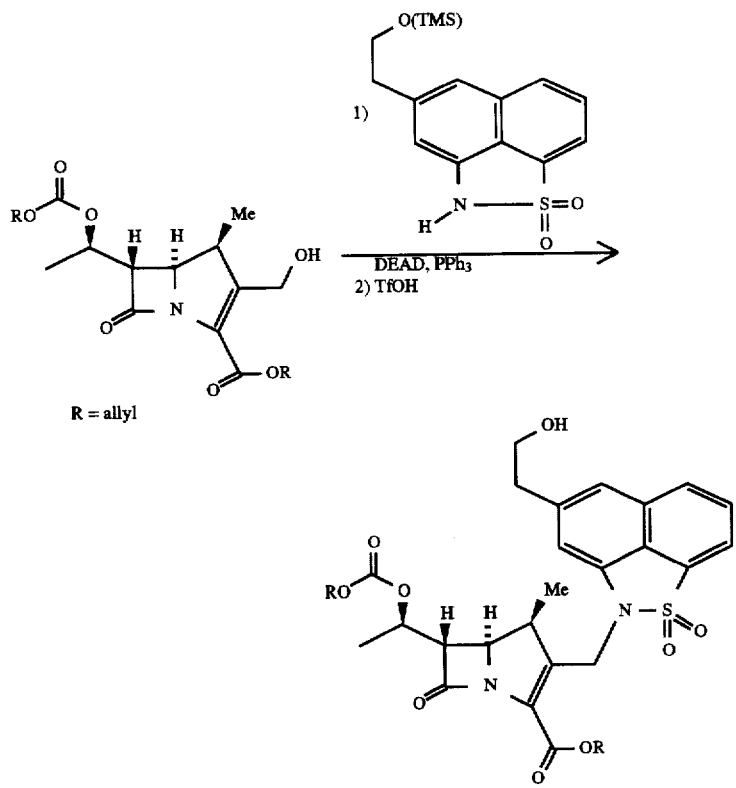

R = allyl

Steps 1 and 2 allyl(1S,5R,6S)-2-(6-(2-(hydroxy)-ethyl-1,8-naphthosultam)methyl)-6-[1(R)-(allyloxycarbonyl)oxyethyl]-1-methylcarbapen-2-em-3-carboxylate By appropriately modifying the procedures of Steps 1 and 2 of Example 6, allyl(1S,5R,6S)-2-(hydroxymethyl)-6-[1(R)-(allyloxycarbonyl)oxyethyl]-1-methylcarbapen-2-em-3-carboxylate is reacted with 6-(2-trimethylsilyloxyeth-1-yl)-1,8-naphthosultam to afford allyl(1S,5R,6S)-2-[N-(6-(2-hydroxy)-ethyl)-1,8-naphthosultam)methyl]-6-[(1R)-(allyloxycarbonyloxy)ethyl]-1-methylcarbapen-2-em-3-carboxylate.

EXAMPLES 67–69

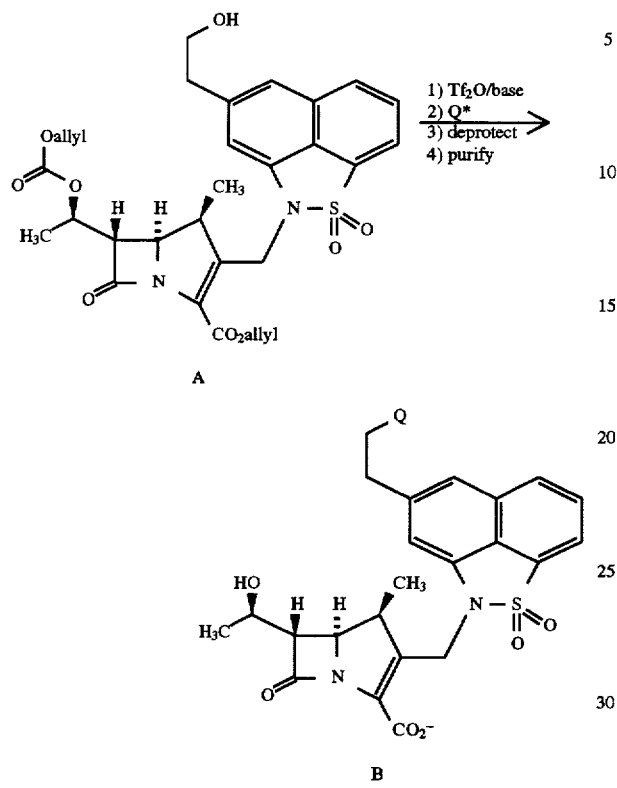

By appropriately modifying the procedures of Example 7 and 8, allyl(1S,5R,6S)-2-[N-(6-(2-hydroxy)-ethyl)-1,8-naphthosultam)methyl]-6-[(1R)-(allyloxycarbonyloxy)ethyl]-1-methylcarbapen-2-em-3-carboxylate (compound A) is reacted with compound Q* as set forth in the following Table to produce compounds of formula B in which Q is as defined in the following Table.

TABLE

| # | Q* | Q | # | Q* | Q | # | Q* | Q |
|---|----|----|---|----|----|---|----|----|
| 67 | TfO⁻ piperidinium-CH₂-C(O)-NH₂ | Cl⁻ piperidinium-CH₂-C(O)-NH₂ | 68 | TfO⁻ HO-CH₂CH₂-piperidinium | Cl⁻ HO-CH₂CH₂-piperidinium | 69 | N-methylimidazole | N-methylimidazolium |

EXAMPLE 70
SYNTHESIS OF ALLYL(1S,5R,6S)-2-(7-(HYDROXYMETHYL-1,8-NAPHTHOSULTAM) METHYL)-6-[1(R)-(ALLYLOXYCARBONYL) OXYETHYL]-1-METHYLCARBAPEN-2-EM-3-CARBOXYLATE

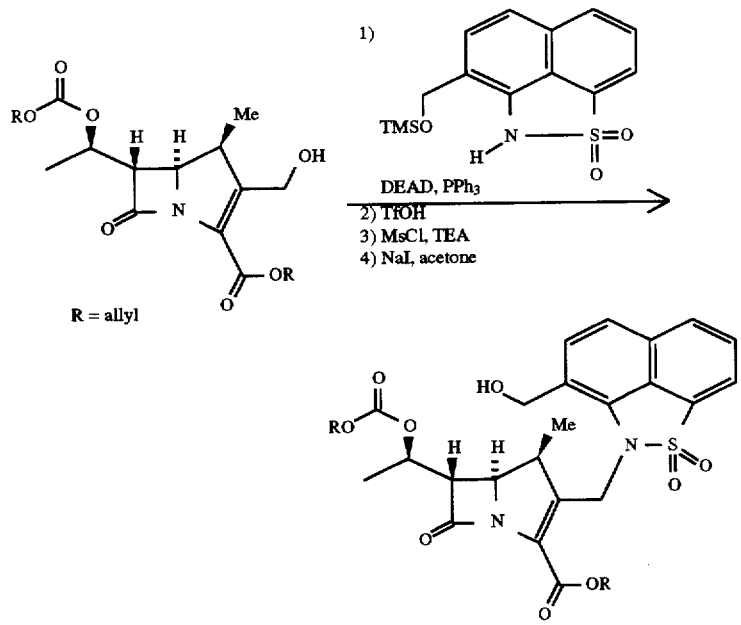

Steps 1 and 2
allyl(1S,5R,6S)-2-(7-(hydroxymethyl-1,8-naphthosultam) methyl)-6-[1(R)-(allyloxycarbonyl)oxyethyl]-1-methylcarbapen-2-em-3-carboxylate By appropriately modifying the procedures of Steps 1 and 2 of Example 1, allyl(1S,5R,6S)-2-(hydroxymethyl)-6-[1(R)-(allyloxycarbonyl)oxyethyl]-1-methylcarbapen-2-em-3-carboxylate is reacted with 7-(trimethylsilyloxymethyl)-1,8-naphthosultam to afford allyl(1S,5R,6S)-2-[N-(7-(hydroxymethyl)-1,8-naphthosultam)-methyl]-6-[(1R)-(allyloxycarbonyloxy)ethyl]-1-methylcarbapen-2-em-3-carboxylate.

EXAMPLES 71–73

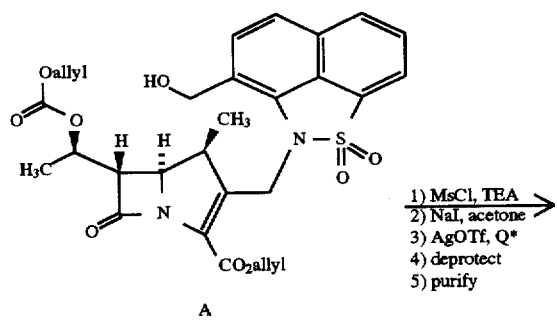

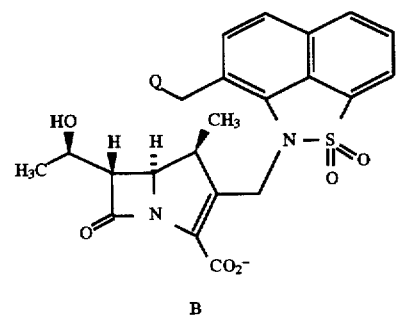

By appropriately modifying the procedures of Steps 3 and 4 of Example 1, allyl(1S,5R,6S)-2-[N-(7-(hydroxymethyl)-1,8-naphthosultam)-methyl]-6-[(1R)-(allyloxycarbonyloxy) ethyl]-1-methylcarbapen-2-em-3-carboxylate (compound A) is reacted with compound Q* as set forth in the following Table to produce compounds of formula B in which Q is as defined in the following Table.

TABLE

| # | Q* | Q | # | Q* | Q | # | Q* | Q |
|---|----|----|---|----|----|---|----|----|
| 71 | TfO⁻ [structure with NH₂] | Cl⁻ [structure with NH₂] | 72 | TfO⁻ [structure with HO] | Cl⁻ [structure with HO] | 73 | TfO⁻ [structure with F] | Cl⁻ [structure with F] |

EXAMPLES 74–76

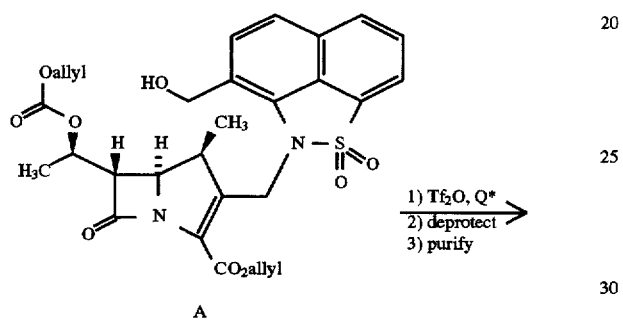

By appropriately modifying the procedure of Example 3, allyl(1S,5R,6S)-2-[N-(7-(hydroxymethyl)-1,8-naphthosultam)-methyl]-6-[(1R)-(allyloxycarbonyloxy)ethyl]-1-methylcarbapen-2-em-3-carboxylate (compound A) is reacted with compound Q* as set forth in the following Table to produce compounds of formula B in which Q is as defined in the following Table.

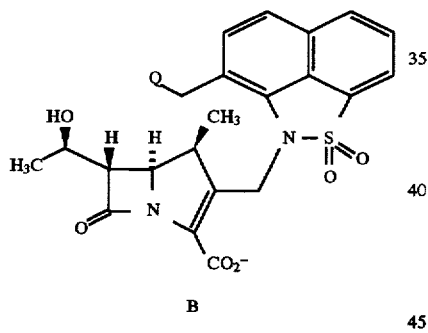

TABLE

| # | Q* | Q | # | Q* | Q | # | Q* | Q |
|---|----|----|---|----|----|---|----|----|
| 74 | [imidazole CH₃] | [imidazolium CH₃] | 75 | [imidazole OH] | [imidazolium OH] | 76 | [imidazole O] | [imidazolium O] |

EXAMPLE 77

SYNTHESIS OF ALLYL(1S,5R,6S)-2-(7-(2-(HYDROXY)-ETHYL-1,8-NAPHTHOSULTAM) METHYL)-6-[1(R)-(ALLYLOXYCARBONYL) OXYETHYL]-1-METHYLCARBAPEN-2-EM-3-CARBOXYLATE

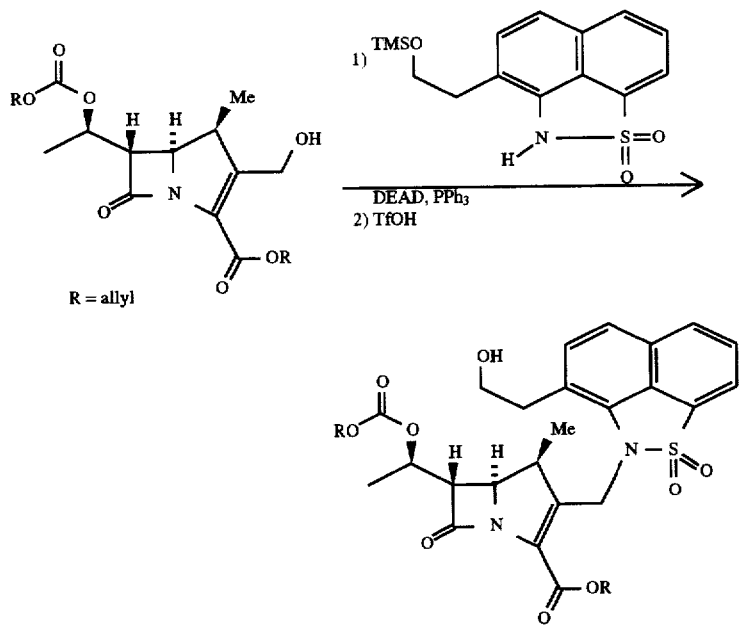

R = allyl

Steps 1 and 2 allyl(1S,5R,6S)-2-(7-(2-(hydroxy)-ethyl-1,8-naphthosultam)methyl)-6-[1(R)-(allyloxycarbonyl)oxyethyl]-1-methylcarbapen-2-em-3-carboxylate By appropriately modifying the procedures of Steps 1 and 2 of Example 6, allyl(1S,5R,6S)-2-(hydroxymethyl)-6-[1(R)-(allyloxycarbonyl)oxyethyl]-1-methylcarbapen-2-em-3-carboxylate is reacted with 7-(2-trimethylsilyloxyeth-1-yl)-1,8-naphthosultam to afford allyl(1S,5R,6S)-2-[N-(7-(2-hydroxy)-ethyl)-1,8-naphthosultam)methyl]-6-[(1R)-(allyloxycarbonyloxy)ethyl]-1-methylcarbapen-2-em-3-carboxylate.

EXAMPLES 78–80

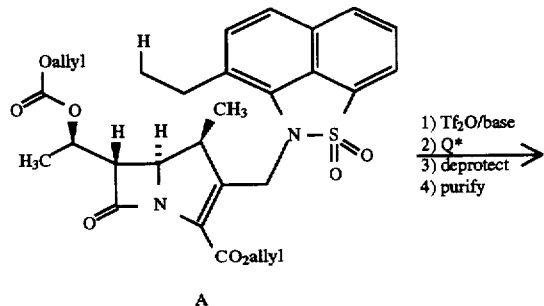

A

1) Tf₂O/base
2) Q*
3) deprotect
4) purify

-continued

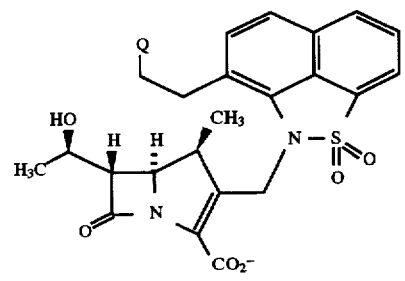

B

By appropriately modifying the procedures of Example 7 and 8, allyl(1S,5R,6S)-2-[N-(7-(2-hydroxy)-ethyl)-1,8-naphthosultam)methyl]-6-[(1R)-(allyloxycarbonyloxy)ethyl]-1-methylcarbapen-2-em-3-carboxylate (compound A) is reacted with compound Q* as set forth in the following Table to produce compounds of formula B in which Q is as defined in the following Table.

TABLE

| # | Q* | Q | # | Q* | Q | # | Q* | Q |
|---|---|---|---|---|---|---|---|---|
| 78 | TfO⁻ ⟨piperazinium-CH₂C(O)NH₂⟩ | Cl⁻ ⟨piperazinium-CH₂C(O)NH₂⟩ | 79 | TfO⁻ ⟨piperazinium-CH₂CH₂OH⟩ | Cl⁻ ⟨piperazinium-CH₂CH₂OH⟩ | 80 | ⟨N-methylimidazole⟩ | ⟨N-methylimidazolium⟩ |

EXAMPLE 81

SYNTHESIS OF ALLYL(1S,5R,6S)-2-(4-(2-(HYDROXY)-ETHYL-5-NITRO-1,8-NAPHTHOSULTAM)METHYL)-6-[1(R)-(ALLYLOXYCARBONYL)OXYETHYL]-1-METHYLCARBAPEN-2-EM-3-CARBOXYLATE

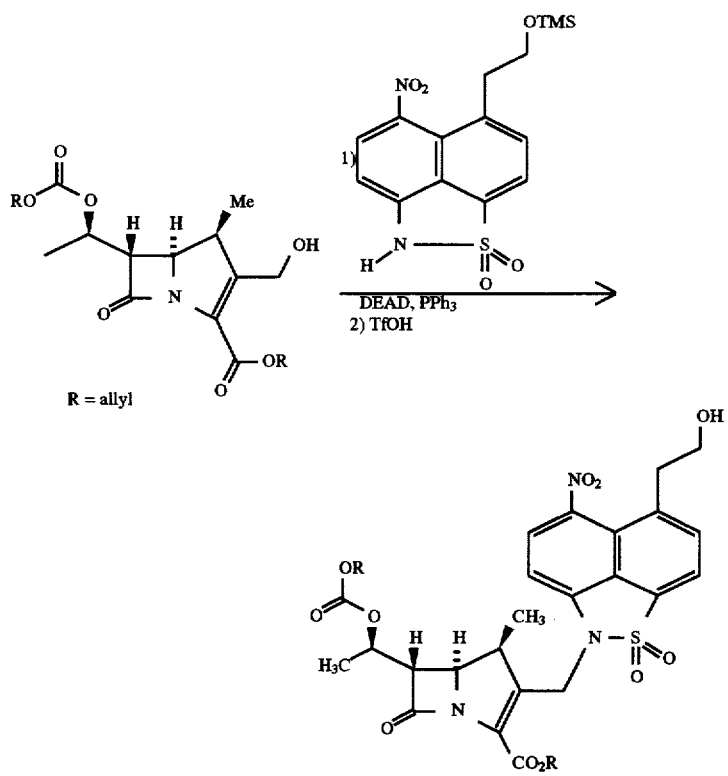

R = allyl

Steps 1 and 2 allyl(1S,5R,6S)-2-(4-(2-(hydroxy)-ethyl-5-nitro-1,8-naphthosultam)methyl)-6-[1(R)-(allyloxycarbonyl)oxyethyl]-1-methylcarbapen-2-em-3-carboxylate By appropriately modifying the procedures of Steps 1 and 2 of Example 6, allyl(1S,5R,6S)-2-(hydroxymethyl)-6-[1(R)-(allyloxycarbonyl)oxyethyl]-1-methylcarbapen-2-em-3-carboxylate is reacted with 4-(2-trimethylsilyloxyeth-1-yl)-5-nitro-1,8-naphthosultam to afford allyl(1S,5R,6S)-2-[N-(4-(2-hydroxy)-ethyl)-5-nitro-1,8-naphthosultam)-methyl]-6-[(1R)-(allyloxycarbonyloxy)ethyl]-1-methylcarbapen-2-em-3-carboxylate.

EXAMPLES 82–84

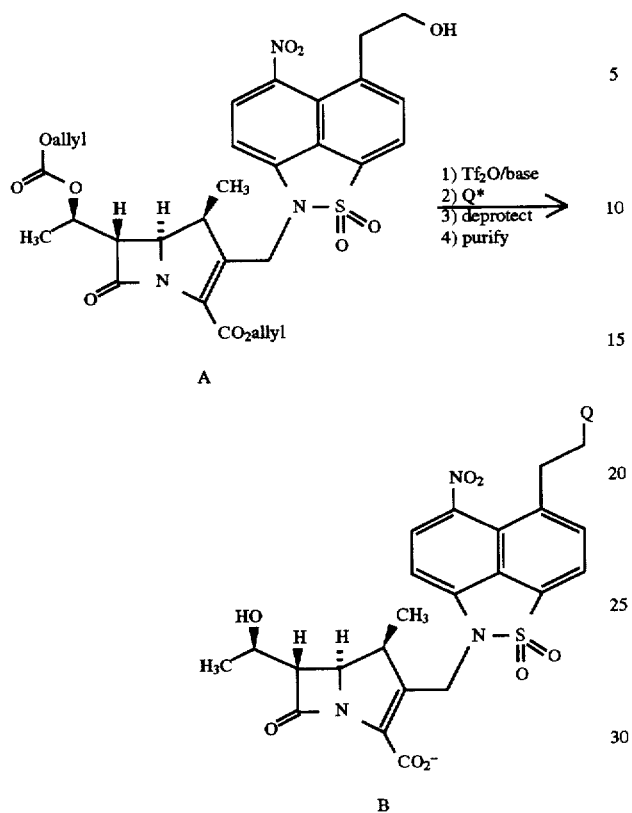

By appropriately modifying the procedures of Example 7 and 8, allyl(1S,5R,6S)-2-[N-(4-(2-hydroxy)-ethyl)-5-nitro-1,8-naphthosultam)-methyl]-6-[(1R)-(allyloxycarbonyloxy)ethyl]-1-methylcarbapen-2-em-3-carboxylate (compound A) is reacted with compound Q* as set forth in the following Table to produce compounds of formula B in which Q is as defined in the following Table.

| TABLE | | | | | | | | |
|---|---|---|---|---|---|---|---|---|
| # | Q* | Q | # | Q* | Q | # | Q* | Q |
| 82 | TfO⁻, NH₂-CH₂-C(=O)-N⁺(piperidine-N) | Cl⁻, NH₂-CH₂-C(=O)-N⁺(piperidine-N-) | 83 | HO-CH₂CH₂-N⁺(piperazine), TfO⁻ | HO-CH₂CH₂-N⁺(piperazine-N-) Cl⁻ | 84 | CH₃-N(imidazole)- | CH₃-N(imidazole-N⁺-)- |

EXAMPLE 85
SYNTHESIS OF ALLYL(1S,5R,6S)-2-(4-(2-(HYDROXY)-ETHYL-5-METHOXYACETYL-1,8-NAPHTHOSULTAM)METHYL)-6-[1(R)-(ALLYLOXYCARBONYL)OXYETHYL]-1-METHYLCARBAPEN-2-EM-3-CARBOXYLATE

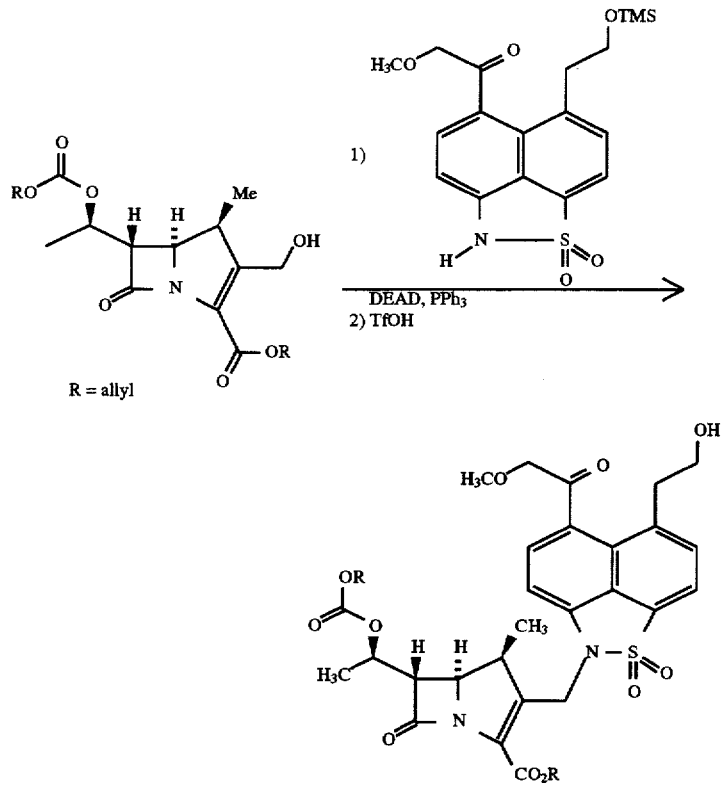

Steps 1 and 2
allyl(1S,5R,6S)-2-(4-(2-(hydroxy)-ethyl-5-methoxyacetyl-1,8-naphthosultam)methyl)-6-[1(R)-(allyloxycarbonyl)oxyethyl]-1-methylcarbapen-2-em-3-carboxylate By appropriately modifying the procedures of Steps 1 and 2 of Example 6, allyl(1S,5R,6S)-2-(hydroxymethyl)-6-[1(R)-(allyloxycarbonyl)oxyethyl]-1-methylcarbapen-2-em-3-carboxylate is reacted with 4-(2-trimethylsilyloxyeth-1-yl)-5-methoxyacetyl-1,8-naphthosultam to afford allyl(1S,5R,6S)-2-[N-(4-(2-hydroxy)-ethyl)-5-methoxyacetyl-1,8-naphthosultam)-methyl]-6-[(1R)-(allyloxycarbonyloxy)ethyl]-1-methylcarbapen-2-em-3-carboxylate.

EXAMPLES 86–88

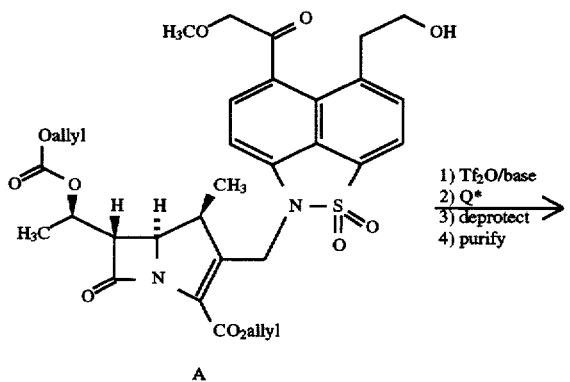

A

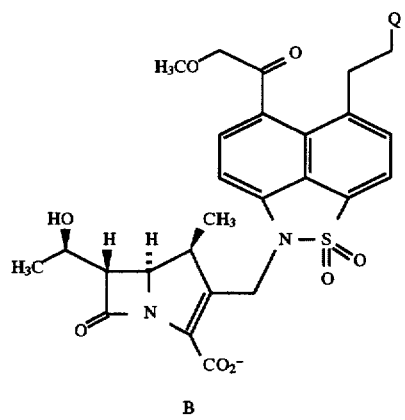

B

By appropriately modifying the procedures of Example 7 and 8, allyl(1S,5R,6S)-2-[N-(4-(2-hydroxy)-ethyl)-5-methoxyacetyl-1,8-naphthosultam)-methyl]-6-[(1R)-(allyloxycarbonyloxy)ethyl]-1-methylcarbapen-2-em-3-carboxylate (compound A) is reacted with compound Q* as set forth in the following Table to produce compounds of formula B in which Q is as defined in the following Table.

TABLE

| # | Q* | Q | # | Q* | Q | # | Q* | Q |
|---|---|---|---|---|---|---|---|---|
| 86 | 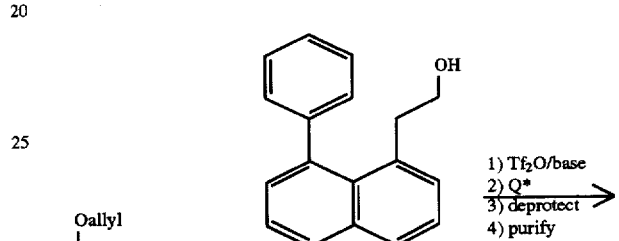 | | 87 | | | 88 | | |

EXAMPLE 89

SYNTHESIS OF ALLYL(1S,5R,6S)-2-(4-(2-(HYDROXY)-ETHYL-5-PHENYL-1,8-NAPHTHOSULTAM)METHYL)-6-[1(R)-(ALLYLOXYCARBONYL)OXYETHYL]-1-METHYLCARBAPEN-2-EM-3-CARBOXYLATE

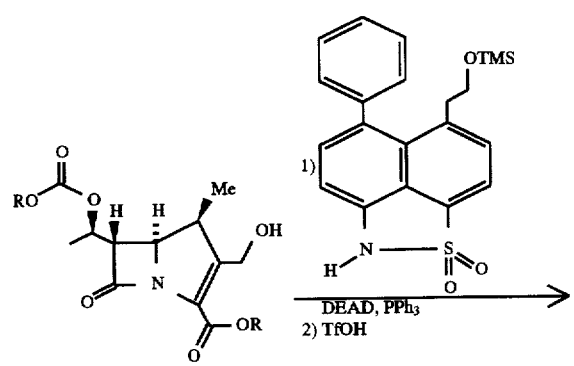

R = allyl

EXAMPLES 90–92

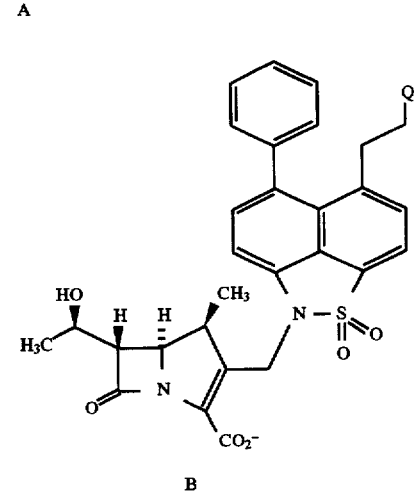

Steps 1 and 2
allyl(1S,5R,6S)-2-(4-(2-(hydroxy)-ethyl-5-phenyl-1,8-naphthosultam)methyl)-6-[1(R)-(allyloxycarbonyl)oxyethyl]-1-methylcarbapen-2-em-3-carboxylate By appropriately modifying the procedures of Steps 1 and 2 of Example 6, allyl(1S,5R,6S)-2-(hydroxymethyl)-6-[1(R)-(allyloxycarbonyl)oxyethyl]-1-methylcarbapen-2-em-3-carboxylate is reacted with 4-(2-trimethylsilyloxyeth-1-yl)-5-phenyl-1,8naphthosultam to afford allyl(1S,5R,6S)-2-[N-(4-(2-hydroxy)ethyl)-5-phenyl-1,8-naphthosultam)-methyl]-6-[(1R)-(allyloxycarbonyloxy)ethyl]-1-methylcarbapen-2-em-3-carboxylate.

By appropriately modifying the procedures of Example 7 and 8, allyl(1S,5R,6S)-2-[N-(4-(2-hydroxy)-ethyl)-5-methoxyacetyl-1,8-naphthosultam)-methyl]-6-[(1R)-(allyloxycarbonyloxy)ethyl]-1-methylcarbapen-2-em-3-carboxylate (compound A) is reacted with compound Q* as set forth in the following Table to produce compounds of formula B in which Q is as defined in the following Table.

TABLE
| # | Q* | Q | # | Q* | Q | # | Q* | Q |
|---|----|----|---|----|----|---|----|----|
| 90 | TfO⁻ [structure with NH₂, C=O, N⁺ piperazine] | Cl⁻ [structure with NH₂, C=O, N⁺ piperazine] | 91 | TfO⁻ [HO-CH₂CH₂-N⁺ piperazine] | Cl⁻ [HO-CH₂CH₂-N⁺ piperazine] | 92 | [N-methyl imidazole with CH₃] | [N-methyl imidazolium with CH₃] |
EXAMPLE 93
SYNTHESIS OF (1S,5R,6S)-2-(4-((1 3-DIMETHYLIMIDAZOL-2-IUM)-1,8-NAPHTHOSULTAM)METHYL)-6-[1(R)-(ALLYLOXYCARBONYL)OXYETHYL]-1-METHYLCARBAPEN-2-EM-3-CARBOXYLATE
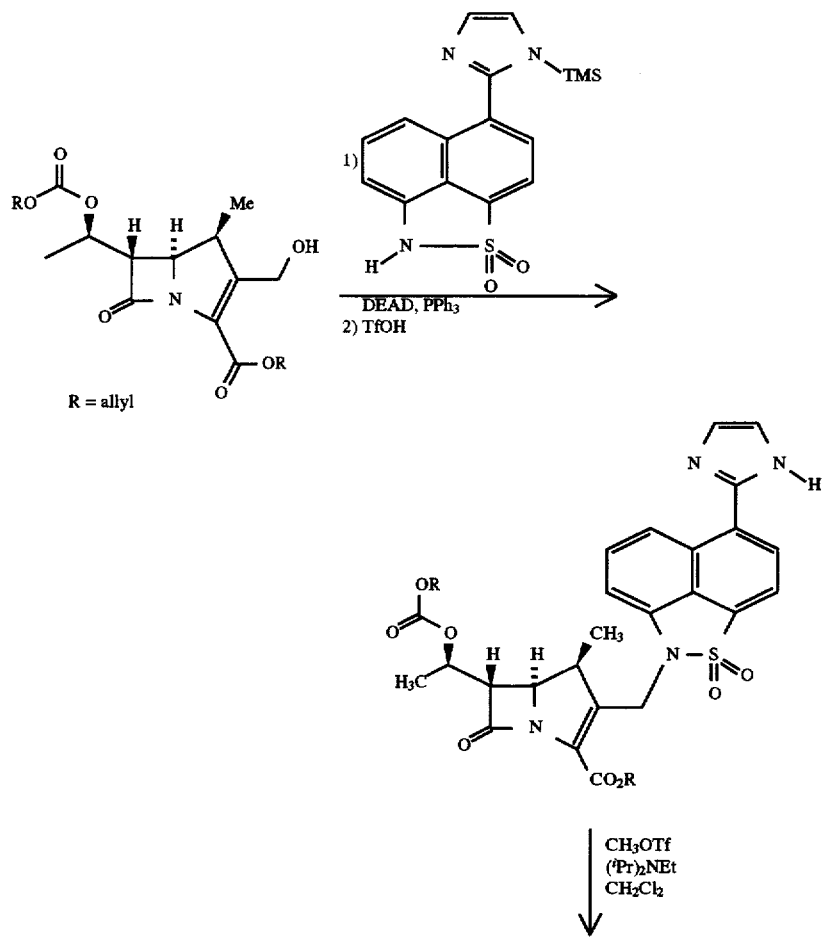

-continued

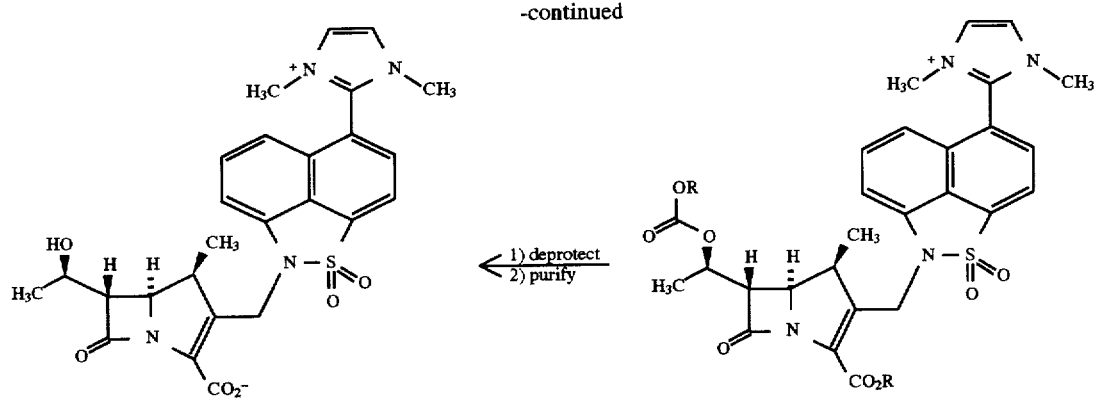

Steps 1 and 2 allyl(1S,5R,6S)-2-(4-(imidazol-2-yl)-1,8-naphthosultam)methyl)-6-[1(R)-(allyloxycarbonyl)oxyethyl]-1-methylcarbapen-2-em-3-carboxylate By appropriately modifying the procedures of Steps 1 and 2 of Example 6, allyl(1S,5R,6S)-2-(hydroxymethyl)-6-[1(R)-(allyloxycarbonyl)oxyethyl]-1-methylcarbapen-2-em-3-carboxylate is reacted with 4-(imidazol-2-yl)-1,8-naphthosultam to afford allyl (1S,5R,6S)-2-[N-(4-(imidazol-2-yl)-1,8-naphthosultam)-methyl]-6-[(1R)-(allyloxycarbonyloxy)ethyl]-1-methylcarbapen-2-em-3-carboxylate.

Step 3 allyl(1S,5R,6S)-2-(4-(1,3-dimethyl-imidazol-2-ium)-1,8-naphthosultam)methyl)-6-[1(R)-(allyloxycarbonyl)oxyethyl]-1-methylcarbapen-2-em-3-carboxylate trifluoromethanesulfonate Allyl(1S,5R,6S)-2-[N-(4-(imidazol-2-yl)-1,8-naphthosultam)-methyl]-6-[(1R)-(allyloxycarbonyloxy)ethyl]-1-methylcarbapen-2-em-3-carboxylate (0.10 mmol) and diisopropylethylamine (0.11 mmol) are dissolved in methylene chloride (5 mL) under a nitrogen atmosphere. The mixture is cooled in an ice bath and treated with methyl trifluoromethanesulfonate (0.21 mmol). After 30 minutes the mixture is removed from the cooling bath and allowed to warm to room temperature. The mixture is partitioned between methylene chloride (10 mL) and 0.1N pH7 potassium phosphate buffer (20 mL). The methylene chloride layer is washed again with 0.1N pH7 potassium phosphate buffer (20 mL), dried over magnesium sulfate, filtered, and evaporated to give the title compound.

Step 4

(1S,5R,6S)-2-(4-(1,3-dimethyl-imidazol-2-ium)-1,8-naphthosultam)methyl)-6-[1(R)-hydroxyethyl]-1-methylcarbapen-2-em-3-carboxylate The crude allyl(1S,5R,6S)-2-(4-(1,3-dimethyl-imidazol-2-ium)-1,8-naphthosultam)methyl)-6-[1(R)-(allyloxycarbonyl)oxyethyl]-1-methylcarbapen-2-em-3-carboxylate trifluoromethanesulfonate from the previous step is dissolved in dimethylformamide (1.5 mL) and cooled in an ice bath. A solution of 0.5M sodium ethyl hexanoate in ethyl acetate (0.22 mL, 0.11 mmol) and ethyl hexanoic acid (0.036 mL, 0.22 mmol) are added. The solution is blanketed with nitrogen, using a Firestone valve, and triphenylphosphine (0.033 mmol) and tetrakis(triphenylphosphine) palladium (0.033 mmol) are added. After 70 minutes, diethyl ether (10 mL) is added and the supernatant is decanted from the precipitate. The solid is washed with additional diethyl ether (10 mL) and dried under vacuum. The solid is purified on a 1000 micron reverse phase plate developed, in an ice bath, with 30% acetonitrile/water and eluted with 80% acetonitrile/water (15 mL). The eluent is diluted with de-ionized water (10 mL), washed with hexanes (40 mL), evaporated to approximately 2 mL and lyophilized to give the title compound.

EXAMPLE 94

SYNTHESIS OF (1S,5R,6S)-2-(4-((3-METHYLIMIDAZOL-1-IUM)-1,8-NAPHTHOSULTAM)METHYL)-6-[1(R)-(ALLYLOXYCARBONYL)OXYETHYL]-1-METHYLCARBAPEN-2-EM-3-CARBOXYLATE

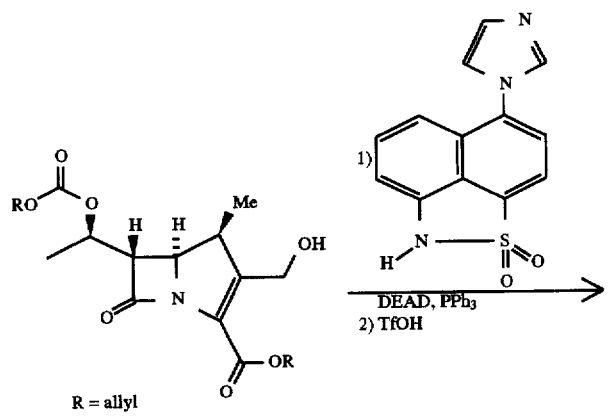

R = allyl

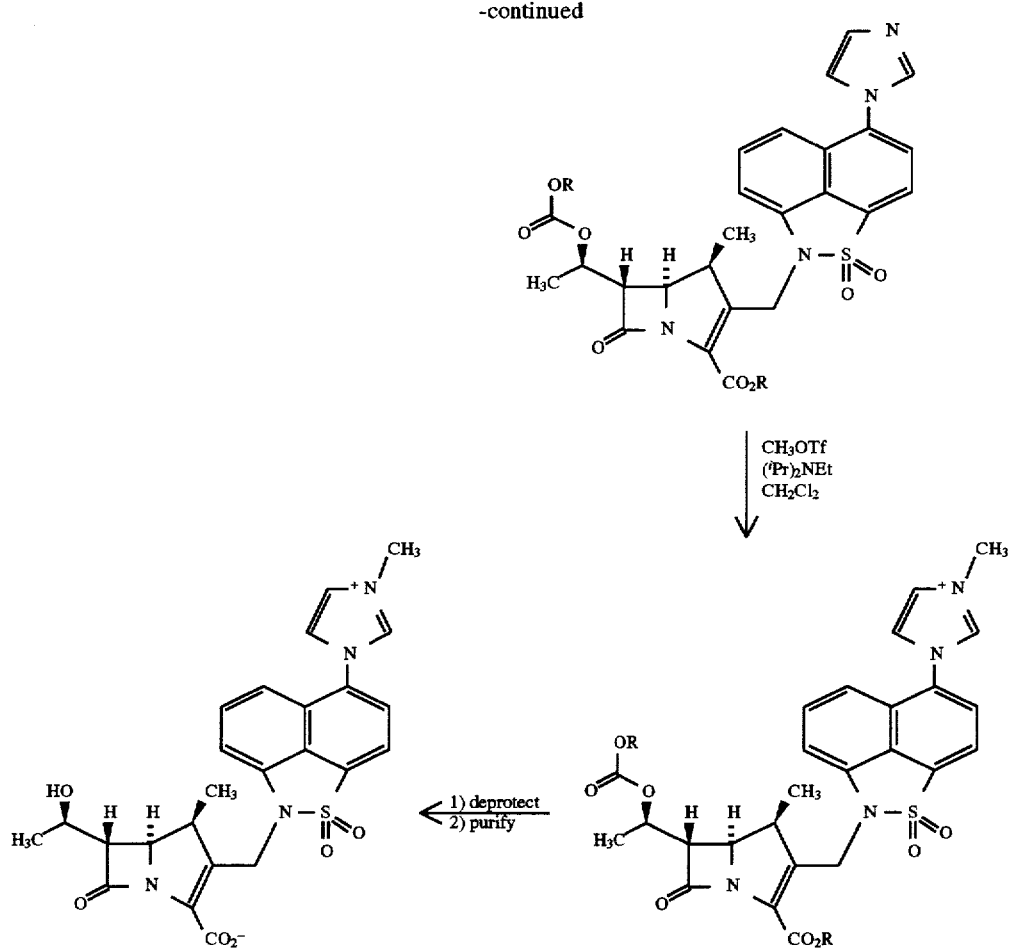

Steps 1 and 2
allyl(1S,5R,6S)-2-(4-(imidazol-1-yl)-1,8-naphthosultam) methyl)-6-[1(R)-(allyloxycarbonyl)oxyethyl]-1-methylcarbapen-2-em-3-carboxylate By appropriately modifying the procedures of Steps 1 and 2 of Example 6, allyl(1S,5R,6S)-2-(hydroxymethyl)-6-[1(R)-(allyloxycarbonyl)oxyethyl]-1-methylcarbapen-2-em-3-carboxylate is reacted with 4-(imidazol-1-yl)-1,8-naphthosultam to afford allyl (1S,5R,6S)-2-[N-(4-(imidazol-1-yl)-1,8-naphthosultam)-methyl]-6-[(1R)-(allyloxycarbonyloxy)ethyl]-1-methylcarbapen-2-em-3-carboxylate.

Step 3
allyl(1S,5R,6S)-2-(4-(3-methyl-imidazol-1-ium)-1,8-naphthosultam)methyl)-6-[1(R)-(allyloxycarbonyl)oxyethyl]-1-methylcarbapen-2-em-3-carboxylate trifluoromethanesulfonate By appropriately modifying the procedure of Step 3 of Example 93, allyl(1S,5R,6S)-2-[N-(4-(imidazol-1-yl)-1,8-naphthosultam)-methyl]-6-[(1R)-(allyloxycarbonyloxy)ethyl]-1-methylcarbapen-2-em-3-carboxylate is reacted with methyl trifluoromethanesulfonate to afford the title compound.

Step 4
(1S,5R,6S)-2-(4-(3-methyl-imidazol-1-ium)-1,8-naphthosultam)methyl)-6-[1(R)-hydroxyethyl]-1-methylcarbapen-2-em-3-carboxylate By appropriately modifying the procedure of Step 4 of Example 93, allyl(1S,5R,6S)-2-[N-(4-(3-methyl-imidazol-1-ium)-1,8-naphthosultam)-methyl]-6-[(1R)-(allyloxycarbonyloxy)ethyl]-1-methylcarbapen-2-em-3-carboxylate is deprotected and purified to afford the title compound.

What is claimed is:
1. A compound represented by formula I:

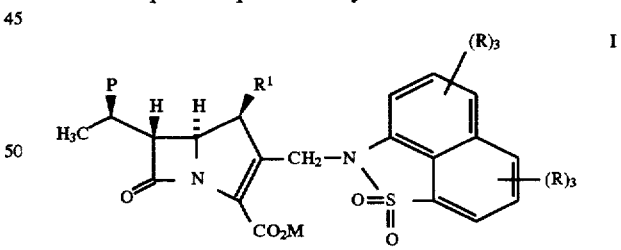

or a pharmaceutically acceptable salt thereof, wherein:
$R^1$ represents H or methyl;
$CO_2M$ represents a carboxylic acid, a carboxylate anion, a pharmaceutically acceptable ester group or a carboxylic acid protected by a protecting group;
P represents hydrogen, hydroxyl, F or hydroxyl protected by a hydroxyl-protecting group;
each R is independently selected from: —R*; —Q; hydrogen; halo; —CN; —$NO_2$; —$NR^aR^b$; —$OR^c$; —$SR^c$; —C(O)$NR^aR^b$; —C(O)$OR^h$; —S(O)$R^c$; —$SO_2R^c$; —$SO_2NR^aR^b$; —$NR^aSO_2R^b$; —C(O)$R^a$; —OC(O)$R^a$; —OC(O)$NR^aR^b$; —$NR^aC(O)NR^bR^c$; —$NR^aCO_2R^h$; —$OCO_2R^h$; —$NR^aC(O)R^b$; —$C_{1-6}$ straight- or branched-chain alkyl, unsubstituted or substituted with one to four $R^d$ groups; and —$C_{3-7}$ cycloalkyl, unsubstituted or substituted with one to four $R^d$ groups;

with the proviso that at least one R is present which contains at least one positive charge;

each $R^a$, $R^b$ and $R^c$ independently represents hydrogen, —R*, —$C_{1-6}$ straight- or branched-chain alkyl, unsubstituted or substituted with one to four $R^d$ groups, or —$C_{3-7}$ cycloalkyl, unsubstituted or substituted with one to four $R^d$ groups;

or $R^a$ and $R^b$ taken together with any intervening atoms represent a 4–6 membered saturated ring optionally interrupted by one or more of O, S, $NR^c$, with $R^c$ as defined above, or —C(O)—, said ring being unsubstituted or substituted with one to four $R^i$ groups;

or $R^b$ and $R^c$ taken together with any intervening atoms represent a 4–6 membered saturated ring optionally interrupted by one to three of O, S, $NR^a$, with $R^a$ as defined above, or —C(O)—, said ring being unsubstituted or substituted with one to four $R^i$ groups;

each $R^d$ independently represents halo; —CN; —$NO_2$; —$NR^eR^f$; —$OR^g$; —$SR^g$; —$CONR^eR^f$; —$COOR^g$; —$SOR^g$; —$SO_2R^g$; —$SO_2NR^eR^f$; —$NR^eSO_2R^f$; —$COR^e$; —$NR^eCOR^f$; —$OCOR^e$; —$OCONR^eR^f$; —$NR^eCONR^fR^g$; —$NR^eCO_2R^h$; —$OCO_2R^h$; —$C(NR^e)NR^fR^g$; —$NR^eC(NH)NR^fR^g$; —$NR^eC(NR^f)R^g$; —R* or —Q;

$R^e$, $R^f$ and $R^g$ represent hydrogen; —R*; —$C_{1-6}$ straight- or branched-chain alkyl unsubstituted or substituted with one to four $R^i$ groups;

or $R^e$ and $R^f$ taken together with any intervening atoms represent a 4–6 membered saturated ring optionally interrupted by one to three of O, S, —C(O)— or $NR^g$ with $R^g$ as defined above, said ring being unsubstituted or substituted with one to four $R^i$ groups;

each $R^i$ independently represents halo; —CN; —$NO_2$; phenyl; —$NHSO_2R^h$; —$OR^h$, —$SR^h$; —N($R^h$)$_2$; —$N^+$($R^h$)$_3$; —C(O)N($R^h$)$_2$; —$SO_2$N($R^h$)$_2$; heteroaryl; heteroarylium; —$CO_2R^h$; —C(O)$R^h$; —$OCOR^h$; —$NHCOR^h$; guanidinyl; carbamimidoyl or ureido;

each $R^h$ independently represents hydrogen, a —$C_{1-6}$ straight or branched-chain alkyl group, a —$C_3$–$C_6$ cycloalkyl group or phenyl, or when two $R^h$ groups are present, said $R^h$ groups may be taken in combination and represent a 4–6 membered saturated ring, optionally interrupted by one or two of O, S, $SO_2$, —C(O)—, NH and $NCH_3$;

Q is selected from the group consisting of:

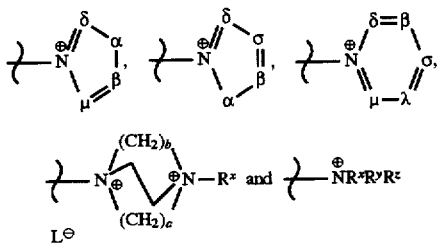

wherein:

a and b are 1, 2 or 3;

$L^-$ is a pharmaceutically acceptable counterion;

α represents O, S or $NR^s$;

β, δ, λ, μ and σ represent $CR^s$, N or $N^+R^s$, provided that no more than one of β, δ, λ, μ and σ is $N^+R^s$;

R* is selected from the group consisting of:

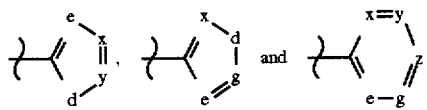

wherein:

d represents O, S or $NR^k$;

e, g, x, y and z represent $CR^m$, N or $N^+R^k$, provided that no more than one of e, g, x, y and z in any given structure represents $N^+R^k$;

$R^k$ represents hydrogen; —$C_{1-6}$ straight- or branched-chain alkyl, unsubstituted or substituted with one to four $R^i$ groups; or —$(CH_2)_nQ$ where n=1, 2 or 3 and Q is as previously defined;

each $R^m$ independently represents a member selected from the group consisting of: hydrogen; halo; —CN; —$NO_2$; —$NR^nR^o$; —$OR^n$; —$SR^n$; —$CONR^nR^o$; —$COOR^h$; —$SOR^n$; —$SO_2R^n$; —$SO_2NR^nR^o$; —$NR^nSO_2R^o$; —$COR^n$; —$NR^nCOR^o$; —$OCOR^n$; —$OCONR^nR^o$; —$NR^nCO_2R^h$; —$NR^nCONR^oR^h$; —$OCO_2R^h$; —$CNR^nNR^oR^h$; —$NR^nCNHNR^oR^h$; —$NR^nC(NRO)R^h$; —$C_{1-6}$ straight- or branched-chain alkyl, unsubstituted or substituted with one to four $R^i$ groups; —$C_{3-7}$ cycloalkyl, unsubstituted or substituted with one to four $R^i$ groups; and —$(CH_2)_nQ$ where n and Q are as defined above;

$R^n$ and $R^o$ represent hydrogen, phenyl; —$C_{1-6}$ straight- or branched-chain alkyl unsubstituted or substituted with one to four $R^i$ groups;

each $R^s$ independently represents hydrogen; phenyl or —$C_{1-6}$ straight- or branched-chain alkyl, unsubstituted or substituted with one to four $R^i$ groups;

each $R^t$ independently represents hydrogen; halo; phenyl; —CN; —$NO_2$; —$NR^uR^v$; —$OR^u$; —$SR^u$; —$CONR^uR^v$; —$COOR^h$; —$SOR^u$; —$SO_2R^u$; —$SO_2NR^uR^v$; —$NR^uSO_2R^v$; —$COR^u$; —$NR^uCOR^v$; —$OCOR^u$; —$OCONR^uR^v$; —$NR^uCO_2R^v$; —$NR^uCONR^vR^w$; —$OCO_2R^v$; —$C_{1-6}$ straight- or branched-chain alkyl, unsubstituted or substituted with one to four $R^i$ groups;

$R^u$ and $R^v$ represent hydrogen or —$C_{1-6}$ straight- or branched-chain alkyl, unsubstituted or substituted with one to four $R^i$ groups;

or $R^u$ and $R^v$ together with any intervening atoms represent a 4–6 membered saturated ring optionally interrupted by one or more of O, S, $NR^w$ or —C(O)—, said ring being unsubstituted or substituted with one to four $R^i$ groups;

each $R^w$ independently represents hydrogen; —$C_{1-6}$ straight- or branched-chain alkyl, unsubstituted or substituted with one to four $R^i$ groups; $C_{3-6}$ cycloalkyl optionally substituted with one to four $R^i$ groups; phenyl optionally substituted with one to four $R^i$ groups, or heteroaryl optionally substituted with 1–4 $R^i$ groups;

or $R^h$ and $R^w$ taken together with any intervening atoms represent a 5–6 membered saturated ring, optionally interrupted by one or two of O, S, $SO_2$, NH or $NCH_3$;

$R^x$ represents hydrogen or a $C_{1-8}$ straight- or branched-chain alkyl, optionally interrupted by one or two of O, S, SO, $SO_2$, $NR^w$, $N^+R^hR^w$, or —C(O)—, said chain being unsubstituted or substituted with one to four of halo, CN, $NO_2$, $OR^w$, $SR^w$, $SOR^w$, $SO_2R^w$, $NR^hR^w$, $N^+(R^h)_2R^w$, —C(O)—$R^w$, C(O)$NR^hR^w$, $SO_2NR^hR^w$, $CO_2R^w$, OC(O)$R^w$, OC(O)$NR^hR^w$, $NR^hC(O)R^w$, $NR^hC(O)NR^hR^w$, or a phenyl or heteroaryl group which is in turn optionally substituted with from one to four $R^i$ groups or with one to two $C_{1-3}$ straight- or branched-chain alkyl groups, said alkyl groups being unsubstituted or substituted with one to four $R^i$ groups;

$R^y$ and $R^z$ represent hydrogen; phenyl; —$C_{1-6}$ straight or branched chain alkyl, unsubstituted or substituted with one to four $R^i$ groups, and optionally interrupted by O, S, $NR^w$, $N^+R^hR^w$ or —C(O)—;

or $R^x$ and $R^y$ together with any intervening atoms represent a 4–6 membered saturated ring optionally interrupted by O, S, $SO_2$, $NR^w$, $N^+R^hR^w$ or —C(O)—, unsubstituted or substituted with 1–4 $R^i$ groups, and when $R^x$ and $R^y$ together represent a 4–6 membered ring as defined above, $R^z$ is as defined above or $R^z$ represents an additional saturated 4–6 membered ring fused to the ring represented by $R^x$ and $R^y$ taken together, optionally interrupted by O, S, $NR^w$ or —C(O)—, said rings being unsubstituted or substituted with one to four $R^i$ groups.

2. A compound in accordance with claim 1 wherein $CO_2M$ represents a carboxylate anion.

3. A compound in accordance with claim 1 wherein one R represents a group which contains a positively charged moiety, and the remaining R groups are selected from hydrogen and $C_{1-6}$ straight or branched chain alkyl, unsubstituted or substituted with one to four $R^d$ groups.

4. A compound in accordance with claim 3 wherein one R represents a group containing a positively charged moiety and the remaining R groups are hydrogen.

5. A compound in accordance with claim 1 wherein the R groups contain from 1–3 positive charges.

6. A compound in accordance with claim 5 wherein the R groups contain two positive charges, balanced by a carboxylate anion and a negatively charged counterion.

7. A compound in accordance with claim 1 wherein one R group represents a —$C_{1-6}$ straight or branched chain alkyl group, substituted with one to four $R^d$ groups, wherein one $R^d$ group represents —R* or Q.

8. A compound in accordance with claim 1 wherein Q is selected from the group consisting of:

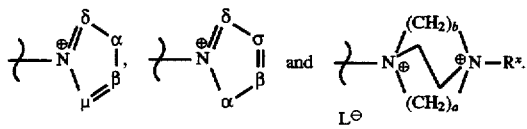

9. A compound in accordance with claim 8 wherein Q represents:

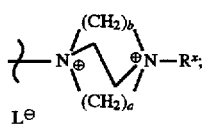

L⁻, a and b are as defined in claim 8, and R* represents a member selected from the group consisting of: hydrogen or a $C_{1-8}$ straight- or branched-chain alkyl, optionally interrupted by one or two of O, S, SO, $SO_2$, $NR^w$, $N^+R^hR^w$, or —C(O)—, said chain being unsubstituted or substituted with one to four of halo, CN, $NO_2$, $OR^w$, $SR^w$, $SOR^w$, $SO_2R^w$, $NR^hR^w$, $N^+(R^h)_2R^w$, —C(O)—

$R^w$, C(O)$NR^hR^w$, $SO_2NR^hR^w$, $CO_2R^w$, OC(O)$R^w$, OC(O)$NR^hR^w$, $NR^hC(O)R^w$, $NR^hC(O)NR^hR^w$, or a phenyl or heteroaryl group which is in turn optionally substituted with from one to four $R^i$ groups or with one to two $C_{1-3}$ straight- or branched-chain alkyl groups, said alkyl groups being unsubstituted or substituted with one to four $R^i$ groups, and $R^h$, $R^i$ and $R^w$ are as defined in claim 8.

10. A compound in accordance with claim 1 wherein Q represents —$N^+R^xR^yR^z$, wherein $R^x$, $R^y$ and $R^z$ are as originally defined.

11. A compound in accordance with claim 1 wherein one R* group is present and is selected from:

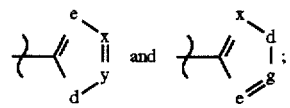

d represents $NR^k$; $R^k$ represents —$C_{1-6}$ straight or branched chain alkyl; and e, g, x and y represent $CR^m$ or $N^+R^k$, with $R^k$ as defined above and $R^m$ representing hydrogen.

12. A compound in accordance with claim 1 wherein:

$CO_2M$ represents a carboxylate anion;

one R group which is attached to the naphthosultam platform contains at least one positively charged moiety, and the remaining R groups are selected from hydrogen and $C_{1-6}$ straight or branched chain alkyl, unsubstituted or substituted with one to four $R^d$ groups;

$R^d$ is as originally defined;

$R^h$ represents hydrogen or a $C_{1-6}$ straight or branched chain alkyl group;

Q is selected from the group consisting of:

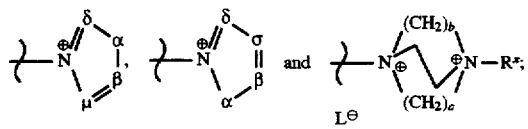

wherein L⁻ is as originally defined; a and b represent 2, and R* represents a member selected from the group consisting of: hydrogen or a $C_{1-8}$ straight- or branched-chain alkyl, optionally interrupted by one or two of O, S, SO, $SO_2$, $NR^w$, $N^+R^hR^w$, or —C(O)—, said chain being unsubstituted or substituted with one to four of halo, CN, $NO_2$, $OR^w$, $SR^w$, $SOR^w$, $SO_2R^w$, $NR^hR^w$, $N^+(R^h)_2R^w$, —C(O)—$R^w$, C(O)$NR^hR^w$, $SO_2NR^hR^w$, $CO_2R^w$, OC(O)$R^w$, OC(O)$NR^hR^w$, $NR^hC(O)R^w$, $NR^hC(O)NR^hR^w$, or a phenyl or heteroaryl group which is in turn optionally substituted with from one to four $R^i$ groups or with one to two $C_{1-3}$ straight- or branched-chain alkyl groups, said alkyl groups being unsubstituted or substituted with one to four $R^i$ groups;

R* is:

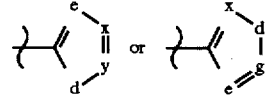

wherein d represents $NR^k$; $R^k$ represents —$C_{1-6}$ straight or branched chain alkyl; and e, g, x and y represent $CR^m$ or $N^+R^k$, with $R^k$ as defined above and $R^m$ representing hydrogen.

13. A compound in accordance with claim 1 represented by formula Ia:

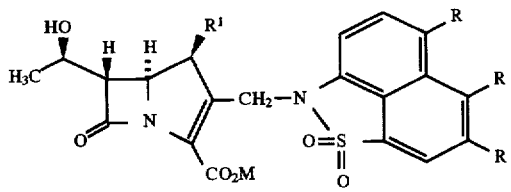

or a pharmaceutically acceptable salt thereof, wherein:
$CO_2M$ represents a carboxylate anion;
one R contains a positively charged moiety, and the other R groups are selected from hydrogen and $C_{1-6}$ straight or branched chain alkyl, unsubstituted or substituted with one to four $R^d$ groups;
$R^d$ is as originally defined;
Q is selected from the group consisting of:

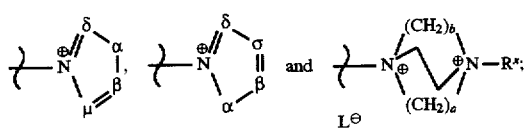

wherein $L^-$, a and b are as originally defined, and $R^x$ represents a member selected from the group consisting of: hydrogen or a $C_{1-8}$ straight- or branched-chain alkyl, optionally interrupted by one or two of O, S, SO, $SO_2$, $NR^w$, $N^+R^hR^w$, or —C(O)—, said chain being unsubstituted or substituted with one to four of halo, CN, $NO_2$, $OR^w$, $SR^w$, $SOR^w$, $SO_2R^w$, $NR^hR^w$, $N^+(R^h)_2R^w$, —C(O)—$R^w$, $C(O)NR^hR^w$, $SO_2NR^hR^w$, $CO_2R^w$, $OC(O)R^w$, $OC(O)NR^hR^w$, $NR^hC(O)R^w$, $NR^hC(O)NR^hR^w$, or a phenyl or heteroaryl group which is in turn optionally substituted with from one to four $R^i$ groups or with one to two $C_{1-3}$ straight- or branched-chain alkyl groups, said alkyl groups being unsubstituted or substituted with one to four $R^i$ groups;
$R^h$ represents hydrogen or a $C_{1-6}$ straight or branched chain alkyl group;
$R^w$ is as originally defined;
$R*$ is:

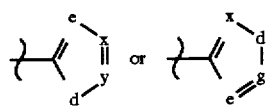

wherein d represents $NR^k$; $R^k$ represents —$C_{1-6}$ straight or branched chain alkyl; and e, g, x and y represent $CR^m$ or $N^+R^k$, with $R^k$ as defined above and $R^m$ representing hydrogen.

14. A compound in accordance with claim 1 represented by formula Ib:

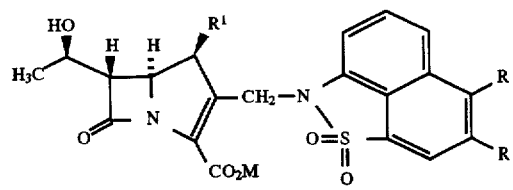

or a pharmaceutically acceptable salt thereof, wherein:
$CO_2M$ represents a carboxylate anion;

one R group is attached to the naphthosultam platform which contains a positively charged moiety, and the other R group is selected from hydrogen and $C_{1-6}$ straight or branched chain alkyl, unsubstituted or substituted with one to four $R^d$ groups;
$R^d$ is as originally defined;
Q is selected from the group consisting of:

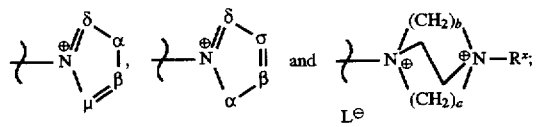

wherein $L^-$, a and b are as originally defined, and $R^x$ represents a member selected from the group consisting of: hydrogen or a $C_{1-8}$ straight- or branched-chain alkyl, optionally interrupted by one or two of O, S, SO, $SO_2$, $NR^w$, $N^+R^hR^w$, or —C(O)—, said chain being unsubstituted or substituted with one to four of halo, CN, $NO_2$, $OR^w$, $SR^w$, $SOR^w$, $SO_2R^w$, $NR^hR^w$, $N^+(R^h)_2R^w$, —C(O)—$R^w$, $C(O)NR^hR^w$, $SO_2NR^hR^w$, $CO_2R^w$, $OC(O)R^w$, $OC(O)NR^hR^w$, $NR^hC(O)R^w$, $NR^hC(O)NR^hR^w$, or a phenyl or heteroaryl group which is in turn optionally substituted with from one to four $R^i$ groups or with one to two $C_{1-3}$ straight- or branched-chain alkyl groups, said alkyl groups being unsubstituted or substituted with one to four $R^i$ groups;
$R^h$ represents hydrogen or a $C_{1-6}$ straight or branched chain alkyl group;
$R^w$ is as originally defined;
$R*$ is:

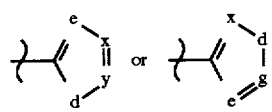

wherein d represents $NR^k$; $R^k$ represents —$C_{1-6}$ straight or branched chain alkyl; and e, g, x and y represent $CR^m$ or $N^+R^k$, with $R^k$ as defined above and $R^m$ representing hydrogen, within this subset, all other variables are as originally defined with respect to formula I.

15. A compound in accordance with claim 1 represented by formula Ic:

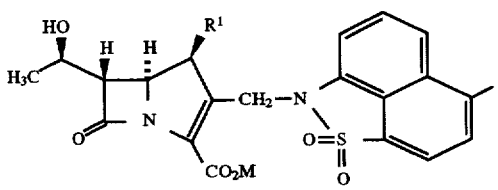

or a pharmaceutically acceptable salt thereof, wherein:
$CO_2M$ represents a carboxylate anion;
one R group is attached to the naphthosultam platform which contains a positively charged moiety, and the other R group is selected from hydrogen, halo and $C_{1-6}$ straight or branched chain alkyl, unsubstituted or substituted with one to four $R^d$ groups;
$R^d$ is as originally defined;

Q is selected from the group consisting of:

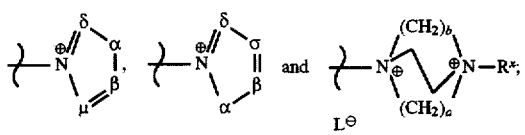

wherein L⁻, a and b are as originally defined, and R* represents a member selected from the group consisting of: hydrogen or a $C_{1-8}$ straight- or branched-chain alkyl, optionally interrupted by one or two of O, S, SO, $SO_2$, NR$^w$, N⁺R$^h$R$^w$, or —C(O)—, said chain being unsubstituted or substituted with one to four of halo, CN, $NO_2$, OR$^w$, SR$^w$, SOR$^w$, $SO_2$R$^w$, NR$^h$R$^w$, N⁺(R$^h$)$_2$R$^w$, —C(O)—R$^w$, C(O)NR$^h$R$^w$, $SO_2$NR$^h$R$^w$, $CO_2$R$^w$, OC(O)R$^w$, OC(O)NR$^h$R$^w$, NR$^h$C(O)R$^w$, NR$^h$C(O)NR$^h$R$^w$, or a phenyl or heteroaryl group which is in turn optionally substituted with from one to four R$^i$ groups or with one to two $C_{1-3}$ straight- or branched-chain alkyl groups, said alkyl groups being unsubstituted or substituted with one to four R$^i$ groups;

R$^h$ represents hydrogen or a $C_{1-6}$ straight or branched chain alkyl group;

R$^w$ is as originally defined;

R* is:

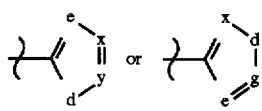

wherein d represents NR$^k$; R$^k$ represents —$C_{1-6}$ straight or branched chain alkyl; and e, g, x and y represent CR$^m$ or N⁺R$^k$, with R$^k$ as defined above and R$^m$ representing hydrogen.

16. A compound in accordance with claim 1 represented by formula Id:

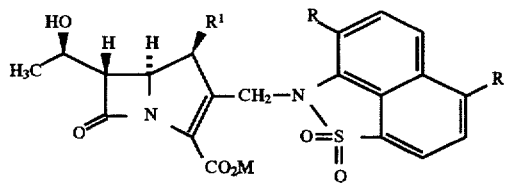

or a pharmaceutically acceptable salt thereof, wherein:
$CO_2$M represents a carboxylate anion;
one R group is attached to the naphthosultam platform which contains a positively charged moiety, and the other R group is selected from hydrogen, halo and $C_{1-6}$ straight or branched chain alkyl, unsubstituted or substituted with one to four R$^d$ groups;
R$^d$ is as originally defined;
Q is selected from the group consisting of:

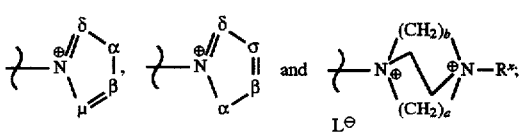

wherein L⁻, a and b are as originally defined, and R* represents a member selected from the group consisting of: hydrogen or a $C_{1-8}$ straight- or branched-chain alkyl, optionally interrupted by one or two of O, S, SO, $SO_2$, NR$^w$, N⁺R$^h$R$^w$, or —C(O)—, said chain being unsubstituted or substituted with one to four of halo, CN, $NO_2$, OR$^w$, SR$^w$, SOR$^w$, $SO_2$R$^w$, NR$^h$R$^w$, N⁺(R$^h$)$_2$R$^w$, —C(O)—R$^w$, C(O)NR$^h$R$^w$, $SO_2$NR$^h$R$^w$, $CO_2$R$^w$, OC(O)R$^w$, OC(O)NR$^h$R$^w$, NR$^h$C(O)R$^w$, NR$^h$C(O)NR$^h$R$^w$, or a phenyl or heteroaryl group which is in turn optionally substituted with from one to four R$^i$ groups or with one to two $C_{1-3}$ straight- or branched-chain alkyl groups, said alkyl groups being unsubstituted or substituted with one to four R$^i$ groups;

R$^h$ represents hydrogen or a $C_{1-6}$ straight or branched chain alkyl group;

R$^w$ is as originally defined;

R* is:

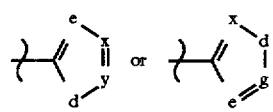

wherein d represents NR$^k$; R$^k$ represents —$C_{1-6}$ straight or branched chain alkyl; and e, g, x and y represent CR$^m$ or N⁺R$^k$, with R$^k$ as defined above and R$^m$ representing hydrogen.

17. A compound in accordance with claim 1 represented by formula Ie:

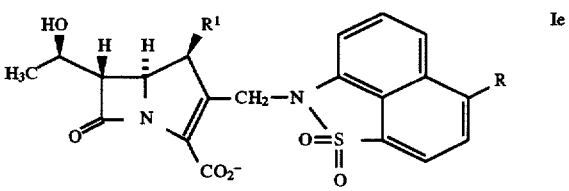

or a pharmaceutically acceptable salt thereof, wherein:

R contains a positively charged moiety selected from the group consisting of: —R*, Q, and a $C_{1-6}$ straight or branched alkyl chain substituted with one R$^d$ group;

R$^d$ is independently selected —R* or Q;

Q is selected from the group consisting of:

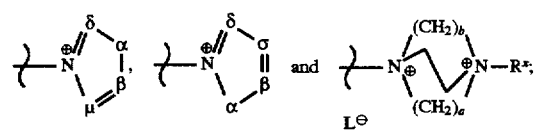

wherein L⁻, a and b are as originally defined, and R* represents a member selected from the group consisting of: hydrogen or a $C_{1-8}$ straight- or branched-chain alkyl, optionally interrupted by one or two of O, S, SO, $SO_2$, NR$^w$, N⁺R$^h$R$^w$, or —C(O)—, said chain being unsubstituted or substituted with one to four of halo, CN, $NO_2$, OR$^w$, SR$^w$, SOR$^w$, $SO_2$R$^w$, NR$^h$R$^w$, N⁺(R$^h$)$_2$R$^w$, —C(O)—R$^w$, C(O)NR$^h$R$^w$, $SO_2$NR$^h$R$^w$, $CO_2$R$^w$, OC(O)R$^w$, OC(O)NR$^h$R$^w$, NR$^h$C(O)R$^w$, NR$^h$C(O)NR$^h$R$^w$, or a phenyl or heteroaryl group which is in turn optionally substituted with from one to four R$^i$ groups or with one to two $C_{1-3}$ straight- or branched-chain alkyl groups, said alkyl groups being unsubstituted or substituted with one to four R$^i$ groups;

R* is

[structure: two alternative fragments with e, x, d, y, g labels]

wherein d represents NR$^k$; R$^k$ represents —C$_{1-6}$ straight or branched chain alkyl; and e, g, x and y represent CR$^m$ or N$^+$R$^k$, with R$^k$ as defined above and R$^m$ representing hydrogen.

18. A compound in accordance with claim 1 represented by formula If:

[structure If]

or a pharmaceutically acceptable salt thereof, wherein:

R contains a positively charged moiety selected from the group consisting of: —R*, Q, and a C$_{1-6}$ straight or branched alkyl chain substituted with one R$^d$ group;

R$^d$ is independently selected —R* or Q;

Q is selected from the group consisting of:

[three structural fragments]

wherein L$^-$, a and b are as originally defined, and R$^x$ represents a member selected from the group consisting of: hydrogen or a C$_{1-8}$ straight- or branched-chain alkyl, optionally interrupted by one or two of O, S, SO, SO$_2$, NR$^w$, N$^+$R$^h$R$^w$, or —C(O)—, said chain being unsubstituted or substituted with one to four of halo, CN, NO$_2$, OR$^w$, SR$^w$, SOR$^w$, SO$_2$R$^w$, NR$^h$R$^w$, N$^+$(R$^h$)$_2$R$^w$, —C(O)—R$^w$, C(O)NR$^h$R$^w$, SO$_2$NR$^h$R$^w$, CO$_2$R$^w$, OC(O)R$^w$, OC(O)NR$^h$R$^w$, NR$^h$C(O)R$^w$, NR$^h$C(O)NR$^h$R$^w$, or a phenyl or heteroaryl group which is in turn optionally substituted with from one to four R$^i$ groups or with one to two C$_{1-3}$ straight- or branched-chain alkyl groups, said alkyl groups being unsubstituted or substituted with one to four R$^i$ groups;

R* is:

[structure: two alternative fragments]

wherein d represents NR$^k$; R$^k$ represents —C$_{1-6}$ straight or branched chain alkyl; and e, g, x and y represent CR$^m$ or N$^+$R$^k$, with R$^k$ as defined above and R$^m$ representing hydrogen.

19. A compound in accordance with claim 17 wherein:

R represents

[structure: —(CH$_2$)$_{1-6}$—N$^+$(CH$_2$)$_b$(CH$_2$)$_a$N$^+$—R$^x$ L$^-$]

and R$^x$, a, b and L$^-$ are as defined in claim 17.

20. A compound in accordance with claim 1 represented by formula Ig:

[structure Ig]

wherein:

R represents

[structure: —(CH$_2$)$_{1-6}$—N$^+$(CH$_2$)$_b$(CH$_2$)$_a$N$^+$—R$^x$ L$^-$]

and R$^x$, a, b and L$^-$ are as originally defined.

21. A compound in accordance with claim 1 represented by the structural formula:

[structure E-1]

[structure E-2]

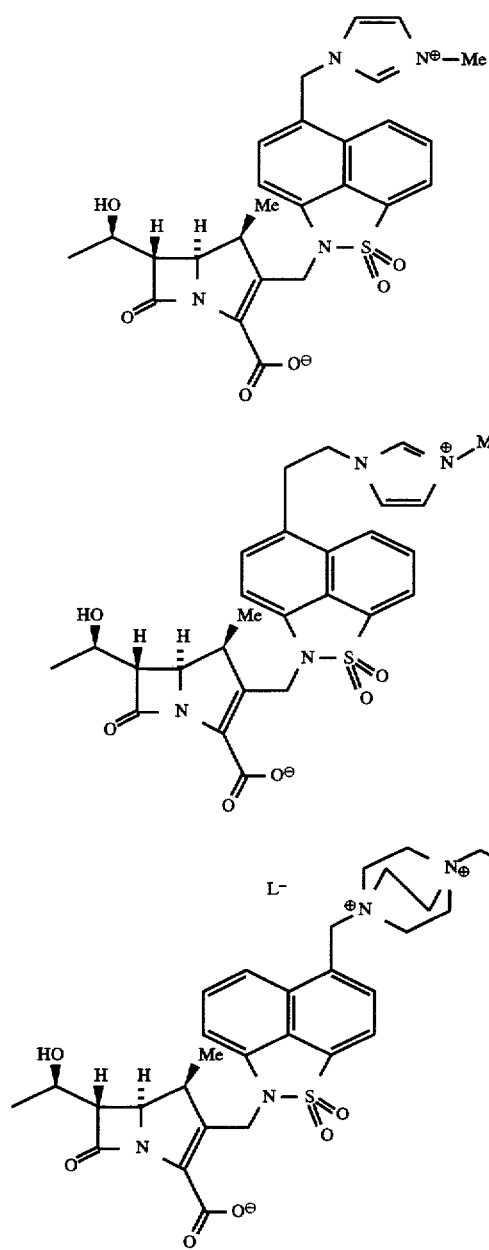

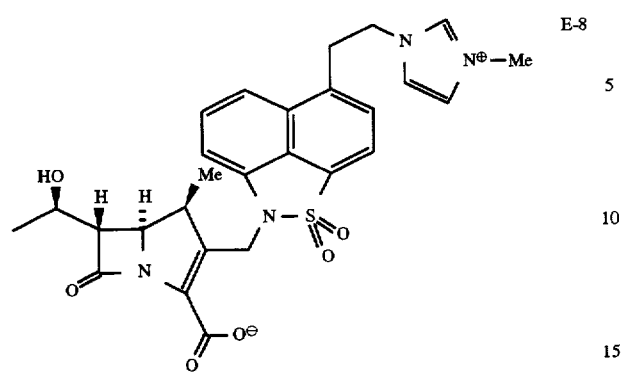
wherein L⁻ is a pharmaceutically acceptable counterion.
22. A compound in accordance with claim 1 represented by the structural formula:
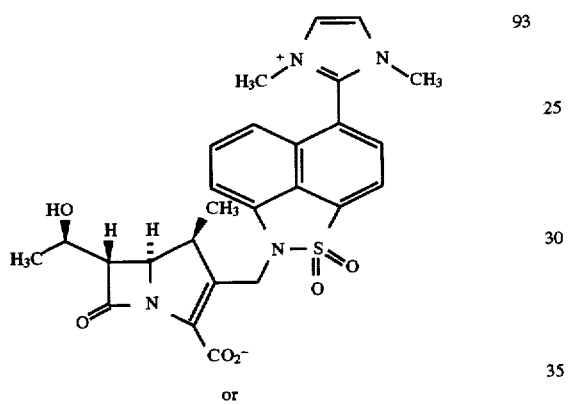
or
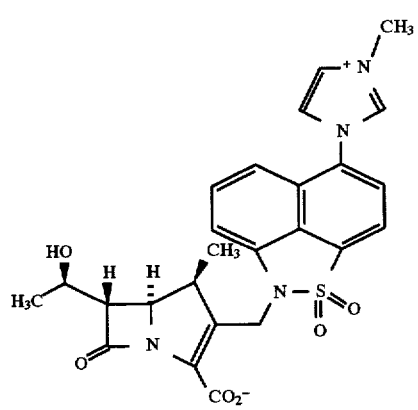
23. A compound in accordance with claim 1 falling within one of the following tables:
TABLE
| # | Q | # | Q | # | Q |
|---|---|---|---|---|---|
| 9 | OH | 10 | PhS | 11 | F |

TABLE-continued

[Structure shown with L⁻ counterion, featuring a carbapenem core with hydroxyethyl, methyl, and CH₂-N(naphthyl-SO₂) substituents, where the naphthalene bears a -CH₂CH₂-Q group]

| # | Q | # | Q | # | Q |
|---|---|---|---|---|---|
| 12 | 3-fluoropropyl-[1,4-diazoniabicyclo] | 13 | ureidopropyl-[1,4-diazoniabicyclo] (H₂N-C(O)-NH-) | 14 | carbamoyloxypropyl-[1,4-diazoniabicyclo] (H₂N-C(O)-O-) |
| 15 | N-methylcarbamoylmethyl-[1,4-diazoniabicyclo] (H₃C-NH-C(O)-CH₂-) | 16 | N,N-dimethylcarbamoylmethyl-[1,4-diazoniabicyclo] (H₃C)₂N-C(O)-CH₂- | 17 | methyl-[1,4-diazoniabicyclo] |
| 18 | methylthiomethyl-[1,4-diazoniabicyclo] (CH₃-S-CH₂-) | 19 | methylsulfinylmethyl-[1,4-diazoniabicyclo] (CH₃-S(O)-CH₂-, S⁺-O⁻) | 20 | methylsulfonylmethyl-[1,4-diazoniabicyclo] (CH₃-SO₂-CH₂-) |
| 21 | phenylthiomethyl-[1,4-diazoniabicyclo] (Ph-S-CH₂-) | 22 | phenylsulfonylmethyl-[1,4-diazoniabicyclo] (Ph-SO₂-CH₂-) | 23 | 3-hydroxypropyl-pyrazinediium (HO-CH₂CH₂CH₂-N⁺=CH-CH=N⁺-) |

TABLE-continued

| # | Q | # | Q | # | Q |
|---|---|---|---|---|---|
| 24 | (aminoethyl-DABCO) | 25 | (aminopropyl-DABCO) | 26 | (phenylcarbamoylmethyl-DABCO) |

TABLE

| # | Q | # | Q | # | Q |
|---|---|---|---|---|---|
| 27 | pyridinium | 28 | (hydroxyethyl-imidazolium) | 29 | quinuclidinium |
| 30 | thiazolium | 31 | oxazolium | 32 | (trialkylammonium) |

TABLE

| # | Q | # | Q | # | Q |
|---|---|---|---|---|---|
| 34 | (carbamoylmethyl-DABCO) | 35 | (hydroxyethyl-DABCO) | 36 | (methyl-imidazolium) |

133
TABLE
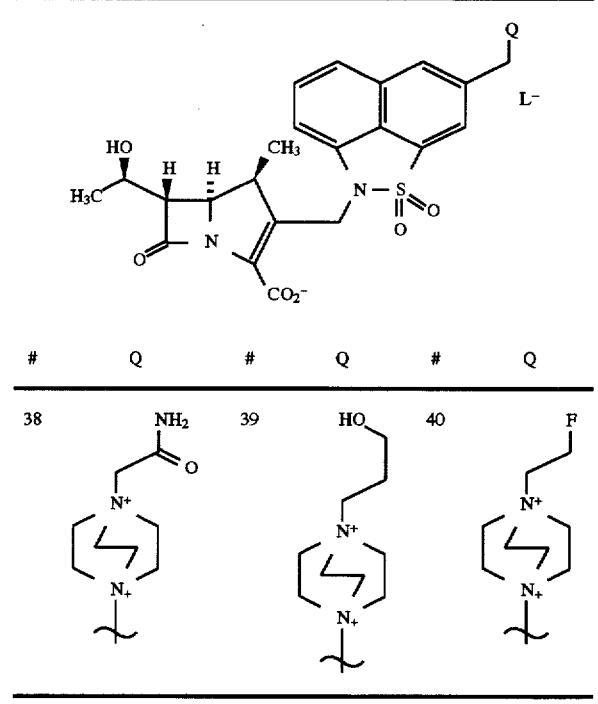
| # | Q | # | Q | # | Q |
|---|---|---|---|---|---|
| 38 | NH₂ (acetamide-DABCO) | 39 | HO-propyl-DABCO | 40 | F-ethyl-DABCO |
TABLE
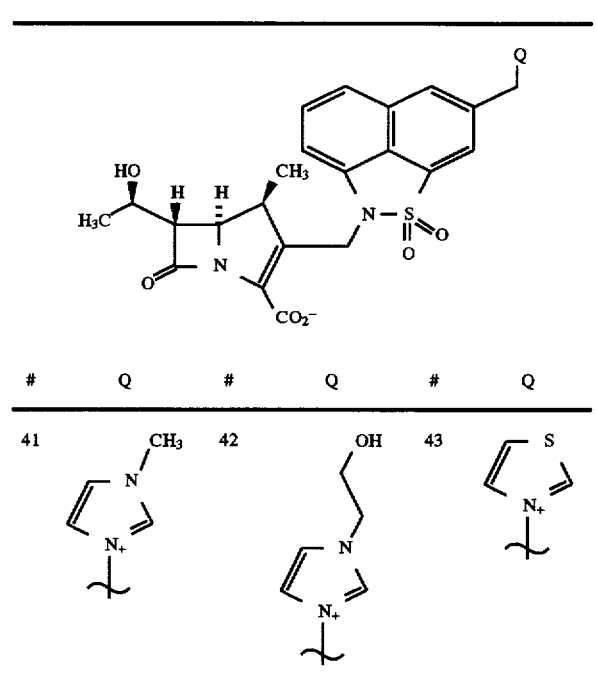
| # | Q | # | Q | # | Q |
|---|---|---|---|---|---|
| 41 | N-methyl-imidazolium | 42 | HO-ethyl-imidazolium | 43 | thiazolium |
134
TABLE
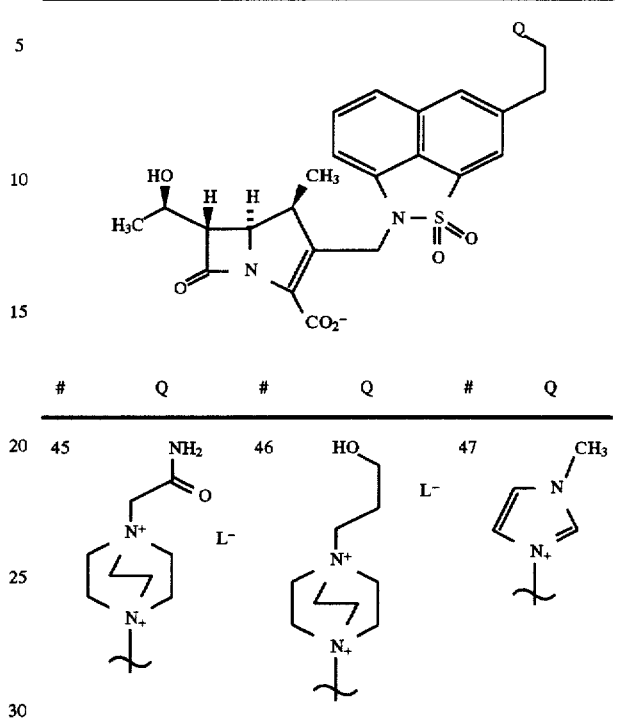
| # | Q | # | Q | # | Q |
|---|---|---|---|---|---|
| 45 | NH₂ (acetamide-DABCO) | 46 | HO-propyl-DABCO | 47 | N-methyl-imidazolium |
TABLE
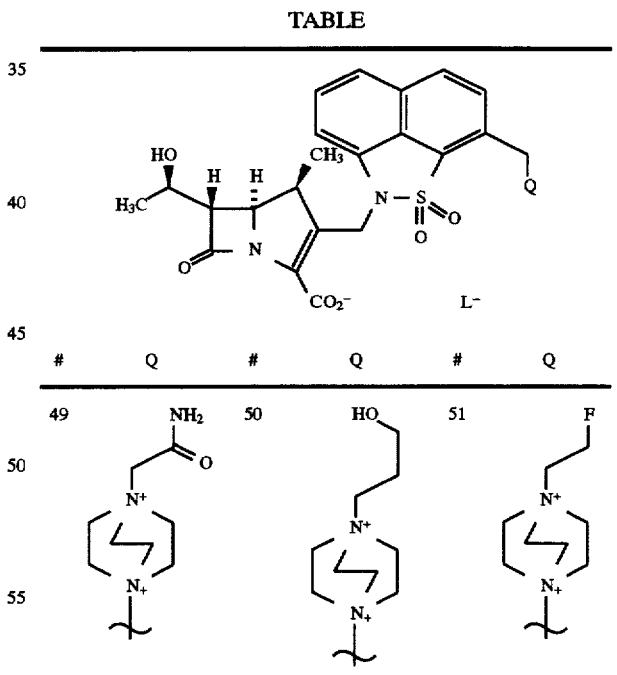
| # | Q | # | Q | # | Q |
|---|---|---|---|---|---|
| 49 | NH₂ (acetamide-DABCO) | 50 | HO-propyl-DABCO | 51 | F-ethyl-DABCO |

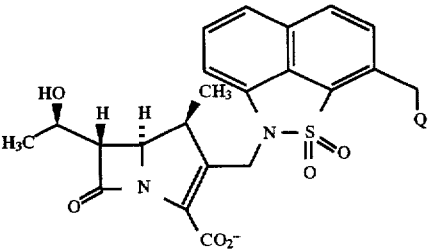

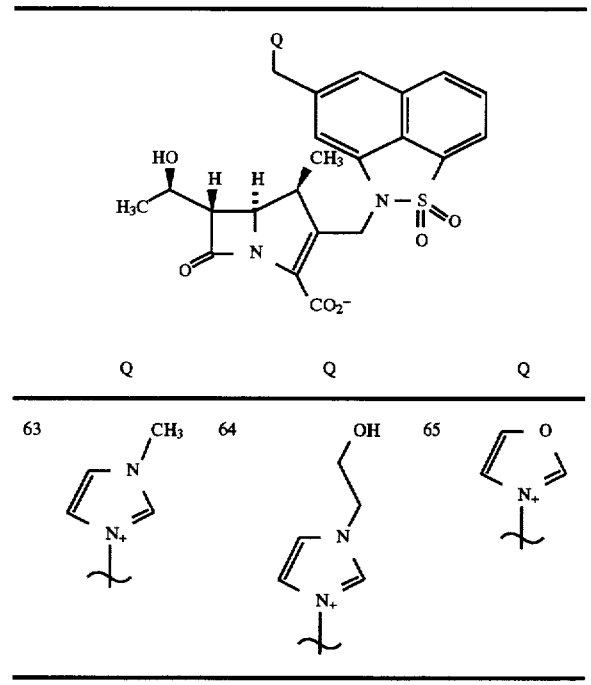
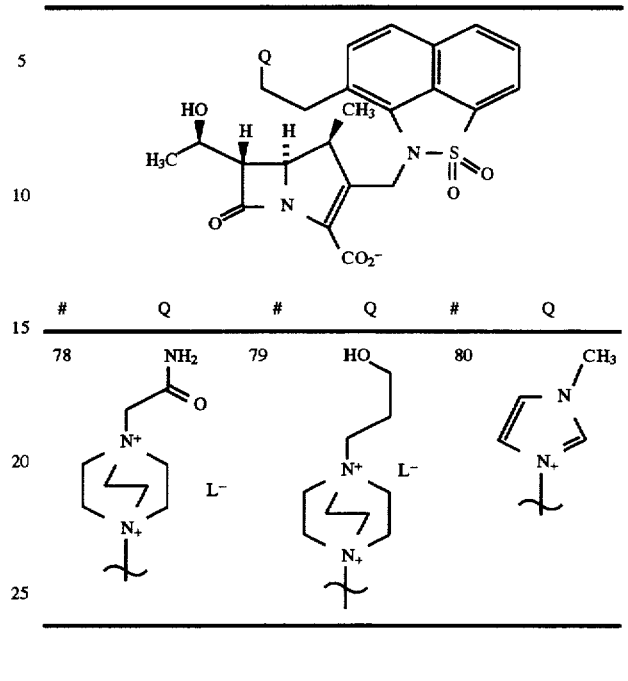
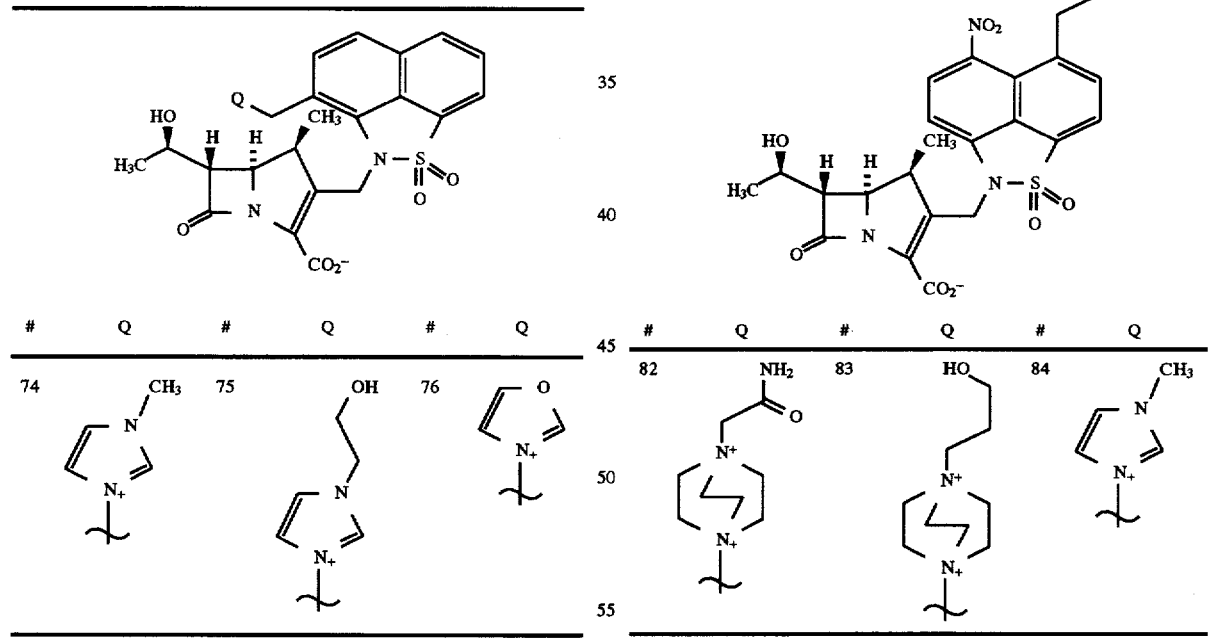

139
TABLE
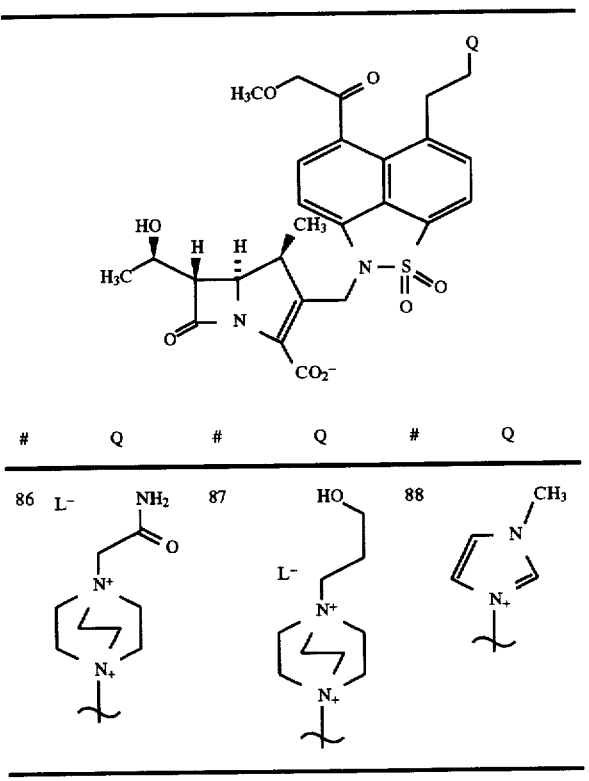
| # | Q | # | Q | # | Q |
|---|---|---|---|---|---|
| 86 | L⁻ —CH₂C(O)NH₂ on DABCO | 87 | HO(CH₂)₃— on DABCO, L⁻ | 88 | N-methylimidazolium |
140
TABLE
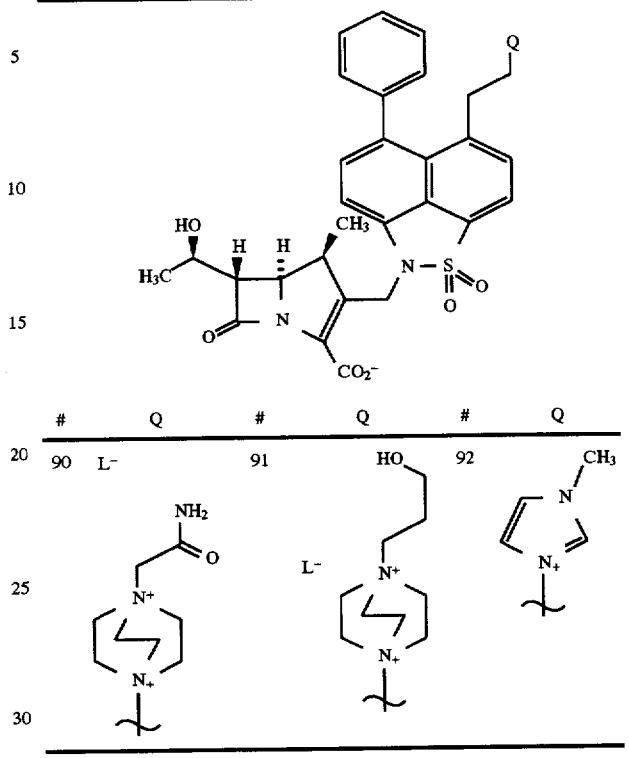
| # | Q | # | Q | # | Q |
|---|---|---|---|---|---|
| 90 | L⁻ —CH₂C(O)NH₂ on DABCO | 91 | HO(CH₂)₃— on DABCO, L⁻ | 92 | N-methylimidazolium |

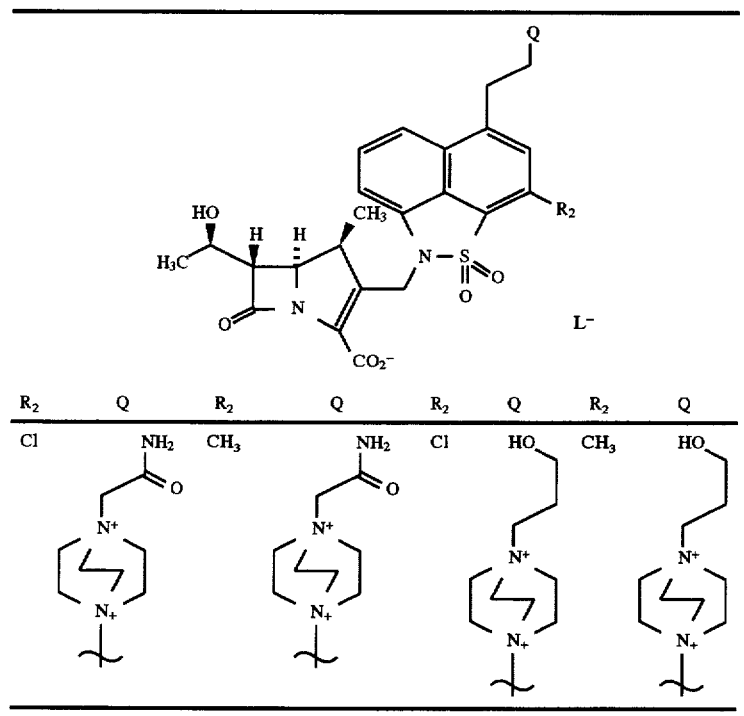
| $R_2$ | Q | $R_2$ | Q | $R_2$ | Q | $R_2$ | Q |
|---|---|---|---|---|---|---|---|
| Cl | | CH₃ | | Cl | | CH₃ | |
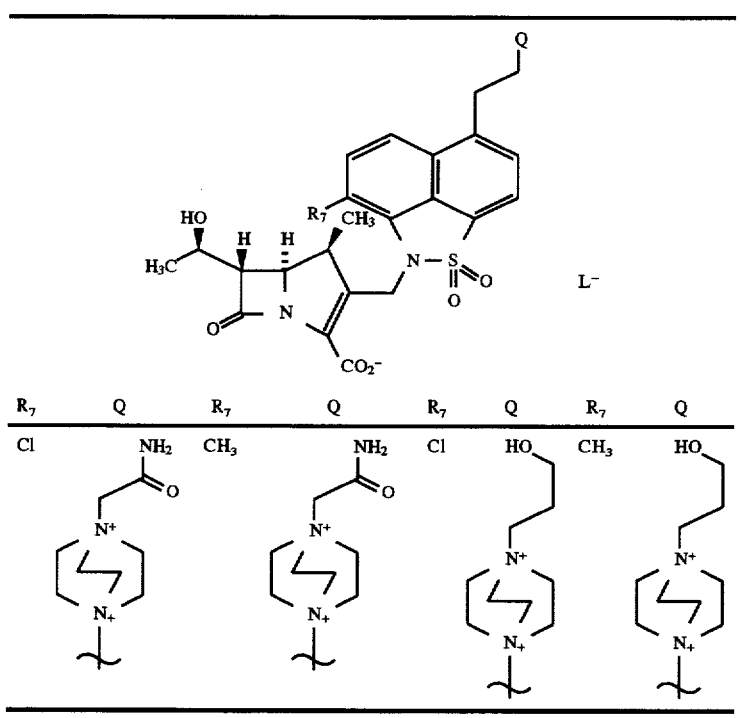
| $R_7$ | Q | $R_7$ | Q | $R_7$ | Q | $R_7$ | Q |
|---|---|---|---|---|---|---|---|
| Cl | | CH₃ | | Cl | | CH₃ | | wherein L⁻ represents a pharmaceutically acceptable counterion.

24. A pharmaceutical composition comprised of a compound in accordance with claim 1 in combination with a pharmaceutically acceptable carrier.

25. A method of treating or preventing a bacterial infection in a mammalian patient in need thereof, comprising administering to said patient an effective amount of a compound of claim 1.

26. A compound represented by the structure:

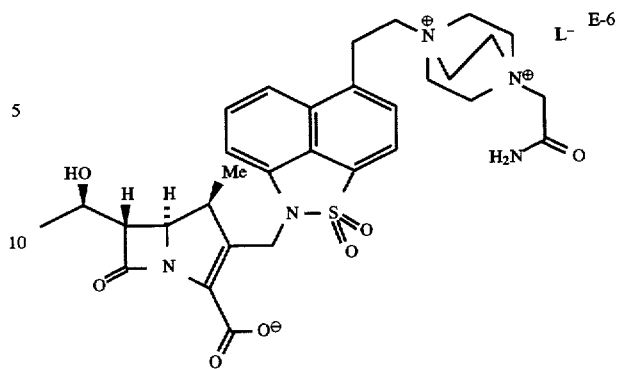

wherein L⁻ represents a pharmaceutically acceptable cation.

* * * * *

UNITED STATES PATENT AND TRADEMARK OFFICE
CERTIFICATE OF CORRECTION

PATENT NO. : 5,756,725
DATED : May 26, 1998
INVENTOR(S) : Robert R. Wilkening, Ronald W. Ratcliffe, Timothy A. Blizzard It is certified that error appears in the above-identified patent and that said Letters Patent is hereby corrected as shown below:

In Claim 21, Compound E-7 is replaced with the following corrected structure:

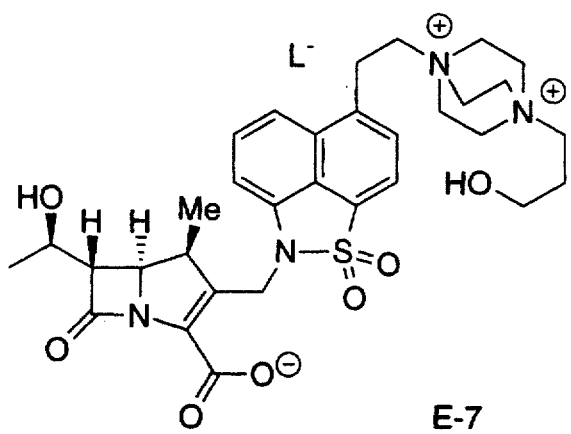

E-7

Signed and Sealed this

First Day of September, 1998

BRUCE LEHMAN

Attest:

Attesting Officer

Commissioner of Patents and Trademarks